US011667680B2

(12) United States Patent
Oeser et al.

(10) Patent No.: US 11,667,680 B2
(45) Date of Patent: Jun. 6, 2023

(54) REGULATION OF THE RAS/CAMP/PKA SIGNALING PATHWAY IN YEASTS FOR OBTAINING A FERMENTATION PRODUCT DURING FERMENTATION

(71) Applicant: Lallemand Hungary Liquidity Management LLC, Budapest (HU)

(72) Inventors: Michelle Oeser, Croydon, NH (US); Brooks Henningsen, Winchester, NH (US); Janet Fisher, Norwich, VT (US); Charles F. Rice, Hopkinton, NH (US); Allan Froehlich, Norwich, VT (US); Aaron Argyros, Etna, NH (US); Rintze M. Zelle, East Thetford, VT (US)

(73) Assignee: Lallemand Hungary Liquidity Management LLC, Budapest (HU)

( * ) Notice: Subject to any disclaimer, the term of this patent is extended or adjusted under 35 U.S.C. 154(b) by 0 days.

(21) Appl. No.: 16/085,959

(22) PCT Filed: Mar. 17, 2017

(86) PCT No.: PCT/EP2017/056456
§ 371 (c)(1),
(2) Date: Sep. 17, 2018

(87) PCT Pub. No.: WO2017/158189
PCT Pub. Date: Sep. 21, 2017

(65) Prior Publication Data
US 2019/0106464 A1    Apr. 11, 2019

Related U.S. Application Data

(60) Provisional application No. 62/310,251, filed on Mar. 18, 2016.

(51) Int. Cl.
| | |
|---|---|
| C07K 14/395 | (2006.01) |
| C12N 1/22 | (2006.01) |
| C12P 7/06 | (2006.01) |
| C12N 15/113 | (2010.01) |
| C12N 15/52 | (2006.01) |
| C12N 15/81 | (2006.01) |

(52) U.S. Cl.
CPC .............. *C07K 14/395* (2013.01); *C12N 1/22* (2013.01); *C12N 15/113* (2013.01); *C12N 15/52* (2013.01); *C12N 15/815* (2013.01); *C12P 7/06* (2013.01); *C12P 7/065* (2013.01); *Y02E 50/10* (2013.01)

(58) Field of Classification Search
None
See application file for complete search history.

(56) References Cited

U.S. PATENT DOCUMENTS

| | | | |
|---|---|---|---|
| 8,993,301 B2 | 3/2015 | Boles et al. | |
| 9,206,444 B2 | 12/2015 | Brevnova et al. | |
| 9,303,253 B2 | 4/2016 | Van Maris et al. | |
| 9,920,312 B2 * | 3/2018 | Froehlich | C12N 9/92 |
| 10,465,181 B2 * | 11/2019 | Froehlich | C12P 7/06 |
| 2010/0304454 A1 * | 12/2010 | De Bont | C12N 9/80 |
| | | | 435/161 |
| 2014/0206070 A1 * | 7/2014 | Boles | C12N 15/00 |
| | | | 435/254.21 |
| 2016/0040153 A1 | 2/2016 | Froehlich et al. | |

FOREIGN PATENT DOCUMENTS

| | | |
|---|---|---|
| EP | 1499708 B2 | 2/2012 |
| WO | 2004/003217 A1 | 1/2004 |
| WO | 2013/071112 A1 | 5/2013 |
| WO | 2016/024215 A1 | 2/2016 |

OTHER PUBLICATIONS

Chica et al. Curr Opin Biotechnol. Aug. 2005;16(4):378-84. (Year: 2005).*
Singh et al. Curr Protein Pept Sci. 2017, 18, 1-11 (Year: 2017).*
Partow et al. Yeast 2010; 27: 955-964. Published online Jul. 12, 2010 (Year: 2010).*
Bornscheuer et al. Curr Protoc Protein Sci. Nov. 2011;Chapter 26:Unit26.7. (Year: 2011).*
Yoshikuni et al. Curr Opin Chem Biol. Apr. 2007;11(2):233-9. (Year: 2007).*
Sanchez et al. Biotechnol Biofuels. 2010; 3: 13. Published online Jun. 15, 2010 (Year: 2010).*
Accession P01120. Jul. 21, 1986 (Year: 1986).*
Cazzaniga et al., "Modeling and stochastic simulation of the Ras/cAMP/PKA pathway in the yeast *Saccharomyces cerevisiae* evidences a key regulatory function for intracellular guanine nucleotides pools," *Journal of Biotechnology* 133:377-385, 2008.
Hong et al., "Recovery of Phenotypes Obtained by Adaptive Evolution through Inverse Metabolic Engineering," *Applied and Environmental Microbiology* 78(21):7579-7586, 2012.
Kwast et al., "Genomic Analyses of Anaerobically Induced Genes in *Saccharomyces cerevisiae*: Functional Roles of Rox1 and Other Factors in Mediating the Anoxic Response," *Journal of Bacteriology* 184(1):250-265, 2002.

(Continued)

*Primary Examiner* — Christian L Fronda
(74) *Attorney, Agent, or Firm* — Seed IP Law Group LLP

(57) ABSTRACT

The present disclosure relates to the modulation in the RAS/cAMP/PKA signaling pathway for maintaining the propagation efficiency and increasing fermentation efficiency of yeast cells. The present disclosure provides yeast cells having or engineered to exhibit a modulation in signaling in a RAS/cAMP/PKA pathway, depending on conditions. For example the yeast cells can be selected or genetically modified to express a mutated Ras1 protein, a mutated Ras2 protein, a mutated Ira1 protein and/or a mutated Ira2 protein, optionally in combination with specific promoters. Also provided herewith are methods for propagating the yeast cells as well as using the yeast cells to generate a fermented product (such as ethanol).

16 Claims, 8 Drawing Sheets

Specification includes a Sequence Listing.

(56) References Cited

OTHER PUBLICATIONS

Mbonyi et al., "Requirement of One Functional RAS Gene and Inability of an Oncogenic ras Variant to Mediate the Glucose-Induced Cyclic AMP Signal in the Yeast *Saccharomyces cerevisiae*," *Molecular and Cellular Biology* 8(8):3051-3057, 1988.

Tai et al., "Two-dimensional Transcriptome Analysis in Chemostat Cultures," *The Journal of Biological Chemistry* 280(1):437-447, 2005.

Tamanoi, "Ras Signaling in Yeast," *Genes & Cancer* 2(3):210-215, 2011.

Temeles et al., "Yeast and mammalian ras proteins have conserved biochemical properties," *Nature 313*, 1985, 4 pages.

Ter Linde et al., "Genome-Wide Transcriptional Analysis of Aerobic and Anaerobic Chemostat Cultures of *Saccharomyces cerevisiae*," *Journal of Bacteriology* 181(24):7409-7413, 1999.

Wang et al., "Ras and Gpa2 Mediate One Branch of a Redundant Glucose Signaling Pathway in Yeast," *PLoS* 2(5):0610-0622, 2004.

Maxon et al., "Aeration Studies on Propagation of Baker's Yeast," *Industrial and Engineering Chemistry* 45(11):2554-2560, 1953.

Suomalainen, "Changes in the Cell Constitution of Baker's Yeast in Changing Growth Conditions," *Pure and Applied Chemistry* 7(4):639-654, https://doi.org/10.1351/pac196307040639, 1963.

\* cited by examiner

SEQUENCE LISTING

<160> NUMBER OF SEQ ID NOS: 11

<210> SEQ ID NO 1
<211> LENGTH: 322
<212> TYPE: PRT
<213> ORGANISM: Saccharomyces cerevisiae

<400> SEQUENCE: 1

```
Met Pro Leu Asn Lys Ser Asn Ile Arg Glu Tyr Lys Leu Val Val Val
1               5                   10                  15

Gly Gly Gly Gly Val Gly Lys Ser Ala Leu Thr Ile Gln Leu Thr Gln
            20                  25                  30

Ser His Phe Val Asp Glu Tyr Asp Pro Thr Ile Glu Asp Ser Tyr Arg
        35                  40                  45

Lys Gln Val Val Ile Asp Asp Glu Val Ser Ile Leu Asp Ile Leu Asp
    50                  55                  60

Thr Ala Gly Gln Glu Glu Tyr Ser Ala Met Arg Glu Gln Tyr Met Arg
65                  70                  75                  80

Asn Gly Glu Gly Phe Leu Leu Val Tyr Ser Ile Thr Ser Lys Ser Ser
                85                  90                  95

Leu Asp Glu Leu Met Thr Tyr Tyr Gln Gln Ile Leu Arg Val Lys Asp
            100                 105                 110

Thr Asp Tyr Val Pro Ile Val Val Gly Asn Lys Ser Asp Leu Glu
        115                 120                 125

Asn Glu Lys Gln Val Ser Tyr Gln Asp Gly Leu Asn Met Ala Lys Gln
    130                 135                 140

Met Asn Ala Pro Phe Leu Glu Thr Ser Ala Lys Gln Ala Ile Asn Val
145                 150                 155                 160

Glu Glu Ala Phe Tyr Thr Leu Ala Arg Leu Val Arg Asp Glu Gly Gly
                165                 170                 175

Lys Tyr Asn Lys Thr Leu Thr Glu Asn Asp Asn Ser Lys Gln Thr Ser
            180                 185                 190

Gln Asp Thr Lys Gly Ser Gly Ala Asn Ser Val Pro Arg Asn Ser Gly
        195                 200                 205

Gly His Arg Lys Met Ser Asn Ala Ala Asn Gly Lys Asn Val Asn Ser
    210                 215                 220

Ser Thr Thr Val Val Asn Ala Arg Asn Ala Ser Ile Glu Ser Lys Thr
225                 230                 235                 240

Gly Leu Ala Gly Asn Gln Ala Thr Asn Gly Lys Thr Gln Thr Asp Arg
                245                 250                 255

Thr Asn Ile Asp Asn Ser Thr Gly Gln Ala Gly Gln Ala Asn Ala Gln
            260                 265                 270

Ser Ala Asn Thr Val Asn Asn Arg Val Asn Asn Ser Lys Ala Gly
    275                 280                 285

Gln Val Ser Asn Ala Lys Gln Ala Arg Lys Gln Ala Ala Pro Gly
        290                 295                 300

Gly Asn Thr Ser Glu Ala Ser Lys Ser Gly Ser Gly Cys Cys Ile
305                 310                 315                 320

Ile Ser
```

<210> SEQ ID NO 2
<211> LENGTH: 322
<212> TYPE: PRT
<213> ORGANISM: Saccharomyces cerevisiae

<400> SEQUENCE: 2

```
Met Pro Leu Asn Lys Ser Asn Ile Arg Glu Tyr Lys Leu Val Val Val
1               5                   10                  15

Gly Gly Gly Gly Val Gly Lys Ser Ala Leu Thr Ile Gln Leu Thr Gln
            20                  25                  30

Ser His Phe Val Asp Glu Tyr Asp Pro Thr Ile Glu Asp Ser Tyr Arg
        35                  40                  45

Lys Gln Val Val Ile Asp Asp Glu Val Ser Ile Leu Asp Ile Leu Asp
    50                  55                  60

Thr Thr Gly Gln Glu Glu Tyr Ser Ala Met Arg Glu Gln Tyr Met Arg
65                  70                  75                  80

Asn Gly Glu Gly Phe Leu Leu Val Tyr Ser Ile Thr Ser Lys Ser Ser
                85                  90                  95

Leu Asp Glu Leu Met Thr Tyr Tyr Gln Gln Ile Leu Arg Val Lys Asp
            100                 105                 110

Thr Asp Tyr Val Pro Ile Val Val Gly Asn Lys Ser Asp Leu Glu
        115                 120                 125

Asn Glu Lys Gln Val Ser Tyr Gln Asp Gly Leu Asn Met Ala Lys Gln
130                 135                 140

Met Asn Ala Pro Phe Leu Glu Thr Ser Ala Lys Gln Ala Ile Asn Val
145                 150                 155                 160

Glu Glu Ala Phe Tyr Thr Leu Ala Arg Leu Val Arg Asp Glu Gly Gly
                165                 170                 175

Lys Tyr Asn Lys Thr Leu Thr Glu Asn Asp Asn Ser Lys Gln Thr Ser
            180                 185                 190

Gln Asp Thr Lys Gly Ser Gly Ala Asn Ser Val Pro Arg Asn Ser Gly
        195                 200                 205

Gly His Arg Lys Met Ser Asn Ala Ala Asn Gly Lys Asn Val Asn Ser
210                 215                 220

Ser Thr Thr Val Val Asn Ala Arg Asn Ala Ser Ile Glu Ser Lys Thr
225                 230                 235                 240

Gly Leu Ala Gly Asn Gln Ala Thr Asn Gly Lys Thr Gln Thr Asp Arg
                245                 250                 255

Thr Asn Ile Asp Asn Ser Thr Gly Gln Ala Gly Gln Ala Asn Ala Gln
            260                 265                 270

Ser Ala Asn Thr Val Asn Asn Arg Val Asn Asn Ser Lys Ala Gly
        275                 280                 285

Gln Val Ser Asn Ala Lys Gln Ala Arg Lys Gln Ala Ala Pro Gly
        290                 295                 300

Gly Asn Thr Ser Glu Ala Ser Lys Ser Gly Ser Gly Gly Cys Cys Ile
305                 310                 315                 320

Ile Ser

<210> SEQ ID NO 3
<211> LENGTH: 969
<212> TYPE: DNA
<213> ORGANISM: Artificial Sequence
<220> FEATURE:
<223> OTHER INFORMATION: Nucleic acid sequence coding for a mutated
      Ras2p
<220> FEATURE:
<221> NAME/KEY: variation
<222> LOCATION: (198)..(198)
<223> OTHER INFORMATION: n = a, c, t or g
<220> FEATURE:
<221> NAME/KEY: misc_feature
<222> LOCATION: (198)..(198)
<223> OTHER INFORMATION: n is a, c, g, or t
```

<400> SEQUENCE: 3

```
atgcctttga acaagtcgaa cataagagag tacaagctag tcgtcgttgg tggtggtggt    60
gttggtaaat ctgctttgac catacaattg acccaatcgc actttgtaga tgaatacgat   120
cccacaattg aggattcata caggaagcaa gtggtgattg atgatgaagt gtctatattg   180
gacattttgg atactacngg gcaggaagaa tactctgcta tgagggaaca atacatgcgc   240
aacggcgaag gattcctatt ggtttactct ataacatcca agtcgtctct tgatgagctt   300
atgacttact atcaacagat attgagagtc aaagataccg actatgttcc aattgtggtt   360
gttggtaaca atctgatttt agaaaacgaa aaacaggtct cttaccagga cgggttgaac   420
atggcaaagc aaatgaacgc tcctttcttg agacatctg ctaagcaagc aatcaacgtg   480
gaagaggcgt tttacactct agcacgttta gttagagacg aaggcggcaa gtacaacaag   540
actttgacgg aaaatgacaa ctccaagcaa acttctcaag atacaaaagg gagcggtgcc   600
aactctgtgc ctagaaatag cggtggccac aggaagatga gcaatgctgc caacggtaaa   660
aatgtgaaca gtagcacaac tgtcgtgaat gccaggaatg caagcataga gagtaagaca   720
gggttggcag gcaaccaggc gacaaatggt aagacacaaa ctgatcgcac caatatagac   780
aattccacgg gccaagctgg tcaggccaac gctcaaagcg ctaatacggt taataatcgt   840
gtaaataata atagtaaggc cggtcaagtt tcaaatgcta acaggctag gaagcagcaa   900
gctgcacccg gcggtaacac cagtgaagcc tccaagagcg gatcgggtgg ctgttgtatt   960
ataagttaa                                                           969
```

<210> SEQ ID NO 4
<211> LENGTH: 969
<212> TYPE: DNA
<213> ORGANISM: Saccharomyces cerevisiae

<400> SEQUENCE: 4

```
atgcctttga acaagtcgaa cataagagag tacaagctag tcgtcgttgg tggtggtggt    60
gttggtaaat ctgctttgac catacaattg acccaatcgc actttgtaga tgaatacgat   120
cccacaattg aggattcata caggaagcaa gtggtgattg atgatgaagt gtctatattg   180
gacattttgg atactgcagg gcaggaagaa tactctgcta tgagggaaca atacatgcgc   240
aacggcgaag gattcctatt ggtttactct ataacatcca agtcgtctct tgatgagctt   300
atgacttact atcaacagat attgagagtc aaagataccg actatgttcc aattgtggtt   360
gttggtaaca atctgatttt agaaaacgaa aaacaggtct cttaccagga cgggttgaac   420
atggcaaagc aaatgaacgc tcctttcttg agacatctg ctaagcaagc aatcaacgtg   480
gaagaggcgt tttacactct agcacgttta gttagagacg aaggcggcaa gtacaacaag   540
actttgacgg aaaatgacaa ctccaagcaa acttctcaag atacaaaagg gagcggtgcc   600
aactctgtgc ctagaaatag cggtggccac aggaagatga gcaatgctgc caacggtaaa   660
aatgtgaaca gtagcacaac tgtcgtgaat gccaggaatg caagcataga gagtaagaca   720
gggttggcag gcaaccaggc gacaaatggt aagacacaaa ctgatcgcac caatatagac   780
aattccacgg gccaagctgg tcaggccaac gctcaaagcg ctaatacggt taataatcgt   840
gtaaataata atagtaaggc cggtcaagtt tcaaatgcta acaggctag gaagcagcaa   900
gctgcacccg gcggtaacac cagtgaagcc tccaagagcg gatcgggtgg ctgttgtatt   960
ataagttaa                                                           969
```

<210> SEQ ID NO 5
<211> LENGTH: 969
<212> TYPE: DNA
<213> ORGANISM: Saccharomyces cerevisiae

<400> SEQUENCE: 5

| | |
|---|---|
| atgcctttga caagtcgaa cataagagag tacaagctag tcgtcgttgg tggtggtggt | 60 |
| gttggtaaat ctgctttgac catacaattg acccaatcgc actttgtaga tgaatacgat | 120 |
| cccacaattg aggattcata caggaagcaa gtggtgattg atgatgaagt gtctatattg | 180 |
| gacattttgg atactacagg gcaggaagaa tactctgcta tgagggaaca atacatgcgc | 240 |
| aacggcgaag gattcctatt ggtttactct ataacatcca agtcgtctct tgatgagctt | 300 |
| atgacttact atcaacagat attgagagtc aaagataccg actatgttcc aattgtggtt | 360 |
| gttggtaaca atctgatttt agaaaacgaa aaacaggtct cttaccagga cgggttgaac | 420 |
| atggcaaagc aaatgaacgc tcctttcttg gagacatctg ctaagcaagc aatcaacgtg | 480 |
| gaagaggcgt tttacactct agcacgttta gttagagacg aaggcggcaa gtacaacaag | 540 |
| actttgacgg aaaatgacaa ctccaagcaa acttctcaag atacaaaagg gagcggtgcc | 600 |
| aactctgtgc ctagaaatag cggtggccac aggaagatga gcaatgctgc caacggtaaa | 660 |
| aatgtgaaca gtagcacaac tgtcgtgaat gccaggaatg caagcataga gagtaagaca | 720 |
| gggttggcag gcaaccaggc gacaaatggt aagcacaaa ctgatcgcac caatatagac | 780 |
| aattccacgg gccaagctgg tcaggccaac gctcaaagcg ctaataccggt taataatcgt | 840 |
| gtaaataata atagtaaggc cggtcaagtt tcaaatgcta acaggctag gaagcagcaa | 900 |
| gctgcacccg gcggtaacac cagtgaagcc tccaagagcg gatcgggtgg ctgttgtatt | 960 |
| ataagttaa | 969 |

<210> SEQ ID NO 6
<211> LENGTH: 9246
<212> TYPE: DNA
<213> ORGANISM: Saccharomyces cerevisiae

<400> SEQUENCE: 6

| | |
|---|---|
| atgtcccagc ccactaagaa taagaagaaa gaacacggga ccgattccaa gtcatcccgc | 60 |
| atgactcgga cgttggttaa tcatattctt tttgaaagaa ttctcccgat ccttccggtg | 120 |
| gagtctaatc taagtaccta ttcggaagtg gaagagtatt cctcattcat ttcatgcaga | 180 |
| tctgtgctca ttaacgttac cgtttcccaa gatgcaaacg ctatggtgga aggcaccttg | 240 |
| gagttgatag aatcgcttct tcaagggcac gaaatcattt cagataagtg tagcagtgac | 300 |
| gttattgaat caatactgat tatactaaga ttgttaagtg atgcgctaga gtataattgg | 360 |
| caaaatcaag aaagccttca ttacaacgac atttcgactc acgtagaaca tgaccaagaa | 420 |
| cagaagtaca gaccaaagct taacagtatt ctgcccgact ctcgtcgac tcattccaat | 480 |
| ggcaacaaac acttttttcca ccagagcaaa cctcaggcac tgataccgga actggcatcg | 540 |
| aaattgcttg agagttgcgc gaagttgaag ttcaatacaa gaactttgca aattttacaa | 600 |
| aatatgatca gtcatgttca tggaaacatt ctaacgactt tgagttcctc gattcttccc | 660 |
| cgccacaaat cctatctgac aaggcacaac catccttctc attgtaaaat gattgactct | 720 |
| actctaggcc atattctccg atttgtagcg gcttccaatc cgtccgagta ttttgaattt | 780 |
| atcagaaaga gtgtgcaagt gcccgtaaca cagacacaca cacacgca ttcacactcc | 840 |
| cattcacact ctttgccatc ttccgtttat aacagcatag tgccccactt tgatcttttc | 900 |

```
agcttcatct atttaagcaa gcataatttt aagaaatact tggaactcat caaaaactta    960
tcggtgacgt taaggaaaac gatttatcat tgcctacttt tgcattacag cgccaaagca   1020
ataatgtttt ggataatggc taggcctgcg gaatattatg aactcttcaa cttattaaaa   1080
gataataaca atgaacactc gaatccttaa acacgttaa accatacact tttcgaggag    1140
atccattcga cttttaatgt gaatagcatg ataaccacca atcaaaatgc tcatcaaggc   1200
tcatcttccc cttcgtcctc ctcgccatcg tcaccaccta gctcatcatc atcggataac   1260
aacaatcaaa acataatagc aaaatcctta agtcgtcagc tttctcacca ccagtcatac   1320
attcaacagc agtctgaaag aaaactacat tcttcatgga ctacaaactc tcaatcctct   1380
acttcactgt catcttcaac gtctaattca acaacaactg atttctctac tcacactcaa   1440
ccaggagaat acgacccttc cttaccagat actcccacga tgtctaacat cactattagt   1500
gcatcttcat tattatctca aactccaact ccaacaacac aattgcaaca gcggttgaac   1560
tcagcagctg cagccgccgc cgcagctgct tcaccatcga attccacccc aactggatac   1620
acagcagagc aacaaagtcg cgcttcatac gatgcacaca aaactggcca tactggtaag   1680
gattatgacg aacattttt gtctgtcact cgtttggata atgttttgga gttatacacg    1740
cactttgatg atactgaggt actaccacac acatccgtac tgaagttttt aactactttg   1800
acaatgttcg atattgacct ttttaatgaa ttaaacgcta catcattcaa atatattcct   1860
gattgtacta tgcatcgtcc aaaagaaaga acaagttctt tcaataatac tgcacacgag   1920
acaggttccg aaaagacttc gggtataaaa catattacac aaggcttaaa gaaattaact   1980
tctttacctt cctcaaccaa aaaaactgta aaatttatga agatgttgct aagaaattta   2040
aatgggaatc aagctgtatc agatgttgcc ctcttagata caatgagggc cttactatca   2100
ttctttacaa tgacttctgc ggtctttctc gtggatagaa acttaccctc agtactttt    2160
gccaagagac tcatccccat aatggggaca aatttaagcg tcggtcaaga ctggaattca   2220
aaaataaata acagtttgat ggtttgtttg aaaaaaaact ccaccacgtt tgttcaatta   2280
caattaatat tcttctcttc agctattcaa ttcgatcatg aattattact ggcacgtctg   2340
agcatcgata caatggccaa caatttaaac atgcagaagc tatgccttta tactgaagga   2400
ttcaggatat tcttcgacat accaagtaag aaggaattgc ggaaggcaat tgcggttaaa   2460
atttctaaat ttttcaaaac attattctcc attatagcag atattctttt acaagaattt   2520
ccgtattttg atgagcaaat caccgacata gttgcttcca ttcttgacgg tacaattatc   2580
aatgagtatg gtacgaagaa acatttcaag gggagctcac cctctttatg ttcgacaacc   2640
cggtcaagat caggatctac atctcaaagt tcaatgacac cagtttctcc gctgggactg   2700
gatactgata tacgtccaat gaacaccctg tctttagttg gttcaagtac ttcaagaaat   2760
tctgacaacg ttaattcatt aaacagttca ccaaagaact tgtcttctga tccatacttg   2820
tcacatcttg tggccccaag agcacgtcat gctttaggtg ggccatctag tattataagg   2880
aataaaatac cgactacatt gacttcacct ccaggaacgg aaaaatcttc accagtacaa   2940
cgtccgcaaa cggaaagcat cagtgccaca ccaatggcca taacaaattc tactccatta   3000
tcgtcggcag cattcggaat tcgatcgcct ttgcagaaaa taagaacgag gcgttattcc   3060
gatgaaagtt taggaaaatt catgaaatca acaaataatt acattcaaga acatttgata   3120
ccaaaagatt tgaatgaagc aactcttcaa gatgctagaa gaataatgat taatattttc   3180
agtattttta agagaccgaa tagttacttc atcattcctc acaatataaa ttcgaattta   3240
```

```
caatgggttt cgcaggattt tagaaatatt atgaaaccga ttttcgtcgc catcgtaagt    3300
ccggatgtag atttacagaa tactgctcaa tcattcatgg ataccttatt atcgaatgtt    3360
attacttatg gtgaatcaga tgagaatatc agtattgaag ggtatcatct tctttgcagt    3420
tacactgtaa cattatttgc aatgggcctt ttcgatttga aaattaataa tgaaaagcgt    3480
caaattctct tggatataac tgtcaagttt atgaaggtta gatcacattt agcagggatc    3540
gcggaggcct cacaccacat ggaatacata agtgattctg aaaaactcac ctttccgctg    3600
attatgggga ctgttggtag ggccctattt gtttcattat actctagtca acaaaaaatt    3660
gaaaagactt taaatattgc ttacacagag tatctttctg caatcaattt tcatgagagg    3720
aatattgatg atgctgataa aacttgggtt cataatattg agtttgtaga agcgatgtgt    3780
catgacaact acacaacttc tggttcaatt gctttccaaa ggaggacaag aaataatatt    3840
ttacgatttg ctactattcc taacgctatc ttacttgatt ctatgaggat gatctataag    3900
aagtggcata cttacacaca cagtaaaagt ttagaaaaac aagaacggaa cgacttcaga    3960
aatttcgcgg gtatttttagc ctctttgtcg ggtatcctat tcatcaataa aaagatattg    4020
caagaaatgt atccataccct actcgacacc gtttcagaat tgaaaaaaaa tatagactct    4080
tttatctcaa aacaatgcca atggttaaac tatccggatt tattaacgag agaaaattca    4140
agagatattc taagtgtaga actgcatcct ttgtctttta acttacttttt taataatttg    4200 aggctcaagt taaaagaact tgcttgttca gacttatcaa taccgaaaaa tgaaagttcc    4260
tatgttttat tagaacaaat aatcaaaatg ctgcggacaa tcctaggtcg tgatgatgac    4320
aattatgtaa tgatgctttt ttccacagag attgtagatc ttattgattt attgacagat    4380
gaaataaaaa aaataccagc ctattgtcca aaatatctca aggcaattat tcaaatgacc    4440
aaaatgttca gtgccttgca gcactcagag gttaatttag gtgtcaaaaa tcattttcac    4500
gttaaaaata aatggttgag gcaaatcact gattggtttc aagtgagtat tgcgagagag    4560
tacgatttcg aaaacttgtc aaaacctcta aagaaatgg atttggtaaa aagagacatg    4620
gatattctat acatagatac ggcaatcgaa gcttcaaccg ctattgcgta cctcacgaga    4680
catactttct tagagattcc acctgccgcg tcagatcccg aactatctcg atctaggtct    4740
gtgatatttg ggttttattt caacatctta atgaaaggcc ttgaaaaaag tagtgatcgt    4800
gacaattacc cagtattctt gaggcacaaa atgagtgtcc tcaacgacaa tgtaatactt    4860
tcattaacaa atctttcaaa caccaatgtt gatgcgagtt tgcagttcac cttaccgatg    4920
ggctattcgg gaaatcgaaa cattaggaat gcattttttgg aggtcttcat taatatcgtt    4980
acgaactatc ggacatacac ggctaaaact gaccttggaa aattagaggc agcagacaaa    5040 ttttttgcgat atacgattga acatccccag ctatcgtcct ttggagcagc ggtttgtccc    5100
gctagcgata ttgatgctta tgctgctggc ttaataaatg catttgaaac gaggaatgcc    5160
acccacattg tagtggcaca gttgattaaa aatgaaattg aaaaatcttc cagacctacg    5220
gatatcctta agagaaatag ctgtgctacg agatcattat ctatgctagc caggtccaag    5280
ggtaacgaat atttgattcg cactttgcaa ccattactaa aaaaaattat ccagaacaga    5340
gatttttttg aaattgagaa actaaaaccg gaagattcag atgctgaacg tcaaatagag    5400
ctcttcgtta aatacatgaa tgaattattg gaatccatat ccaactccgt atcttatttt    5460 cccccctcctt tattttatat ttgccaaaac atttataaag ttgcgtgtga aaatttccg    5520 gatcacgcaa ttatcgccgc tgggtctttc gtgttttttac ggtttttttg tcctgcttta    5580
gtcagccctg attctgaaaa tatcatagat atttctcact tgagcgaaaa gcgtaccttc    5640
```

```
atcagcttgg ctaaagttat ccaaaatatt gccaatggct cagaaaattt ctccagatgg    5700
ccagctttgt gttcccaaaa ggattttctt aaagaatgta gcgatagaat tttcagattc    5760
ctagctgaac tttgtagaac agatcgcacg atagacatcc aagtgagaac agacccaacg    5820
ccaattgcat ttgactatca attccttcat tcctttgttt acctttacgg tcttgaggtg    5880
agaaggaatg tgctaaatga agcaaaacat gatgatggtg acattgatgg tgacgatttc    5940
tataagacca cattttttact tattgatgat gttcttggcc aattaggcca acctaaaatg    6000
gaattttcca atgaaatacc aatatacata agagaacata tggacgacta tccggaactg    6060
tatgagttca tgaataggca cgcgttcaga aacattgaga cttcaacagc gtacagccca    6120
agcgttcacg agtccacctc aagtgaaggc attccaatta ttacgttaac aatgtcaaat    6180
ttctcagaca gacatgtgga cattgataca gttgcttaca agttcttgca aatttatgct    6240
cgaatctgga ccaccaaaca ctgtttaata atcgactgta cagaatttga cgagggaggg    6300
cttgatatga ggaaatttat ttcttttggtt atgggactat taccagaagt tgcacccaaa    6360
aattgtatag gctgttacta cttttaacgta aacgagacat ttatggataa ttatggaaaa    6420
tgtttggaca aagacaacgt atatgtttcc tcgaaaattc ctcattattt cattaatagt    6480
aactctgatg aaggacttat gaaatctgtg ggtataactg acaagggtt gaaggttctg    6540 caagatattc gtgtctctct gcatgatatc acgctttatg acgaaaaaag aaatagattt    6600
acgccggtat cgttgaaaat aggcgatatt tactttcaag tcttgcatga aactcctagg    6660
caatataaaa taagagacat gggtacttta ttcgacgtaa aattcaatga tgtctacgaa    6720
attagccgaa tatttgaagt acatgtttcg tcaataactg gagtggcagc tgaatttaca    6780
gtaacttttc aggacgagag aaggttgatt tttagtagtc cgaaatacct tgaaattgtg    6840
aagatgttct attacgcaca gatccggtta gaaagtgaat atgaaatgga taataattcg    6900
agtacctcct ccccaaattc aaacaacaag gacaaacagc agaaagagag aacaaaatta    6960
ttgtgccacc tactgttagt atctcttatt ggtctgtttg atgagagtaa aaaaatgaaa    7020
aacagttcgt ataacctaat agctgccact gaggcgtcat ttggcttgaa ctttggctcc    7080
cattttcatc gctctcccga ggtgtacgtc cccgaatata ctacaacatt tttaggtgtt    7140
attggaaagt ctcttgcaga gtctaatcca gaactcacag cctatatgtt tatctatgtt    7200
ttggaggcat tgaagaacaa cgtaattcct cacgtttaca tccctcatac catttgcggt    7260
ttgtcttatt ggatccctaa tttataccaa catgtgtatt tggctgatga tgaagaaggc    7320
cccgaaaaca tatctcacat tttccgaatt cttatcaggc tctctgtgag agagactgac    7380
tttaaagccg tatacatgca atatgtttgg ttgctacttt tagatgatgg ccgcttaact    7440
gacattatcg ttgatgaagt tattaatcat gcgttagaaa gagactccga aaaccgcgat    7500
tggaagaaaa caatatcgtt actgactgtc ctacccacta ctgaggttgc taataacatt    7560
attcaaaaaa tattggcaaa aattagatca ttttaccgt cattgaagtt agaagctatg    7620
acccaaagtt ggtctgaact aacaatatta gttaagataa gcatccacgt ttttttttgaa    7680 acttctttgc tggtacagat gtacttacca gagatcctgt ttatcgtatc cttattaatt    7740
gatgttggtc aagggaact cagatcatca ctacaccagc tattaatgaa tgtatgccat    7800
tccttggcta ttgactcagc tttatcacaa gatcatagaa ataatctaga tgaaataagt    7860
gatatatttg cacatcaaaa ggtgaagttt atgtttgggt tcagcgagga caaaggacga    7920
attttacaga tttttagcgc ttcttctttt gcaagcaagt ttaatattct ggatttcttc    7980
```

-continued

```
atcaataata tattattgct gatggaatat tcttcaacgt acgaagcaaa cgtgtggaag    8040
acaagataca agaaatatgt cttggaatct gtgtttacaa gtaattcttt tctttcggca    8100
cgttcaatca tgattgttgg tataatgggt aaatcttaca taactgaagg gttatgcaag    8160
gctatgttaa ttgaaaccat gaaagttatc gccgaaccaa agattactga cgagcatctt    8220
ttcttagcca tatctcatat ttttacttat tccaaaattg ttgaaggttt ggatcccaac    8280
cttgacttaa tgaagcactt attttggttt tcaacactct tccttgaatc acgtcacccg    8340
ataattttt g agggtgccct tctctttgtg tcaaactgta aaggcgcct atacatggcc     8400
cagtttgaaa atgaaagcga acatcattg ataagtactt tacttaaggg gagaaagttt     8460
gctcatacct ttttaagcaa gatagagaat cttagtggta ttgtttggaa tgaagataat    8520
tttacacaca ttctgatttt catcattaat aaaggactat ccaatccttt cattaagagt    8580
acggcttttg atttcttgaa gatgatgttt agaaactcct actttgagca tcaaatcaat    8640
cagaaatctg atcattattt gtgctatatg ttcctattgt attttgtttt aaactgcaat    8700
caatttgagg aacttttagg tgacgttgat tttgaaggag aaatggttaa cattgaaaac    8760
aagaacacca ttcctaaaat tttgttagag tggttgagtt cggataacga aaatgcaaac    8820
attaccctct atcaaggtgc gatactgttc aaatgttcag ttacgatga accaagtaaa     8880
tttaggtttg cgttgattat taggcatcta ttgacaaaga aacccatttg tgcattgcgt    8940
ttttacagtg ttattcgtaa cgaaataaga aaaatatcag catttgagca aaattcggat    9000
tgtgttccac ttgctttcga tattttaaac ttattagtga cgcattcaga gtctaattcg    9060
ttagaaaaac ttcacgaaga atccattgaa cgtctaacca aaagaggttt atcgattgtg    9120
acttcttctg gtatatttgc gaagaattcc gacatgatga tacctttaga tgtaaaacct    9180
gaagatatct atgaacgtaa gagaataatg acaatgattt tatcaaggat gtcatgttct    9240
gcttag                                                               9246
```

<210> SEQ ID NO 7
<211> LENGTH: 9248
<212> TYPE: DNA
<213> ORGANISM: Saccharomyces cerevisiae

<400> SEQUENCE: 7

```
atgtcccagc ccactaagaa taagaagaaa gaacacggga ccgattccaa gtcatcccgc      60
atgactcgga cgttggttaa tcatattctt tttgaaagaa ttctcccgat ccttccggtg     120
gagtctaatc taagtaccta ttcggaagtg gaagagtatt cctcattcat ttcatgcaga    180
tctgtgctca ttaacgttac cgtttcccaa gatgcaaacg ctatggtgga aggcaccttg    240
gagttgatag aatcgcttct tcaagggcac gaaatcattt cagataagtg tagcagtgac    300
gttattgaat caatactgat tatactaaga ttgttaagtg atgcgctaga gtataattgg    360
caaaatcaag aaagccttca ttacaacgac atttcgactc acgtagaaca tgaccaagaa    420
cagaagtaca gaccaaagct taacagtatt ctgcccgact actcgtcgac tcattccaat    480
ggcaacaaac acttttttcca ccagagcaaa cctcaggcac tgataccgga actggcatcg    540
aaattgcttg agagttgcgc gaagttgaag ttcaatacaa gaactttgca aattttacaa    600
aatatgatca gtcatgttca tggaaacatt ctaacgactt tgagttcctc gattcttccc    660
cgccacaaat cctatctgac aaggcacaac catccttctc attgtaaaat gattgactct    720
actctaggcc atattctccg atttgtagcg gcttccaatc cgtccgagta ttttgaattt    780
atcagaaaga gtgtgcaagt gcccgtaaca cagacacaca cacacacacg cattcacact    840
```

```
cccattcaca ctctttgcca tcttccgttt ataacagcat agtgccccac tttgatcttt    900
tcagcttcat ctatttaagc aagcataatt ttaagaaata cttggaactc atcaaaaact    960
tatcggtgac gttaaggaaa acgatttatc attgcctact tttgcattac agcgccaaag   1020
caataatgtt ttggataatg ctaggcctg cggaatatta tgaactcttc aacttattaa   1080
aagataataa caatgaacac tcgaaatcct taaacacgtt aaaccataca cttttcgagg   1140
agatccattc gactttttaat gtgaatagca tgataaccac caatcaaaat gctcatcaag   1200
gctcatcttc cccttcgtcc tcctcgccat cgtcaccacc tagctcatca tcatcggata   1260
acaacaatca aaacataata gcaaaatcct taagtcgtca gctttctcac caccagtcat   1320
acattcaaca gcagtctgaa agaaaactac attcttcatg gactacaaac tctcaatcct   1380
ctacttcact gtcatcttca acgtctaatt caacaacaac tgatttctct actcacactc   1440
aaccaggaga atacgaccct tccttaccag atactcccac gatgtctaac atcactatta   1500
gtgcatcttc attattatct caaactccaa ctccaacaac acaattgcaa cagcggttga   1560
actcagcagc tgcagccgcc gccgcagctg cttcaccatc gaattccacc ccaactggat   1620
acacagcaga gcaacaaagt cgcgcttcat acgatgcaca caaaactggc catactggta   1680
aggattatga cgaacatttt ttgtctgtca ctcgtttgga taatgttttg gagttataca   1740
cgcactttga tgatactgag gtactaccac acacatccgt actgaagttt ttaactactt   1800
tgacaatgtt cgatattgac cttttttaatg aattaaacgc tacatcattc aaatatattc   1860
ctgattgtac tatgcatcgt ccaaaagaaa gaacaagttc tttcaataat actgcacacg   1920
agacaggttc cgaaaagact tcgggtataa acatattac acaaggctta agaaattaa   1980 cttctttacc ttcctcaacc aaaaaaactg taaaatttat gaagatgttg ctaagaaatt   2040
taaatgggaa tcaagctgta tcagatgttg ccctcttaga tacaatgagg gccttactat   2100
cattctttac aatgacttct gcggtctttc tcgtggatag aaacttaccc tcagtacttt   2160
ttgccaagag actcatcccc ataatgggga caaatttaag cgtcggtcaa gactggaatt   2220
caaaaataaa taacagtttg atggtttgtt tgaaaaaaaa ctccaccacg tttgttcaat   2280
tacaattaat attcttctct tcagctattc aattcgatca tgaattatta ctggcacgtc   2340
tgagcatcga tacaatggcc aacaatttaa acatgcagaa gctatgcctt tatactgaag   2400
gattcaggat attcttcgac ataccaagta agaaggaatt gcggaaggca attgcggtta   2460
aaatttctaa attttttcaaa acattattct ccattatagc agatattctt ttacaagaat   2520
ttccgtattt tgatgagcaa atcaccgaca tagttgcttc cattcttgac ggtacaatta   2580
tcaatgagta tggtacgaag aaacatttca aggggagctc acccctcttta tgttcgacaa   2640 cccggtcaag atcaggatct acatctcaaa gttcaatgac accagtttct ccgctgggac   2700
tggatactga tatacgtcca atgaacaccc tgtctttagt tggttcaagt acttcaagaa   2760
attctgacaa cgttaattca ttaaacagtt caccaaagaa cttgtcttct gatccatact   2820
tgtcacatct tgtggcccca agagcacgtc atgctttagg tgggccatct agtattataa   2880
ggaataaaat accgactaca ttgacttcac ctccaggaac ggaaaaatct tcaccagtac   2940
aacgtccgca aacggaaagc atcagtgcca caccaatggc cataacaaat tctactccat   3000
tatcgtcggc agcattcgga attcgatcgc ctttgcagaa aataagaacg aggcgttatt   3060
ccgatgaaag tttaggaaaa ttcatgaaat caacaaataa ttacattcaa gaacatttga   3120
taccaaaaga tttgaatgaa gcaactcttc aagatgctag aagaataatg attaatattt   3180
```

```
tcagtattتt taagagaccg aatagttact tcatcattcc tcacaatata aattcgaatt    3240
tacaatgggt ttcgcaggat tttagaaata ttatgaaacc gattttcgtc gccatcgtaa    3300
gtccggatgt agatttacag aatactgctc aatcattcat ggatacctta ttatcgaatg    3360
ttattactta tggtgaatca gatgagaata tcagtattga agggtatcat cttctttgca    3420
gttacactgt aacattattt gcaatgggcc ttttcgattt gaaaattaat aatgaaaagc    3480
gtcaaattct cttggatata actgtcaagt ttatgaaggt tagatcacat ttagcaggga    3540
tcgcggaggc ctcacaccac atggaataca taagtgattc tgaaaaactc acctttccgc    3600
tgattatggg gactgttggt agggccctat ttgtttcatt atactctagt caacaaaaaa    3660
ttgaaaagac tttaaatatt gcttacacag agtatctttc tgcaatcaat tttcatgaga    3720
ggaatattga tgatgctgat aaacttggg ttcataatat tgagtttgta aagcgatgt     3780
gtcatgacaa ctacacaact tctggttcaa ttgctttcca aaggaggaca agaaataata    3840
ttttacgatt tgctactatt cctaacgcta tcttacttga ttctatgagg atgatctata    3900
agaagtggca tacttacaca cacagtaaaa gtttagaaaa acaagaacgg aacgacttca    3960
gaaatttcgc gggtatttta gcctctttgt cgggtatcct attcatcaat aaaaagatat    4020
tgcaagaaat gtatccatac ctactcgaca ccgtttcaga attgaaaaaa aatatagact    4080
cttttatctc aaaacaatgc caatggttaa actatccgga tttattaacg agagaaaatt    4140
caagagatat tctaagtgta gaactgcatc ctttgtcttt taacttactt tttaataatt    4200
tgaggctcaa gttaaaagaa cttgcttgtt cagacttatc aataccagaa atgaaagtt    4260
cctatgtttt attagaacaa ataatcaaaa tgctgcggac aatcctaggt cgtgatgatg    4320
acaattatgt aatgatgctt tttccacag agattgtaga tcttattgat ttattgacag    4380
atgaaataaa aaaaatacca gcctattgtc caaaatatct caaggcaatt attcaaatga    4440
ccaaaatgtt cagtgccttg cagcactcag aggttaattt aggtgtcaaa atcatttc    4500
acgttaaaaa taaatggttg aggcaaatca ctgattggtt tcaagtgagt attgcgagag    4560
agtacgattt cgaaaacttg tcaaaacctc taaaagaaat ggatttggta aaaagagaca    4620
tggatatctt atacatagat acggcaatcg aagcttcaac cgctattgcg tacctcacga    4680
gacatacttt cttagagatt ccacctgccg cgtcagatcc cgaactatct cgatctaggt    4740
ctgtgatatt tgggttttat ttcaacatct taatgaaagg ccttgaaaaa agtagtgatc    4800
gtgacaatta cccagtattc ttgaggcaca aaatgagtgt cctcaacgac aatgtaatac    4860
tttcattaac aaatctttca aacaccaatg ttgatgcgag tttgcagttc accttaccga    4920
tgggctattc gggaaatcga aacattagga atgcatttt ggaggtcttc attaatatcg    4980
ttacgaacta tcggacatac acggctaaaa ctgaccttgg aaaattagag gcagcagaca    5040
aattttgcg atatacgatt gaacatcccc agctatcgtc ctttggagca gcggtttgtc    5100
ccgctagcga tattgatgct tatgctgctg gcttaataaa tgcatttgaa acgaggaatg    5160
ccacccacat tgtagtggca cagttgatta aaaatgaaat tgaaaatct tccagaccta    5220
cggatatcct tagaagaaat agctgtgcta cgagatcatt atctatgcta gccaggtcca    5280
agggtaacga atatttgatt cgcacttttgc aaccattact aaaaaaaatt atccagaaca    5340
gagattttt tgaaattgag aaactaaaac cggaagattc agatgctgaa cgtcaaatag    5400
agctcttcgt taaatacatg aatgaattat tggaatccat atccaactcc gtatcttatt    5460
ttcccccctcc tttattttat atttgccaaa acatttataa agttgcgtgt gaaaaatttc    5520
cggatcacgc aattatcgcc gctgggtctt tcgtgtttt acggttttt tgtcctgctt    5580
```

```
tagtcagccc tgattctgaa aatatcatag atatttctca cttgagcgaa aagcgtacct   5640
tcatcagctt ggctaaagtt atccaaaata ttgccaatgg ctcagaaaat ttctccagat   5700
ggccagcttt gtgttcccaa aaggattttc ttaaagaatg tagcgataga attttcagat   5760
tcctagctga actttgtaga acagatcgca cgatagacat ccaagtgaga acagacccaa   5820
cgccaattgc atttgactat caattccttc attcctttgt ttacctttac ggtcttgagg   5880
tgagaaggaa tgtgctaaat gaagcaaaac atgatgatgg tgacattgat ggtgacgatt   5940
tctataagac cacatttta cttattgatg atgttcttgg ccaattaggc caacctaaaa   6000
tggaattttc caatgaaata ccaatataca taagagaaca tatggacgac tatccggaac   6060
tgtatgagtt catgaatagg cacgcgttca gaaacattga gcttcaaca gcgtacagcc   6120 caagcgttca cgagtccacc tcaagtgaag gcattccaat tattacgtta acaatgtcaa   6180
atttctcaga cagacatgtg gacattgata cagttgctta caagttcttg caaatttatg   6240
ctcgaatctg gaccaccaaa cactgtttaa taatcgactg tacagaattt gacgagggag   6300
ggcttgatat gaggaaattt atttctttgg ttatgggact attaccagaa gttgcaccca   6360
aaaattgtat aggctgttac tactttaacg taaacgagac atttatggat aattatggaa   6420
aatgtttgga caaagacaac gtatatgttt cctcgaaaat tcctcattat ttcattaata   6480
gtaactctga tgaaggactt atgaaatctg tgggtataac tggacaaggg ttgaaggttc   6540
tgcaagatat tcgtgtctct ctgcatgata tcacgcttta tgacgaaaaa agaaatagat   6600
ttacgccggt atcgttgaaa ataggcgata tttactttca agtcttgcat gaaactccta   6660
ggcaatataa aataagagac atgggtactt tattcgacgt aaaattcaat gatgtctacg   6720
aaattagccg aatatttgaa gtacatgttt cgtcaataac tggagtggca gctgaattta   6780
cagtaacttt tcaggacgag agaaggttga tttttagtag tccgaaatac cttgaaattg   6840
tgaagatgtt ctattacgca cagatccggt tagaaagtga atatgaaatg gataataatt   6900
cgagtacctc ctccccaaat tcaaacaaca aggacaaaca gcagaaagag agaacaaaat   6960
tattgtgcca cctactgtta gtatctctta ttggtctgtt tgatgagagt aaaaaaatga   7020
aaaacagttc gtataaccta atagctgcca ctgaggcgtc atttggcttg aactttggct   7080 cccatttca tcgctctccc gaggtgtacg tccccgaata tactacaaca ttttaggtg    7140 ttattggaaa gtctcttgca gagtctaatc cagaactcac agcctatatg tttatctatg   7200
ttttggaggc attgaagaac aacgtaattc ctcacgttta catccctcat accatttgcg   7260
gtttgtctta ttggatccct aatttatacc aacatgtgta tttggctgat gatgaagaag   7320
gccccgaaaa catatctcac attttccgaa ttcttatcag gctctctgtg agagagactg   7380
actttaaagc cgtatacatg caatatgttt ggttgctact tttagatgat ggccgcttaa   7440
ctgacattat cgttgatgaa gttattaatc atgcgttaga aagagactcc gaaaaccgcg   7500
attggaagaa aacaatatcg ttactgactg tcctacccac tactgaggtt gctaataaca   7560
ttattcaaaa aatattggca aaaattagat cattttacc gtcattgaag ttagaagcta   7620
tgacccaaag ttggtctgaa ctaacaatat tagttaagat aagcatccac gtttttttg    7680 aaacttcttt gctggtacag atgtacttac cagagatcct gtttatcgta tccttattaa   7740
ttgatgttgg tccaagggaa ctcagatcat cactacacca gctattaatg aatgtatgcc   7800
attccttggc tattgactca gctttatcac aagatcatag aaataatcta gatgaaataa   7860
gtgatatatt tgcacatcaa aaggtgaagt ttatgtttgg gttcagcgag gacaaaggac   7920
```

-continued

```
gaattttaca gattttagc gcttcttctt ttgcaagcaa gtttaatatt ctggatttct    7980
tcatcaataa tatattattg ctgatggaat attcttcaac gtacgaagca aacgtgtgga    8040
agacaagata caagaaatat gtcttggaat ctgtgtttac aagtaattct tttctttcgg    8100
cacgttcaat catgattgtt ggtataatgg gtaaatctta cataactgaa gggttatgca    8160
aggctatgtt aattgaaacc atgaaagtta tcgccgaacc aaagattact gacgagcatc    8220
ttttcttagc catatctcat attttttactt attccaaaat tgttgaaggt ttggatccca    8280
accttgactt aatgaagcac ttatttggt tttcaacact cttccttgaa tcacgtcacc    8340
cgataatttt tgagggtgcc cttctctttg tgtcaaactg tataaggcgc ctatacatgg    8400
cccagtttga aaatgaaagc gaaacatcat tgataagtac tttacttaag gggagaaagt    8460
ttgctcatac cttttttaagc aagatagaga atcttagtgg tattgtttgg aatgaagata    8520
attttacaca cattctgatt tcatcatta ataaggact atccaatcct ttcattaaga     8580
gtacggcttt tgatttcttg aagatgatgt ttagaaactc ctactttgag catcaaatca    8640
atcagaaatc tgatcattat ttgtgctata tgttcctatt gtattttgtt ttaaactgca    8700
atcaatttga ggaacttta ggtgacgttg attttgaagg agaaatggtt aacattgaaa     8760
acaagaacac cattcctaaa attttgttag agtggttgag ttcggataac gaaaatgcaa    8820 acattacccct ctatcaaggt gcgatactgt tcaaatgttc agttacggat gaaccaagta   8880
aatttaggtt tgcgttgatt attaggcatc tattgacaaa gaaacccatt gtgcattgc     8940 gttttacag tgttattcgt aacgaaataa gaaaatatc agcatttgag caaaattcgg     9000
attgtgttcc acttgctttc gatattttaa acttattagt gacgcattca gagtctaatt    9060
cgttagaaaa acttcacgaa gaatccattg aacgtctaac caaaagaggt ttatcgattg    9120
tgacttcttc tggtatattt gcgaagaatt ccgacatgat gataccttta gatgtaaaac    9180
ctgaagatat ctatgaacgt aagagaataa tgacaatgat tttatcaagg atgtcatgtt    9240
ctgcttag                                                             9248
```

<210> SEQ ID NO 8
<211> LENGTH: 3081
<212> TYPE: PRT
<213> ORGANISM: Saccharomyces cerevisiae

<400> SEQUENCE: 8

```
Met Ser Gln Pro Thr Lys Asn Lys Lys Glu His Gly Thr Asp Ser
1               5                  10                  15

Lys Ser Ser Arg Met Thr Arg Thr Leu Val Asn His Ile Leu Phe Glu
            20                  25                  30

Arg Ile Leu Pro Ile Leu Pro Val Glu Ser Asn Leu Ser Thr Tyr Ser
        35                  40                  45

Glu Val Glu Glu Tyr Ser Ser Phe Ile Ser Cys Arg Ser Val Leu Ile
    50                  55                  60

Asn Val Thr Val Ser Gln Asp Ala Asn Ala Met Val Glu Gly Thr Leu
65                  70                  75                  80

Glu Leu Ile Glu Ser Leu Leu Gln Gly His Glu Ile Ile Ser Asp Lys
                85                  90                  95

Cys Ser Ser Asp Val Ile Glu Ser Ile Leu Ile Ile Leu Arg Leu Leu
            100                 105                 110

Ser Asp Ala Leu Glu Tyr Asn Trp Gln Asn Gln Glu Ser Leu His Tyr
        115                 120                 125

Asn Asp Ile Ser Thr His Val Glu His Asp Gln Glu Gln Lys Tyr Arg
```

```
            130                 135                 140
Pro Lys Leu Asn Ser Ile Leu Pro Asp Tyr Ser Ser Thr His Ser Asn
145                 150                 155                 160

Gly Asn Lys His Phe Phe His Gln Ser Lys Pro Gln Ala Leu Ile Pro
                165                 170                 175

Glu Leu Ala Ser Lys Leu Leu Glu Ser Cys Ala Lys Leu Lys Phe Asn
            180                 185                 190

Thr Arg Thr Leu Gln Ile Leu Gln Asn Met Ile Ser His Val His Gly
                195                 200                 205

Asn Ile Leu Thr Thr Leu Ser Ser Ser Ile Leu Pro Arg His Lys Ser
210                 215                 220

Tyr Leu Thr Arg His Asn His Pro Ser His Cys Lys Met Ile Asp Ser
225                 230                 235                 240

Thr Leu Gly His Ile Leu Arg Phe Val Ala Ala Ser Asn Pro Ser Glu
                245                 250                 255

Tyr Phe Glu Phe Ile Arg Lys Ser Val Gln Val Pro Val Thr Gln Thr
                260                 265                 270

His Thr His Thr His Ser His Ser His Ser His Ser Leu Pro Ser Ser
                275                 280                 285

Val Tyr Asn Ser Ile Val Pro His Phe Asp Leu Phe Ser Phe Ile Tyr
            290                 295                 300

Leu Ser Lys His Asn Phe Lys Lys Tyr Leu Glu Leu Ile Lys Asn Leu
305                 310                 315                 320

Ser Val Thr Leu Arg Lys Thr Ile Tyr His Cys Leu Leu His Tyr
                325                 330                 335

Ser Ala Lys Ala Ile Met Phe Trp Ile Met Ala Arg Pro Ala Glu Tyr
                340                 345                 350

Tyr Glu Leu Phe Asn Leu Leu Lys Asp Asn Asn Glu His Ser Lys
                355                 360                 365

Ser Leu Asn Thr Leu Asn His Thr Leu Phe Glu Glu Ile His Ser Thr
370                 375                 380

Phe Asn Val Asn Ser Met Ile Thr Thr Asn Gln Asn Ala His Gln Gly
385                 390                 395                 400

Ser Ser Ser Pro Ser Ser Ser Pro Ser Ser Pro Pro Ser Ser Ser
                405                 410                 415

Ser Ser Asp Asn Asn Gln Asn Ile Ile Ala Lys Ser Leu Ser Arg
                420                 425                 430

Gln Leu Ser His His Gln Ser Tyr Ile Gln Gln Gln Ser Glu Arg Lys
                435                 440                 445

Leu His Ser Ser Trp Thr Thr Asn Ser Gln Ser Ser Thr Ser Leu Ser
450                 455                 460

Ser Ser Thr Ser Asn Ser Thr Thr Asp Phe Ser Thr His Thr Gln
465                 470                 475                 480

Pro Gly Glu Tyr Asp Pro Ser Leu Pro Asp Thr Pro Thr Met Ser Asn
                485                 490                 495

Ile Thr Ile Ser Ala Ser Ser Leu Leu Ser Gln Thr Pro Thr Pro Thr
                500                 505                 510

Thr Gln Leu Gln Gln Arg Leu Asn Ser Ala Ala Ala Ala Ala Ala
                515                 520                 525

Ala Ala Ser Pro Ser Asn Ser Thr Pro Thr Gly Tyr Thr Ala Glu Gln
            530                 535                 540

Gln Ser Arg Ala Ser Tyr Asp Ala His Lys Thr Gly His Thr Gly Lys
545                 550                 555                 560
```

-continued

```
Asp Tyr Asp Glu His Phe Leu Ser Val Thr Arg Leu Asp Asn Val Leu
            565                 570                 575

Glu Leu Tyr Thr His Phe Asp Asp Thr Glu Val Leu Pro His Thr Ser
        580                 585                 590

Val Leu Lys Phe Leu Thr Thr Leu Thr Met Phe Asp Ile Asp Leu Phe
        595                 600                 605

Asn Glu Leu Asn Ala Thr Ser Phe Lys Tyr Ile Pro Asp Cys Thr Met
    610                 615                 620

His Arg Pro Lys Glu Arg Thr Ser Ser Phe Asn Asn Thr Ala His Glu
625                 630                 635                 640

Thr Gly Ser Glu Lys Thr Ser Gly Ile Lys His Ile Thr Gln Gly Leu
            645                 650                 655

Lys Lys Leu Thr Ser Leu Pro Ser Ser Thr Lys Lys Thr Val Lys Phe
            660                 665                 670

Met Lys Met Leu Leu Arg Asn Leu Asn Gly Asn Gln Ala Val Ser Asp
        675                 680                 685

Val Ala Leu Leu Asp Thr Met Arg Ala Leu Leu Ser Phe Phe Thr Met
        690                 695                 700

Thr Ser Ala Val Phe Leu Val Asp Arg Asn Leu Pro Ser Val Leu Phe
705                 710                 715                 720

Ala Lys Arg Leu Ile Pro Ile Met Gly Thr Asn Leu Ser Val Gly Gln
            725                 730                 735

Asp Trp Asn Ser Lys Ile Asn Asn Ser Leu Met Val Cys Leu Lys Lys
            740                 745                 750

Asn Ser Thr Thr Phe Val Gln Leu Gln Leu Ile Phe Phe Ser Ser Ala
        755                 760                 765

Ile Gln Phe Asp His Glu Leu Leu Leu Ala Arg Leu Ser Ile Asp Thr
        770                 775                 780

Met Ala Asn Asn Leu Asn Met Gln Lys Leu Cys Leu Tyr Thr Glu Gly
785                 790                 795                 800

Phe Arg Ile Phe Phe Asp Ile Pro Ser Lys Lys Glu Leu Arg Lys Ala
            805                 810                 815

Ile Ala Val Lys Ile Ser Lys Phe Phe Lys Thr Leu Phe Ser Ile Ile
            820                 825                 830

Ala Asp Ile Leu Leu Gln Glu Phe Pro Tyr Phe Asp Glu Gln Ile Thr
        835                 840                 845

Asp Ile Val Ala Ser Ile Leu Asp Gly Thr Ile Ile Asn Glu Tyr Gly
    850                 855                 860

Thr Lys Lys His Phe Lys Gly Ser Ser Pro Ser Leu Cys Ser Thr Thr
865                 870                 875                 880

Arg Ser Arg Ser Gly Ser Thr Ser Gln Ser Ser Met Thr Pro Val Ser
            885                 890                 895

Pro Leu Gly Leu Asp Thr Asp Ile Arg Pro Met Asn Thr Leu Ser Leu
            900                 905                 910

Val Gly Ser Ser Thr Ser Arg Asn Ser Asp Asn Val Asn Ser Leu Asn
        915                 920                 925

Ser Ser Pro Lys Asn Leu Ser Ser Asp Pro Tyr Leu Ser His Leu Val
    930                 935                 940

Ala Pro Arg Ala Arg His Ala Leu Gly Gly Pro Ser Ser Ile Ile Arg
945                 950                 955                 960

Asn Lys Ile Pro Thr Thr Leu Ser Pro Pro Gly Thr Glu Lys Ser
            965                 970                 975
```

```
Ser Pro Val Gln Arg Pro Gln Thr Glu Ser Ile Ser Ala Thr Pro Met
        980                 985                 990

Ala Ile Thr Asn Ser Thr Pro Leu Ser Ser Ala Ala Phe Gly Ile Arg
        995                 1000                1005

Ser Pro Leu Gln Lys Ile Arg Thr Arg Arg Tyr Ser Asp Glu Ser
    1010                1015                1020

Leu Gly Lys Phe Met Lys Ser Thr Asn Asn Tyr Ile Gln Glu His
    1025                1030                1035

Leu Ile Pro Lys Asp Leu Asn Glu Ala Thr Leu Gln Asp Ala Arg
    1040                1045                1050

Arg Ile Met Ile Asn Ile Phe Ser Ile Phe Lys Arg Pro Asn Ser
    1055                1060                1065

Tyr Phe Ile Ile Pro His Asn Ile Asn Ser Asn Leu Gln Trp Val
    1070                1075                1080

Ser Gln Asp Phe Arg Asn Ile Met Lys Pro Ile Phe Val Ala Ile
    1085                1090                1095

Val Ser Pro Asp Val Asp Leu Gln Asn Thr Ala Gln Ser Phe Met
    1100                1105                1110

Asp Thr Leu Leu Ser Asn Val Ile Thr Tyr Gly Glu Ser Asp Glu
    1115                1120                1125

Asn Ile Ser Ile Glu Gly Tyr His Leu Leu Cys Ser Tyr Thr Val
    1130                1135                1140

Thr Leu Phe Ala Met Gly Leu Phe Asp Leu Lys Ile Asn Asn Glu
    1145                1150                1155

Lys Arg Gln Ile Leu Leu Asp Ile Thr Val Lys Phe Met Lys Val
    1160                1165                1170

Arg Ser His Leu Ala Gly Ile Ala Glu Ala Ser His His Met Glu
    1175                1180                1185

Tyr Ile Ser Asp Ser Glu Lys Leu Thr Phe Pro Leu Ile Met Gly
    1190                1195                1200

Thr Val Gly Arg Ala Leu Phe Val Ser Leu Tyr Ser Ser Gln Gln
    1205                1210                1215

Lys Ile Glu Lys Thr Leu Asn Ile Ala Tyr Thr Glu Tyr Leu Ser
    1220                1225                1230

Ala Ile Asn Phe His Glu Arg Asn Ile Asp Asp Ala Asp Lys Thr
    1235                1240                1245

Trp Val His Asn Ile Glu Phe Val Glu Ala Met Cys His Asp Asn
    1250                1255                1260

Tyr Thr Thr Ser Gly Ser Ile Ala Phe Gln Arg Arg Thr Arg Asn
    1265                1270                1275

Asn Ile Leu Arg Phe Ala Thr Ile Pro Asn Ala Ile Leu Leu Asp
    1280                1285                1290

Ser Met Arg Met Ile Tyr Lys Lys Trp His Thr Tyr Thr His Ser
    1295                1300                1305

Lys Ser Leu Glu Lys Gln Glu Arg Asn Asp Phe Arg Asn Phe Ala
    1310                1315                1320

Gly Ile Leu Ala Ser Leu Ser Gly Ile Leu Phe Ile Asn Lys Lys
    1325                1330                1335

Ile Leu Gln Glu Met Tyr Pro Tyr Leu Leu Asp Thr Val Ser Glu
    1340                1345                1350

Leu Lys Lys Asn Ile Asp Ser Phe Ile Ser Lys Gln Cys Gln Trp
    1355                1360                1365

Leu Asn Tyr Pro Asp Leu Leu Thr Arg Glu Asn Ser Arg Asp Ile
```

```
                    1370                1375                1380
Leu Ser Val Glu Leu His Pro Leu Ser Phe Asn Leu Leu Phe Asn
    1385                1390                1395
Asn Leu Arg Leu Lys Leu Lys Glu Leu Ala Cys Ser Asp Leu Ser
    1400                1405                1410
Ile Pro Glu Asn Glu Ser Ser Tyr Val Leu Leu Glu Gln Ile Ile
    1415                1420                1425
Lys Met Leu Arg Thr Ile Leu Gly Arg Asp Asp Asn Tyr Val
    1430                1435                1440
Met Met Leu Phe Ser Thr Glu Ile Val Asp Leu Ile Asp Leu Leu
    1445                1450                1455
Thr Asp Glu Ile Lys Lys Ile Pro Ala Tyr Cys Pro Lys Tyr Leu
    1460                1465                1470
Lys Ala Ile Ile Gln Met Thr Lys Met Phe Ser Ala Leu Gln His
    1475                1480                1485
Ser Glu Val Asn Leu Gly Val Lys Asn His Phe His Val Lys Asn
    1490                1495                1500
Lys Trp Leu Arg Gln Ile Thr Asp Trp Phe Gln Val Ser Ile Ala
    1505                1510                1515
Arg Glu Tyr Asp Phe Glu Asn Leu Ser Lys Pro Leu Lys Glu Met
    1520                1525                1530
Asp Leu Val Lys Arg Asp Met Asp Ile Leu Tyr Ile Asp Thr Ala
    1535                1540                1545
Ile Glu Ala Ser Thr Ala Ile Ala Tyr Leu Thr Arg His Thr Phe
    1550                1555                1560
Leu Glu Ile Pro Pro Ala Ala Ser Asp Pro Glu Leu Ser Arg Ser
    1565                1570                1575
Arg Ser Val Ile Phe Gly Phe Tyr Phe Asn Ile Leu Met Lys Gly
    1580                1585                1590
Leu Glu Lys Ser Ser Asp Arg Asp Asn Tyr Pro Val Phe Leu Arg
    1595                1600                1605
His Lys Met Ser Val Leu Asn Asp Asn Val Ile Leu Ser Leu Thr
    1610                1615                1620
Asn Leu Ser Asn Thr Asn Val Asp Ala Ser Leu Gln Phe Thr Leu
    1625                1630                1635
Pro Met Gly Tyr Ser Gly Asn Arg Asn Ile Arg Asn Ala Phe Leu
    1640                1645                1650
Glu Val Phe Ile Asn Ile Val Thr Asn Tyr Arg Thr Tyr Thr Ala
    1655                1660                1665
Lys Thr Asp Leu Gly Lys Leu Glu Ala Ala Asp Lys Phe Leu Arg
    1670                1675                1680
Tyr Thr Ile Glu His Pro Gln Leu Ser Ser Phe Gly Ala Ala Val
    1685                1690                1695
Cys Pro Ala Ser Asp Ile Asp Ala Tyr Ala Ala Gly Leu Ile Asn
    1700                1705                1710
Ala Phe Glu Thr Arg Asn Ala Thr His Ile Val Val Ala Gln Leu
    1715                1720                1725
Ile Lys Asn Glu Ile Glu Lys Ser Ser Arg Pro Thr Asp Ile Leu
    1730                1735                1740
Arg Arg Asn Ser Cys Ala Thr Arg Ser Leu Ser Met Leu Ala Arg
    1745                1750                1755
Ser Lys Gly Asn Glu Tyr Leu Ile Arg Thr Leu Gln Pro Leu Leu
    1760                1765                1770
```

```
Lys Lys Ile Ile Gln Asn Arg Asp Phe Phe Glu Ile Glu Lys Leu
1775                1780                1785

Lys Pro Glu Asp Ser Asp Ala Glu Arg Gln Ile Glu Leu Phe Val
1790                1795                1800

Lys Tyr Met Asn Glu Leu Leu Glu Ser Ile Ser Asn Ser Val Ser
1805                1810                1815

Tyr Phe Pro Pro Pro Leu Phe Tyr Ile Cys Gln Asn Ile Tyr Lys
1820                1825                1830

Val Ala Cys Glu Lys Phe Pro Asp His Ala Ile Ala Ala Gly
1835                1840                1845

Ser Phe Val Phe Leu Arg Phe Phe Cys Pro Ala Leu Val Ser Pro
1850                1855                1860

Asp Ser Glu Asn Ile Ile Asp Ile Ser His Leu Ser Glu Lys Arg
1865                1870                1875

Thr Phe Ile Ser Leu Ala Lys Val Ile Gln Asn Ile Ala Asn Gly
1880                1885                1890

Ser Glu Asn Phe Ser Arg Trp Pro Ala Leu Cys Ser Gln Lys Asp
1895                1900                1905

Phe Leu Lys Glu Cys Ser Asp Arg Ile Phe Arg Phe Leu Ala Glu
1910                1915                1920

Leu Cys Arg Thr Asp Arg Thr Ile Asp Ile Gln Val Arg Thr Asp
1925                1930                1935

Pro Thr Pro Ile Ala Phe Asp Tyr Gln Phe Leu His Ser Phe Val
1940                1945                1950

Tyr Leu Tyr Gly Leu Glu Val Arg Arg Asn Val Leu Asn Glu Ala
1955                1960                1965

Lys His Asp Asp Gly Asp Ile Asp Gly Asp Asp Phe Tyr Lys Thr
1970                1975                1980

Thr Phe Leu Leu Ile Asp Asp Val Leu Gly Gln Leu Gly Gln Pro
1985                1990                1995

Lys Met Glu Phe Ser Asn Glu Ile Pro Ile Tyr Ile Arg Glu His
2000                2005                2010

Met Asp Asp Tyr Pro Glu Leu Tyr Glu Phe Met Asn Arg His Ala
2015                2020                2025

Phe Arg Asn Ile Glu Thr Ser Thr Ala Tyr Ser Pro Ser Val His
2030                2035                2040

Glu Ser Thr Ser Ser Glu Gly Ile Pro Ile Ile Thr Leu Thr Met
2045                2050                2055

Ser Asn Phe Ser Asp Arg His Val Asp Ile Asp Thr Val Ala Tyr
2060                2065                2070

Lys Phe Leu Gln Ile Tyr Ala Arg Ile Trp Thr Thr Lys His Cys
2075                2080                2085

Leu Ile Ile Asp Cys Thr Glu Phe Asp Glu Gly Gly Leu Asp Met
2090                2095                2100

Arg Lys Phe Ile Ser Leu Val Met Gly Leu Leu Pro Glu Val Ala
2105                2110                2115

Pro Lys Asn Cys Ile Gly Cys Tyr Tyr Phe Asn Val Asn Glu Thr
2120                2125                2130

Phe Met Asp Asn Tyr Gly Lys Cys Leu Asp Lys Asp Asn Val Tyr
2135                2140                2145

Val Ser Ser Lys Ile Pro His Tyr Phe Ile Asn Ser Asn Ser Asp
2150                2155                2160
```

```
Glu Gly Leu Met Lys Ser Val Gly Ile Thr Gly Gln Gly Leu Lys
    2165                2170                2175

Val Leu Gln Asp Ile Arg Val Ser Leu His Asp Ile Thr Leu Tyr
    2180                2185                2190

Asp Glu Lys Arg Asn Arg Phe Thr Pro Val Ser Leu Lys Ile Gly
    2195                2200                2205

Asp Ile Tyr Phe Gln Val Leu His Glu Thr Pro Arg Gln Tyr Lys
    2210                2215                2220

Ile Arg Asp Met Gly Thr Leu Phe Asp Val Lys Phe Asn Asp Val
    2225                2230                2235

Tyr Glu Ile Ser Arg Ile Phe Glu Val His Val Ser Ser Ile Thr
    2240                2245                2250

Gly Val Ala Ala Glu Phe Thr Val Thr Phe Gln Asp Glu Arg Arg
    2255                2260                2265

Leu Ile Phe Ser Ser Pro Lys Tyr Leu Glu Ile Val Lys Met Phe
    2270                2275                2280

Tyr Tyr Ala Gln Ile Arg Leu Glu Ser Glu Tyr Glu Met Asp Asn
    2285                2290                2295

Asn Ser Ser Thr Ser Ser Pro Asn Ser Asn Asn Lys Asp Lys Gln
    2300                2305                2310

Gln Lys Glu Arg Thr Lys Leu Leu Cys His Leu Leu Leu Val Ser
    2315                2320                2325

Leu Ile Gly Leu Phe Asp Glu Ser Lys Lys Met Lys Asn Ser Ser
    2330                2335                2340

Tyr Asn Leu Ile Ala Ala Thr Glu Ala Ser Phe Gly Leu Asn Phe
    2345                2350                2355

Gly Ser His Phe His Arg Ser Pro Glu Val Tyr Val Pro Glu Tyr
    2360                2365                2370

Thr Thr Thr Phe Leu Gly Val Ile Gly Lys Ser Leu Ala Glu Ser
    2375                2380                2385

Asn Pro Glu Leu Thr Ala Tyr Met Phe Ile Tyr Val Leu Glu Ala
    2390                2395                2400

Leu Lys Asn Asn Val Ile Pro His Val Tyr Ile Pro His Thr Ile
    2405                2410                2415

Cys Gly Leu Ser Tyr Trp Ile Pro Asn Leu Tyr Gln His Val Tyr
    2420                2425                2430

Leu Ala Asp Asp Glu Glu Gly Pro Glu Asn Ile Ser His Ile Phe
    2435                2440                2445

Arg Ile Leu Ile Arg Leu Ser Val Arg Glu Thr Asp Phe Lys Ala
    2450                2455                2460

Val Tyr Met Gln Tyr Val Trp Leu Leu Leu Leu Asp Asp Gly Arg
    2465                2470                2475

Leu Thr Asp Ile Ile Val Asp Glu Val Ile Asn His Ala Leu Glu
    2480                2485                2490

Arg Asp Ser Glu Asn Arg Asp Trp Lys Lys Thr Ile Ser Leu Leu
    2495                2500                2505

Thr Val Leu Pro Thr Thr Glu Val Ala Asn Asn Ile Ile Gln Lys
    2510                2515                2520

Ile Leu Ala Lys Ile Arg Ser Phe Leu Pro Ser Leu Lys Leu Glu
    2525                2530                2535

Ala Met Thr Gln Ser Trp Ser Glu Leu Thr Ile Leu Val Lys Ile
    2540                2545                2550

Ser Ile His Val Phe Phe Glu Thr Ser Leu Leu Val Gln Met Tyr
```

|  |  |  |  |  |  |  |  |  |  |
|---|---|---|---|---|---|---|---|---|---|
| | | 2555 | | | 2560 | | | 2565 | |
| Leu | Pro | Glu | Ile | Leu | Phe | Ile | Val | Ser | Leu | Leu | Ile | Asp | Val | Gly |
| | | 2570 | | | | 2575 | | | | 2580 | | | | |
| Pro | Arg | Glu | Leu | Arg | Ser | Ser | Leu | His | Gln | Leu | Leu | Met | Asn | Val |
| | | 2585 | | | | 2590 | | | | 2595 | | | | |
| Cys | His | Ser | Leu | Ala | Ile | Asp | Ser | Ala | Leu | Ser | Gln | Asp | His | Arg |
| | | 2600 | | | | 2605 | | | | 2610 | | | | |
| Asn | Asn | Leu | Asp | Glu | Ile | Ser | Asp | Ile | Phe | Ala | His | Gln | Lys | Val |
| | | 2615 | | | | 2620 | | | | 2625 | | | | |
| Lys | Phe | Met | Phe | Gly | Phe | Ser | Glu | Asp | Lys | Gly | Arg | Ile | Leu | Gln |
| | | 2630 | | | | 2635 | | | | 2640 | | | | |
| Ile | Phe | Ser | Ala | Ser | Ser | Phe | Ala | Ser | Lys | Phe | Asn | Ile | Leu | Asp |
| | | 2645 | | | | 2650 | | | | 2655 | | | | |
| Phe | Phe | Ile | Asn | Asn | Ile | Leu | Leu | Leu | Met | Glu | Tyr | Ser | Ser | Thr |
| | | 2660 | | | | 2665 | | | | 2670 | | | | |
| Tyr | Glu | Ala | Asn | Val | Trp | Lys | Thr | Arg | Tyr | Lys | Lys | Tyr | Val | Leu |
| | | 2675 | | | | 2680 | | | | 2685 | | | | |
| Glu | Ser | Val | Phe | Thr | Ser | Asn | Ser | Phe | Leu | Ser | Ala | Arg | Ser | Ile |
| | | 2690 | | | | 2695 | | | | 2700 | | | | |
| Met | Ile | Val | Gly | Ile | Met | Gly | Lys | Ser | Tyr | Ile | Thr | Glu | Gly | Leu |
| | | 2705 | | | | 2710 | | | | 2715 | | | | |
| Cys | Lys | Ala | Met | Leu | Ile | Glu | Thr | Met | Lys | Val | Ile | Ala | Glu | Pro |
| | | 2720 | | | | 2725 | | | | 2730 | | | | |
| Lys | Ile | Thr | Asp | Glu | His | Leu | Phe | Leu | Ala | Ile | Ser | His | Ile | Phe |
| | | 2735 | | | | 2740 | | | | 2745 | | | | |
| Thr | Tyr | Ser | Lys | Ile | Val | Glu | Gly | Leu | Asp | Pro | Asn | Leu | Asp | Leu |
| | | 2750 | | | | 2755 | | | | 2760 | | | | |
| Met | Lys | His | Leu | Phe | Trp | Phe | Ser | Thr | Leu | Phe | Leu | Glu | Ser | Arg |
| | | 2765 | | | | 2770 | | | | 2775 | | | | |
| His | Pro | Ile | Ile | Phe | Glu | Gly | Ala | Leu | Leu | Phe | Val | Ser | Asn | Cys |
| | | 2780 | | | | 2785 | | | | 2790 | | | | |
| Ile | Arg | Arg | Leu | Tyr | Met | Ala | Gln | Phe | Glu | Asn | Glu | Ser | Glu | Thr |
| | | 2795 | | | | 2800 | | | | 2805 | | | | |
| Ser | Leu | Ile | Ser | Thr | Leu | Leu | Lys | Gly | Arg | Lys | Phe | Ala | His | Thr |
| | | 2810 | | | | 2815 | | | | 2820 | | | | |
| Phe | Leu | Ser | Lys | Ile | Glu | Asn | Leu | Ser | Gly | Ile | Val | Trp | Asn | Glu |
| | | 2825 | | | | 2830 | | | | 2835 | | | | |
| Asp | Asn | Phe | Thr | His | Ile | Leu | Ile | Phe | Ile | Ile | Asn | Lys | Gly | Leu |
| | | 2840 | | | | 2845 | | | | 2850 | | | | |
| Ser | Asn | Pro | Phe | Ile | Lys | Ser | Thr | Ala | Phe | Asp | Phe | Leu | Lys | Met |
| | | 2855 | | | | 2860 | | | | 2865 | | | | |
| Met | Phe | Arg | Asn | Ser | Tyr | Phe | Glu | His | Gln | Ile | Asn | Gln | Lys | Ser |
| | | 2870 | | | | 2875 | | | | 2880 | | | | |
| Asp | His | Tyr | Leu | Cys | Tyr | Met | Phe | Leu | Leu | Tyr | Phe | Val | Leu | Asn |
| | | 2885 | | | | 2890 | | | | 2895 | | | | |
| Cys | Asn | Gln | Phe | Glu | Glu | Leu | Leu | Gly | Asp | Val | Asp | Phe | Glu | Gly |
| | | 2900 | | | | 2905 | | | | 2910 | | | | |
| Glu | Met | Val | Asn | Ile | Glu | Asn | Lys | Asn | Thr | Ile | Pro | Lys | Ile | Leu |
| | | 2915 | | | | 2920 | | | | 2925 | | | | |
| Leu | Glu | Trp | Leu | Ser | Ser | Asp | Asn | Glu | Asn | Ala | Asn | Ile | Thr | Leu |
| | | 2930 | | | | 2935 | | | | 2940 | | | | |
| Tyr | Gln | Gly | Ala | Ile | Leu | Phe | Lys | Cys | Ser | Val | Thr | Asp | Glu | Pro |
| | | 2945 | | | | 2950 | | | | 2955 | | | | |

```
Ser Lys Phe Arg Phe Ala Leu Ile Ile Arg His Leu Leu Thr Lys
    2960                2965                2970

Lys Pro Ile Cys Ala Leu Arg Phe Tyr Ser Val Ile Arg Asn Glu
    2975                2980                2985

Ile Arg Lys Ile Ser Ala Phe Glu Gln Asn Ser Asp Cys Val Pro
    2990                2995                3000

Leu Ala Phe Asp Ile Leu Asn Leu Leu Val Thr His Ser Glu Ser
    3005                3010                3015

Asn Ser Leu Glu Lys Leu His Glu Glu Ser Ile Glu Arg Leu Thr
    3020                3025                3030

Lys Arg Gly Leu Ser Ile Val Thr Ser Ser Gly Ile Phe Ala Lys
    3035                3040                3045

Asn Ser Asp Met Met Ile Pro Leu Asp Val Lys Pro Glu Asp Ile
    3050                3055                3060

Tyr Glu Arg Lys Arg Ile Met Thr Met Ile Leu Ser Arg Met Ser
    3065                3070                3075

Cys Ser Ala
    3080

<210> SEQ ID NO 9
<211> LENGTH: 293
<212> TYPE: PRT
<213> ORGANISM: Saccharomyces cerevisiae

<400> SEQUENCE: 9

Met Ser Gln Pro Thr Lys Asn Lys Lys Glu His Gly Thr Asp Ser
1               5                   10                  15

Lys Ser Ser Arg Met Thr Arg Thr Leu Val Asn His Ile Leu Phe Glu
            20                  25                  30

Arg Ile Leu Pro Ile Leu Pro Val Glu Ser Asn Leu Ser Thr Tyr Ser
                35                  40                  45

Glu Val Glu Glu Tyr Ser Ser Phe Ile Ser Cys Arg Ser Val Leu Ile
    50                  55                  60

Asn Val Thr Val Ser Gln Asp Ala Asn Ala Met Val Glu Gly Thr Leu
65                  70                  75                  80

Glu Leu Ile Glu Ser Leu Leu Gln Gly His Glu Ile Ile Ser Asp Lys
                85                  90                  95

Cys Ser Ser Asp Val Ile Glu Ser Ile Leu Ile Ile Leu Arg Leu Leu
                100                 105                 110

Ser Asp Ala Leu Glu Tyr Asn Trp Gln Asn Gln Glu Ser Leu His Tyr
            115                 120                 125

Asn Asp Ile Ser Thr His Val Glu His Asp Gln Glu Gln Lys Tyr Arg
    130                 135                 140

Pro Lys Leu Asn Ser Ile Leu Pro Asp Tyr Ser Ser Thr His Ser Asn
145                 150                 155                 160

Gly Asn Lys His Phe His Gln Ser Lys Pro Gln Ala Leu Ile Pro
                165                 170                 175

Glu Leu Ala Ser Lys Leu Leu Glu Ser Cys Ala Lys Leu Lys Phe Asn
            180                 185                 190

Thr Arg Thr Leu Gln Ile Leu Gln Asn Met Ile Ser His Val His Gly
            195                 200                 205

Asn Ile Leu Thr Thr Leu Ser Ser Ser Ile Leu Pro Arg His Lys Ser
    210                 215                 220

Tyr Leu Thr Arg His Asn His Pro Ser His Cys Lys Met Ile Asp Ser
```

```
                225                 230                 235                 240

Thr Leu Gly His Ile Leu Arg Phe Val Ala Ala Ser Asn Pro Ser Glu
                        245                 250                 255

Tyr Phe Glu Phe Ile Arg Lys Ser Val Gln Val Pro Val Thr Gln Thr
                        260                 265                 270

His Thr His Thr Arg Ile His Thr Pro Ile His Thr Leu Cys His Leu
                        275                 280                 285

Pro Phe Ile Thr Ala
                        290

<210> SEQ ID NO 10
<211> LENGTH: 309
<212> TYPE: PRT
<213> ORGANISM: Saccharomyces cerevisiae

<400> SEQUENCE: 10

Met Gln Gly Asn Lys Ser Thr Ile Arg Glu Tyr Lys Ile Val Val
        1               5                   10                  15

Gly Gly Gly Gly Val Gly Lys Ser Ala Leu Thr Ile Gln Phe Ile Gln
                        20                  25                  30

Ser Tyr Phe Val Asp Glu Tyr Asp Pro Thr Ile Glu Asp Ser Tyr Arg
                        35                  40                  45

Lys Gln Val Val Ile Asp Asp Lys Val Ser Ile Leu Asp Ile Leu Asp
                        50                  55                  60

Thr Ala Gly Gln Glu Glu Tyr Ser Ala Met Arg Glu Gln Tyr Met Arg
        65                      70                  75                  80

Thr Gly Glu Gly Phe Leu Leu Val Tyr Ser Val Thr Ser Arg Asn Ser
                        85                  90                  95

Phe Asp Glu Leu Leu Ser Tyr Tyr Gln Gln Ile Gln Arg Val Lys Asp
                        100                 105                 110

Ser Asp Tyr Ile Pro Val Val Val Gly Asn Lys Leu Asp Leu Glu
                        115                 120                 125

Asn Glu Arg Gln Val Ser Tyr Glu Asp Gly Leu Arg Leu Ala Lys Gln
                        130                 135                 140

Leu Asn Ala Pro Phe Leu Glu Thr Ser Ala Lys Gln Ala Ile Asn Val
        145                     150                 155                 160

Asp Glu Ala Phe Tyr Ser Leu Ile Arg Leu Val Arg Asp Asp Gly Gly
                        165                 170                 175

Lys Tyr Asn Ser Met Asn Arg Gln Leu Asp Asn Thr Asn Glu Ile Arg
                        180                 185                 190

Asp Ser Glu Leu Thr Ser Ser Ala Thr Ala Asp Arg Glu Lys Lys Asn
                        195                 200                 205

Asn Gly Ser Tyr Val Leu Asp Asn Ser Leu Thr Asn Ala Gly Thr Gly
                        210                 215                 220

Ser Ser Ser Lys Ser Ala Val Asn His Asn Gly Glu Thr Thr Lys Arg
        225                     230                 235                 240

Thr Asp Glu Lys Asn Tyr Val Asn Gln Asn Asn Asn Glu Gly Asn
                        245                 250                 255

Thr Lys Tyr Ser Ser Asn Gly Asn Gly Asn Arg Ser Asp Ile Ser Arg
                        260                 265                 270

Gly Asn Gln Asn Asn Ala Leu Asn Ser Arg Ser Lys Gln Ser Ala Glu
                        275                 280                 285

Pro Gln Lys Asn Ser Ser Ala Asn Ala Arg Lys Glu Ser Gly Gly
                        290                 295                 300
```

```
Cys Cys Ile Ile Cys
305

<210> SEQ ID NO 11
<211> LENGTH: 309
<212> TYPE: PRT
<213> ORGANISM: Saccharomyces cerevisiae

<400> SEQUENCE: 11

Met Gln Gly Asn Lys Ser Thr Ile Arg Glu Tyr Lys Ile Val Val
1               5                   10                  15

Gly Gly Gly Gly Val Gly Lys Ser Ala Leu Thr Ile Gln Phe Ile Gln
                20                  25                  30

Ser Tyr Phe Val Asp Glu Tyr Asp Pro Thr Ile Glu Asp Ser Tyr Arg
            35                  40                  45

Lys Gln Val Val Ile Asp Asp Lys Val Ser Ile Leu Asp Ile Leu Asp
50                  55                  60

Thr Thr Gly Gln Glu Glu Tyr Ser Ala Met Arg Glu Gln Tyr Met Arg
65                  70                  75                  80

Thr Gly Glu Gly Phe Leu Leu Val Tyr Ser Val Thr Ser Arg Asn Ser
                85                  90                  95

Phe Asp Glu Leu Leu Ser Tyr Tyr Gln Ile Gln Arg Val Lys Asp
                100                 105                 110

Ser Asp Tyr Ile Pro Val Val Val Gly Asn Lys Leu Asp Leu Glu
            115                 120                 125

Asn Glu Arg Gln Val Ser Tyr Glu Asp Gly Leu Arg Leu Ala Lys Gln
            130                 135                 140

Leu Asn Ala Pro Phe Leu Glu Thr Ser Ala Lys Gln Ala Ile Asn Val
145                 150                 155                 160

Asp Glu Ala Phe Tyr Ser Leu Ile Arg Leu Val Arg Asp Gly Gly
                165                 170                 175

Lys Tyr Asn Ser Met Asn Arg Gln Leu Asp Asn Thr Asn Glu Ile Arg
            180                 185                 190

Asp Ser Glu Leu Thr Ser Ser Ala Thr Ala Asp Arg Glu Lys Lys Asn
            195                 200                 205

Asn Gly Ser Tyr Val Leu Asp Asn Ser Leu Thr Asn Ala Gly Thr Gly
            210                 215                 220

Ser Ser Ser Lys Ser Ala Val Asn His Asn Gly Glu Thr Thr Lys Arg
225                 230                 235                 240

Thr Asp Glu Lys Asn Tyr Val Asn Gln Asn Asn Asn Asn Glu Gly Asn
                245                 250                 255

Thr Lys Tyr Ser Ser Asn Gly Asn Gly Asn Arg Ser Asp Ile Ser Arg
            260                 265                 270

Gly Asn Gln Asn Asn Ala Leu Asn Ser Arg Ser Lys Gln Ser Ala Glu
            275                 280                 285

Pro Gln Lys Asn Ser Ser Ala Asn Ala Arg Lys Glu Ser Ser Gly Gly
            290                 295                 300

Cys Cys Ile Ile Cys
305
```

US 11,667,680 B2

REGULATION OF THE RAS/CAMP/PKA SIGNALING PATHWAY IN YEASTS FOR OBTAINING A FERMENTATION PRODUCT DURING FERMENTATION

STATEMENT REGARDING SEQUENCE LISTING

The Sequence Listing associated with this application is provided in text format in lieu of a paper copy, and is hereby incorporated by reference into the specification. The name of the text file containing the Sequence Listing is 580127_403USPC_SEQUENCE_LISTING.txt. The text file is 68.4 KB, was created on Sep. 15, 2018, and is being submitted electronically via EFS-Web.

TECHNOLOGICAL FIELD

This disclosure relates to the selection of yeast cells as well as the genetic engineering of recombinant yeast host cells to increase their fermentation efficiency while maintaining their propagation efficiency.

BACKGROUND

During the course of aerobic, glucose-limited, fed batch yeast production, the propagated yeasts must preferably maintain the same (or better) desirable qualities that are present in the initial inoculum. In the production of fuel ethanol with recombinant yeasts, several strains were identified which have undesirable phenotypes (poor ethanol tolerance, high residual sugar) following yeast propagation.

It would be highly desirable to be provided with a yeast strain exhibiting improved ability to ferment a medium while maintaining its propagation efficiency at high cell density.

BRIEF SUMMARY

The present disclosure relates to yeast cells having either been selected based on or genetically engineered to exhibit an increase signaling activity in their RAS/cAMP/PKA pathway. In some embodiments, these yeast cells express a mutated Ras1 protein and/or a mutated Ras2 protein having increased activity when compared to the corresponding wild-type Ras proteins. In other embodiments, these yeast cells express a mutated Ira1 protein and/or a mutated Ira2 protein having decreased inhibitory activity against the wild-type Ras1 or the wild-type Ira proteins. These differences in expression/activity are preferably observed during the fermentation of the yeasts.

According to a first aspect, the present disclosure provides a method of fermenting a fermentation medium to obtain a fermentation product. Broadly, the method comprises (i) optionally propagating a first yeast cell and/or a second recombinant yeast host cell in a propagation medium to obtain a propagated population of yeast cells; and (ii) contacting the first yeast cell, the second recombinant yeast host cell and/or the propagated population with the fermentation medium under conditions to allow the generation of the fermentation product. In the method, the first yeast cell has been selected as being capable of exhibiting increased signaling in a RAS/cAMP/PKA pathway (and in some embodiments, this feature is observed during fermentation but not during propagation). In addition, the second recombinant yeast host cell comprises an heterologous nucleic acid molecule coding for an heterologous protein capable of increasing signaling in the RAS/cAMP/PKA pathway (and in some embodiments, this feature is observed during fermentation but not during propagation). Further, the propagated population comprises at least one of the first yeast cell or the second recombinant yeast host cell. In an embodiment, the method comprising contacting the first yeast cell or the propagated population comprising the first yeast cell with the propagation medium. In another embodiment, the method further comprises, prior to or during the propagating step and/or the contacting step, selecting the first yeast cell from a population of yeast cells. In still another embodiment, the method further comprises, prior to or during the propagating step and/or the contacting step, excluding or removing a yeast cell lacking the ability to exhibit increased signaling in the RAS/cAMP/PKA pathway from the propagation medium and/or the fermentation medium. In another embodiment, the first yeast cell is or has been selected as being capable of expressing a mutated Ras2 protein having increased activity when compared to a wild-type Ras2 protein. In another embodiment, the mutated Ras2 protein includes at least one amino acid residue variation when compared to the wild-type Ras2 protein. In still another embodiment, the mutated Ras2 protein has the amino acid sequence of SEQ ID NO: 2 or is encoded by a nucleic acid molecule having sequence of SEQ ID NO: 3. In another embodiment, the first yeast cell is or has been selected as being capable of expressing a mutated Ira2 protein having a reduced inhibitory activity towards a wild-type Ras1 protein and/a wild-type Ras2 protein when compared to a wild-type Ira2 protein. In another embodiment, the mutated Ira2 protein is a fragment of the wild-type Ira2 protein. In still another embodiment, the mutated Ira2 protein has the amino acid sequence of SEQ ID NO: 9 or is encoded by a nucleic acid molecule having the sequence of SEQ ID NO: 7. In an embodiment, the method comprises contacting the second recombinant yeast host cell or the propagated population comprising the second recombinant yeast host cell with the propagation medium. In still another embodiment, the heterologous nucleic acid molecule comprises a first nucleic acid coding for a mutated Ras2 protein having increased activity when compared to a wild-type Ras2 protein. In yet another embodiment, the mutated Ras2 protein includes at least one amino acid residue variation when compared to the wild-type Ras2 protein and, in still a further embodiment, has the amino acid sequence of SEQ ID NO: 2 or is encoded by a nucleic acid molecule having the sequence of SEQ ID NO: 3. In still another embodiment, the heterologous nucleic acid molecule comprises a second nucleic acid molecule coding for a mutated Ira2 protein having a reduced inhibitory activity towards a wild-type Ras1 protein and/or a wild-type Ras2 protein when compared to a wild-type Ira2 protein. For example, the mutated Ira2 protein can be a fragment of the wild-type Ira2 protein and/or have the amino acid sequence of SEQ ID NO: 9 or is encoded by a nucleic acid molecule having the sequence of SEQ ID NO: 7. In an embodiment, the heterologous nucleic acid molecule further comprises a promoter operatively linked to the first nucleic acid molecule and/or the second nucleic acid molecule and the promoters is capable of increasing the expression of the first nucleic acid molecule and/or the second nucleic acid molecule during fermentation, when compared to the expression of the first nucleic acid molecule and/or the second nucleic acid molecule during propagation. In some embodiments, the promoter is not a RAS2 promoter from a RAS2 gene or a RAS1 promoter from a RAS1 gene. In a further embodiment, the promoter is capable of increasing the expression of the first nucleic acid molecule and/or the second nucleic acid molecule when the second recombinant yeast host cell is in at least partial anaerobic conditions when compared to the level of expression of the first nucleic acid molecule and/or the second nucleic acid molecule obtained when the second recombinant yeast host cell placed in aerobic conditions (for example, the promoter can be a DAN1 promoter from a DAN1 gene or a ANB1 promoter from a ANB1 gene). In still another embodiment, the promoter is a glucose-repressible promoter (for example, the promoter can be a HXK1 promoter from a HXK1 gene). In still another embodiment, the first yeast cell and/or the second recombinant yeast host cell comprises at least one copy a RAS2 gene coding for a wild-type Ras2 protein. In an embodiment, the first yeast cell or the second recombinant yeast host cell is capable of utilizing xylose and/or arabinose. In an embodiment, the fermentation product is ethanol. In another embodiment, the first yeast cell and/or the second recombinant yeast host cell is from the genus *Saccharomyces, Kluyveromyces, Arxula, Debaryomyces, Candida, Pichia, Phaffia, Schizosaccharomyces, Hansenula, Kloeckera, Schwanniomyces* or *Yarrowia*. In an embodiment, the first yeast cell and/or the second recombinant yeast host cell is from the genus *Saccharomyces* and, in a further embodiment, can be from the species *Saccharomyces cerevisiae*.

According to a second aspect, the present disclosure provides a recombinant yeast host cell comprising a first heterologous nucleic acid molecule having a promoter intended to be operatively linked to a first nucleic acid molecule coding for a mutated Ras2 protein. In such recombinant yeast host cell, the promoter can be operatively linked to the first nucleic acid molecule. In the recombinant yeast host cell, and the promoters is capable of increasing the expression of the first nucleic acid molecule and/or the second nucleic acid molecule during fermentation, when compared to the expression of the first nucleic acid molecule and/or the second nucleic acid molecule during propagation. Still in the recombinant yeast host cell, the mutated Ras2 protein exhibits increased activity when compared to the corresponding wild-type Ras2 protein. In an embodiment, the recombinant yeast host cell further comprises at least one copy of a RAS2 gene coding for the wild-type Ras2 protein under the control of the RAS2 promoter. In still another embodiment, the first heterologous nucleic acid molecule further comprises the first nucleic acid molecule. In another embodiment, the promoter is not a RAS2 promoter from a RAS2 gene. In still another embodiment, the promoter is capable of increasing the expression of the first nucleic acid molecule when the recombinant yeast host cell is in at least partial anaerobic conditions when compared to the level of expression of the first nucleic acid molecule obtained when the recombinant yeast host cell placed in aerobic conditions (for example, the promoter can be a DAN1 promoter from a DAN1 gene or a ANB1 promoter from a ANB1 gene). In yet another embodiment, the promoter is glucose-repressible (for example, the promoter can be a HXK1 promoter from a HXK1 gene). In some embodiments, the wild-type Ras2 protein has the amino acid of SEQ ID NO: 1. In another embodiment, the mutated Ras2 protein has at least one amino acid substitution when compared to the wild-type Ras2 protein and, in a further embodiment, can have the amino acid sequence of SEQ ID NO: 2 or be encoded by a nucleic acid molecule having the sequence of SEQ ID NO: 3. In another embodiment, the recombinant yeast host cell can comprise a second heterologous nucleic acid molecule comprising the promoter intended to be operatively linked to a second nucleic acid molecule coding for a mutated Ira2 protein having a reduced inhibitory activity towards a wild-type Ras2 protein when compared to a wild-type Ira2 protein. In an embodiment, the mutated Ira2 protein is a fragment of the wild-type Ira2 protein and, in a further embodiment, have the amino acid sequence of SEQ ID NO: 9 or be encoded by a nucleic acid molecule having the sequence of SEQ ID NO: 7. In an embodiment, the second heterologous nucleic acid molecule comprises the second nucleic acid molecule. In yet another embodiment, the recombinant yeast host cell is capable of utilizing xylose and/or arabinose. In still a further embodiment, the recombinant yeast host cell can comprise a third heterologous nucleic acid encoding an heterologous xylose isomerase. In still another embodiment, the recombinant yeast host cell can be from the genus *Saccharomyces, Kluyveromyces, Arxula, Debaryomyces, Candida, Pichia, Phaffia, Schizosaccharomyces, Hansenula, Kloeckera, Schwanniomyces* or *Yarrowia*, for example from the genus *Saccharomyces*. In still another embodiment, the recombinant yeast host cell can be from the species *Saccharomyces cerevisiae*.

According to a third aspect, the present disclosure provides a method of propagating a yeast cell in a propagating medium, said method comprising contacting the recombinant yeast host cell described herein with the propagation medium under conditions to allow the propagation of the recombinant yeast host cell. In an embodiment, the propagation medium comprises molasses.

According to a fourth aspect, the present disclosure provides a method of fermenting a fermentation medium to obtain a fermentation product. The method comprises (i) optionally propagating the recombinant yeast host cell described herein to obtain a propagated population of recombinant yeast host cells; and (ii) contacting the recombinant yeast host cell and/or the propagated population with the fermentation medium under conditions to allow the generation of the fermentation product. In an embodiment, the fermentation medium comprises lignocellulosic material, xylose, arabinose and/or maltose. In another embodiment, the fermentation product is ethanol. In still another embodiment, the propagation medium comprises molasses.

BRIEF DESCRIPTION OF THE DRAWINGS

Having thus generally described the nature of the invention, reference will now be made to the accompanying drawings, showing by way of illustration, a preferred embodiment thereof, and in which.

DETAILED DESCRIPTION

Figure 1:
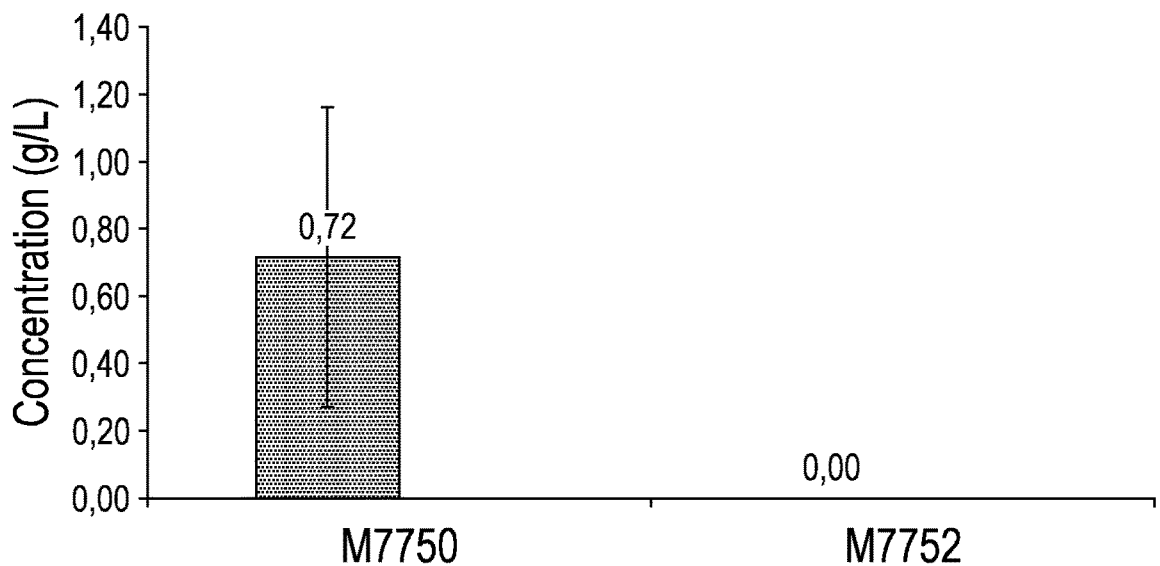
FIG. 1 illustrates glucose consumption during fermentation of a glucose/maltose medium in function of yeast strain used. Results are shown as the concentration of residual glucose (in g/L) in media fermented for 1.5 hours (gray bars) or 4 hours (white bars) for the various *Saccharomyces cerevisiae* strains tested (M7750 or M7752).

In accordance with the present disclosure, there are provided yeast cells having an increased signaling activity in the RAS/cAMP/PKA pathway during fermentation. In some embodiments, this increase in signaling activity is limited to fermentation (e.g., for example, in anaerobic conditions) and is not observed during propagation (e.g., for example, in glucose-limited aerobic conditions). The yeast cells can be selected (based on their ability to exhibit increasing signaling activity in the RAS/cAMP/PKA pathway) from a population of yeast cells and, in a further embodiment, can be naturally-occurring. The yeast cells can include one or more genetic modification(s) to increase their signaling activity in the RAS/cAMP/PKA pathway.

Yeast Strains Having Increased Signaling Activity in the RAS/cAMP/PKA Pathway

The present disclosure provides yeast cells having increased signaling activity in the RAS/cAMP/PKA pathway during fermentation. As used in the context of the present disclosure a yeast cell or strain having "increased signaling activity in the RAS/cAMP/PKA pathway" exhibits an increase in biological activity in one or more protein in the RAS/cAMP/PKA pathway ultimately causing an increase the production of cAMP, when compared to a corresponding control yeast cell. As it is known in the art, the increase in cAMP caused by this biological pathway causes the dissociation of the Pka protein into the Bcy1 protein and the Tpk1-3 protein. The dissociated Tpk1-3 protein then favors fermentation and trehalose mobilization. This increase in RAS/cAMP/PKA signaling is preferably observed during fermentation (e.g., for example, in anaerobic conditions) and, in some embodiments, is not observed during propagation (e.g., for example, in glucose-limited aerobic conditions).

In order to achieve such increase in RAS/cAMP/PKA signaling, the expression and/or activity of one or more protein of the RAS/cAMP/PKA pathway can be increased (when compared to a corresponding control yeast cell or strain). The one or more proteins whose expression or biological activity can be increased include, but are not limited to a Cdc25 protein (a membrane bound guanine nucleotide exchange factor capable of activating a Ras1 protein and/or a Ras2 protein), a Sdc25 protein (a Ras guanine nucleotide exchange factor capable of activating the Ras1 protein and/or the Ras2 protein), a Ras1 protein (GTPase whose activity increase the activity of the Cyr1 protein) and/or a Ras2 protein (a GTPase whose activity increases the activity of the Cyr1).

In an embodiment, the Ras2 protein expression or its biological activity is increased to cause an increase in the signaling activity of the RAS/cAMP/PKA pathway. In such embodiment, the yeast cell can express a mutation in the Ras2 protein (herein referred to as a mutated Ras2 protein) which increases its biological activity. For example, the mutated Ras2 protein can be a variant or a fragment of the wild-type Ras2 protein resulting in an increase in the biological activity of the Ras2 protein. The Ras2 protein is a GTPase and as such its biological activity includes binding to GTP and hydrolyzing GTP into GDP. As such, in the context of the present disclosure, a mutated Ras2 protein having increased (biological) activity can exhibit a higher binding affinity for GTP, a higher GTP hydrolyzing activity or both, when compared to the wild-type Ras2 protein. In an embodiment, the mutated Ras2 protein can have one or more amino acid substitutions. For example, the mutated Ras2 protein can have an amino acid substitution at a residue corresponding to location 66 of SEQ ID NO: 1 (or a corresponding residue in another wild-type Ras2 protein). In an embodiment, the amino acid substitution of the mutated Ras2 protein is limited to the residue located at position 66 of SEQ ID NO: 1 (or a corresponding residue in another wild-type Ras2 protein). In the wild-type Ras2 protein of *S. cerevisiae* (SEQ ID NO: 1), the amino acid residue at location 66 is an alanine residue. In an embodiment, the mutated Ras2 protein does not have an alanine residue located at position 66 of SEQ ID NO: 1 (or at a corresponding position in another wild-type Ras2 protein), but instead has an histidine, an isoleucine, an arginine, a leucine, an asparagine, a lysine, an aspartic acid, a methionine, a cysteine, a phenylalanine, a glutamic acid, a threonine, a glutamine, a tryptophan, a glycine, a valine, a proline, a serine or a tyrosine residue. In an embodiment, the mutated Ras2 protein has, at position 66 of SEQ ID NO: 1 (or at a corresponding position in another wild-type Ras2 protein) does not have an aliphatic amino acid residue, such as, for example, a glycine, a valine, a leucine or an isoleucine residue. In still another embodiment, the mutated Ras2 protein has, at position 66 of SEQ ID NO: 1 (or at a corresponding position in another wild-type Ras2 protein) a hydroxyl or sulfur/selenium-containing amino acid, such as, for example, a serine, a cysteine, a threonine or a methionine residue. In yet another embodiment, the mutated Ras2 protein has, at position 66 of SEQ ID NO: 1 (or at a corresponding position in another wild-type Ras2 protein) a threonine residue. In still a further embodiment, the mutated Ras2 protein has the amino acid sequence of SEQ ID NO: 2 and can be encoded by a nucleic acid molecule having a nucleic acid molecule having the sequence of SEQ ID NO: 3 or of SEQ ID NO: 5.

In an embodiment, the Ras1 protein expression or biological activity is increased to cause an increase in the signaling activity of the RAS/cAMP/PKA pathway. In such embodiment, the yeast cell can express a mutation in the Ras1 protein (herein referred to as a mutated Ras1 protein) which increases its biological activity. For example, the mutated Ras1 protein can be a variant or a fragment of the wild-type Ras1 protein resulting in an increase in the biological activity of the Ras1 protein. The Ras1 protein is a GTPase and as such its biological activity include binding to GTP and hydrolyzing GTP into GDP. As such, in the context of the present disclosure, a mutated Ras1 protein having increased (biological) activity can exhibit a higher binding affinity for GTP, a higher GTP hydrolyzing activity or both, when compared to the wild-type Ras1 protein. In an embodiment, the mutated Ras1 protein can have an amino acid substitution. For example, the mutated Ras1 protein can have an amino acid substitution at a residue corresponding to location 66 of SEQ ID NO: 10 (or at a corresponding residue in another wild-type Ras1 protein) as described in Temeles et al., 1985. In an embodiment, the amino acid substitution of the mutated Ras1 protein is limited to the residue located at position 66 of SEQ ID NO: 10 (or a corresponding residue in another wild-type Ras1 protein). In the wild-type Ras1 protein of S. cerevisiae (SEQ ID NO: 10), the amino acid residue at location 66 is an alanine residue. In an embodiment, the mutated Ras1 protein does not have an alanine residue located at position 66 of SEQ ID NO: 10 (or at a corresponding position in another wild-type Ras1 protein), but instead has an histidine, an isoleucine, an arginine, a leucine, an asparagine, a lysine, an aspartic acid, a methionine, a cysteine, a phenylalanine, a glutamic acid, a threonine, a glutamine, a tryptophan, a glycine, a valine, a proline, a serine or a tyrosine residue. In an embodiment, the mutated Ras1 protein has, at position 66 of SEQ ID NO: 10 (or at a corresponding position in another wild-type Ras1 protein) does not have an aliphatic amino acid residue, such as, for example, a glycine, a valine, a leucine or an isoleucine residue. In still another embodiment, the mutated Ras1 protein has, at position 66 of SEQ ID NO: 1 (or at a corresponding position in another wild-type Ras1 protein) a hydroxyl or sulfur/selenium-containing amino acid, such as, for example, a serine, a cysteine, a threonine or a methionine residue. In yet another embodiment, the mutated Ras1 protein has, at position 66 of SEQ ID NO: 1 (or at a corresponding position in another wild-type Ras1 protein) a threonine residue. In still a further embodiment, the mutated Ras1 protein has the amino acid sequence of SEQ ID NO: 11.

In another example, the expression and/or activity of one or more protein of the RAS/cAMP/PKA pathway can be decreased (when compared to a corresponding control yeast cell or strain) to achieve an increase in the signaling activity RAS/cAMP/PKA pathway. The one or more protein whose expression or biological activity can be decreased include, but is not limited to, a Ira1 protein (a GTPase-activating protein whose activity decreases the activity of the wild-type Ras1 protein and/or the wild-type Ras2 protein) and/or an Ira2 protein (a GTPase-activating protein whose activity decreases the activity of the wild-type Ras1 protein and/or the wild-type Ras2 protein).

As indicated above, in an embodiment, the expression and/or activity of the Ira2 protein can be decreased to achieve an increase in the signaling activity in the RAS/cAMP/PKA pathway in the yeast cell. In an embodiment, the yeast cell expresses a mutation in the Ira2 protein (herein referred to as a mutated Ira2 protein) which decreases its biological activity. For example, the mutated Ira2 protein can be a variant or a fragment of the wild-type Ira2 protein resulting in an increase in the biological activity of the wild-type Ras1 protein and/or the wild-type Ras2 protein. As it is known in the art, the Ira2 protein converts the wild-type Ras1 protein or the wild-type Ras2 protein from their GTP-bound to their GDP-bound inactive form. The biological activity of the Ira2 protein includes binding to the wild-type Ras1 protein and to the wild-type Ras2 protein. As such, in the context of the present disclosure, a mutated Ira2 protein having decreased (biological activity) can exhibit a lower binding affinity for the wild-type Ras1 protein, the wild-type Ras2 protein or both, when compared to the wild-type Ira2. In a specific embodiment, the mutated Ira2 protein can be a truncated Ira2 protein encoded by a nucleic acid molecule or a gene which includes a frame-shift mutation. The mutated Ira2 protein can have the amino acid sequence of SEQ ID NO: 9 or be encoded by a nucleic acid molecule having the sequence of SEQ ID NO: 7.

In an embodiment, the expression and/or activity of the Ira1 protein can be decreased to achieve an increase in the signaling activity in the RAS/cAMP/PKA pathway in the yeast cell or strain. In an embodiment, the yeast cell expresses a mutation in the Ira1 protein (herein referred to as a mutated Ira1 protein) which decreases its biological activity. For example, the mutated Ira1 protein can be a variant or a fragment of the wild-type Ira1 protein resulting in an increase in the biological activity of the wild-type Ras1 protein and/or the wild-type Ras2 protein. The Ira1 protein converts the wild-type Ras1 protein or the wild-type Ras2 protein from their GTP-bound to their GDP-bound inactive form. The biological activity of the Ira1 protein includes binding to the wild-type Ras1 protein and/or to the wild-type Ras2 protein. As such, in the context of the present disclosure, a mutated Ira1 protein having decreased (biological activity) can exhibit a lower binding affinity for the wild-type Ras1 protein, the wild-type Ras2 protein or both. In a specific embodiment, the mutated Ira1 protein can be a truncated Ira1 protein encoded by a nucleic acid molecule or a gene which includes a frame-shift mutation.

In yet another example, the expression and/or activity of one or more protein of the RAS/cAMP/PKA pathway can be increased and the expression and/or activity of one or more protein of the RAS/cAMP/PKA pathway can be decreased (both in comparison with a corresponding control yeast cell or strain) to achieve an increase in the signaling activity RAS/cAMP/PKA pathway.

In order to achieve such increase in RAS/cAMP/PKA signaling, it is also possible to regulate the activity of one or more protein of the RAS/cAMP/PKA signaling pathway at the post-transcriptional level. For example, it is possible to genetically modify the recombinant yeast host cell to allow for the glucose-induced protein turnover of one or more proteins in the RAS/cAMP/PKA signaling pathway (e.g., the Ira1 protein and/or the Ira2 protein for example).

A mutated protein of the RAS/cAMP/PKA pathway (also referred to as a variant) can have at least 70%, 80%, 85%, 90%, 95%, 96%, 97%, 98% or 99% identity to the corresponding wild-type protein, provided that the mutated proteins allows for the increased signaling of the RAS/cAMP/PKA pathway. A variant comprises at least one amino acid difference when compared to the amino acid sequence of the corresponding wild-type protein.

The term "percent identity", as known in the art, is a relationship between two or more polypeptide sequences or two or more polynucleotide sequences, as determined by comparing the sequences. The level of identity can be determined conventionally using known computer programs. Methods for determining percent identity, as discussed in more detail below in relation to polynucleotide identity, are also relevant for evaluating polypeptide sequence identity. "Identity" can be readily calculated by known methods, including but not limited to those described in: Computational Molecular Biology (Lesk, A. M., ed.) Oxford University Press, NY (1988); Biocomputing: Informatics and Genome Projects (Smith, D. W., ed.) Academic Press, NY (1993); Computer Analysis of Sequence Data, Part I (Griffin, A. M., and Griffin, H. G., eds.) Humana Press, NJ (1994); Sequence Analysis in Molecular Biology (von Heinje, G., ed.) Academic Press (1987); and Sequence Analysis Primer (Gribskov, M. and Devereux, J., eds.) Stockton Press, NY (1991). Preferred methods to determine identity are designed to give the best match between the sequences tested. Methods to determine identity and similarity are codified in publicly available computer programs. Sequence alignments and percent identity calculations may be performed using the Megalign program of the LASERGENE bioinformatics computing suite (DNASTAR Inc., Madison, Wis.). Multiple alignments of the sequences disclosed herein were performed using the Clustal method of alignment (Higgins and Sharp (1989) CABIOS. 5:151-153) with the default parameters (GAP PENALTY=10, GAP LENGTH PEN ALT Y=10). Default parameters for pairwise alignments using the Clustal method were KTUPLB 1, GAP PENALTY=3, WINDOW=5 and DIAGONALS SAVED=5.

The variants or mutated proteins described herein may be (i) one in which one or more of the amino acid residues are substituted with a conserved or non-conserved amino acid residue (preferably a conserved amino acid residue) and such substituted amino acid residue may or may not be one encoded by the genetic code, or (ii) one in which one or more of the amino acid residues includes a substituent group, or (iii) one in which the mature polypeptide is fused with another compound, such as a compound to increase the half-life of the polypeptide (for example, polyethylene glycol), or (iv) one in which the additional amino acids are fused to the mature polypeptide for purification of the polypeptide.

The mutated protein of the RAS/cAMP/PKA pathway can also be a fragment of the corresponding wild-type protein. The "fragments" have at least at least 10, 20, 30, 40, 50, 60, 70, 80, 90, 100, 200, 300, 400, or 500 or more consecutive amino acids of the corresponding wild-type protein. A fragment comprises at least one less amino acid residue when compared to the amino acid sequence of the corresponding wild-type protein.

In an embodiment, the yeast cell does not need to be genetically engineered to increase the signaling activity in the RAS/cAMP/PKA pathway. For example, the yeast cell can be selected from a population of yeast cells (which may be naturally-occurring) for its ability to exhibit a high signaling activity in the RAS/cAMP/PKA pathway when compared to other yeast cells in the population. The selection can be made at the nucleic acid level (by determining the nucleic acid sequence of one or more genes coding for one or more proteins in the RAS/cAMP/PKA pathway or the level of expression of one or more genes coding for one or more proteins in the RAS/cAMP/PKA pathway), at the protein level (by determining the amino acid sequence of one or more proteins in the RAS/cAMP/PKA pathway, the level of expression of one or more proteins in the RAS/cAMP/PKA pathway or the activity of one or more proteins in the RAS/cAMP/PKA pathway) or at the intermediates level (by determining the amount of GTP, GDP or cAMP for example). The selection can be done before the propagation step, during the propagation step, before the fermentation step and/or during the fermentation step. In an embodiment, the selection is done prior to the fermentation step. In another embodiment, the selection is done prior to the propagation step.

In another example, in order to achieve the selection of the yeast cells for its ability to exhibit an increased signaling activity in the RAS/cAMP/PKA pathway when compared to other yeast cells in the population, it is possible to exclude yeast cells exhibiting low signaling activity in the RAS/cAMP/PKA pathway. This exclusion can be made at the nucleic acid level (by determining the nucleic acid sequence of one or more genes coding for one or more proteins in the RAS/cAMP/PKA pathway or the level of expression of one or more genes coding for one or more proteins in the RAS/cAMP/PKA pathway), at the protein level (by determining the amino acid sequence of one or more proteins in the RAS/cAMP/PKA pathway, the level of expression of one or more proteins in the RAS/cAMP/PKA pathway or the activity of one or more proteins in the RAS/cAMP/PKA pathway) or at the intermediates level (by determining the amount of GTP, GDP or cAMP for example). The exclusion can be done before the propagation step, during the propagation step, before the fermentation step and/or during the fermentation step. In an embodiment, the exclusion is done prior to the fermentation step. In another embodiment, the exclusion is done prior to the propagation step.

In some embodiments, it is advisable to genetically engineer a recombinant yeast host cell to increase its signaling activity in the RAS/cAMP/PKA pathway (when compared to a corresponding yeast cell which does not include such genetic modifications). The recombinant yeast host cell can include a genetic modification in one or more protein of the RAS/cAMP/PKA pathway. For example, the genetic modification can include the addition of an expression cassette for one or more protein of the RAS/cAMP/PKA pathway (at a neutral integration site for example) or to replace the one or more native protein of the RAS/cAMP/PKA pathway.

The genetic modification can be the introduction of an heterologous nucleic acid molecule coding for an heterologous promoter and/or an heterologous nucleic acid molecule. The term "heterologous" when used in reference to a nucleic acid molecule (such as a promoter or a coding sequence) or a protein (such as a protein in the RAS/cAMP/PKA pathway) refers to a nucleic acid molecule or a protein not natively found in the host organism or cell. "Heterologous" also includes a native coding region, or portion thereof, that is removed from the source organism and subsequently reintroduced into the source organism in a form that is different from the corresponding native gene, e.g., not in its natural location in the organism's genome. The heterologous nucleic acid molecule is purposively introduced into the host cell. A "heterologous" nucleic acid molecule or protein may be derived from any source, e.g., eukaryotes, prokaryotes, viruses, etc. In an embodiment, the heterologous nucleic acid molecule may be derived from an eukaryote (such as, for example, another yeast) or a prokaryote (such as, for example, a bacteria). The term "heterologous" as used herein also refers to an element (nucleic acid or protein) that is derived from a source other than the endogenous source. Thus, for example, a heterologous element could be derived from a different strain of host cell, or from an organism of a different taxonomic group (e.g., different kingdom, phylum, class, order, family genus, or species, or any subgroup within one of these classifications). The term "heterologous" is also used synonymously herein with the term "exogenous".

In an example, the recombinant yeast host cell can include an heterologous nucleic acid molecule comprising a first nucleic acid molecule coding for an heterologous and mutated Ras2 protein as described herein. The mutated Ras2 protein can include an amino acid substitution at one or more location when compared to the wild-type Ras2 protein. In an embodiment, the recombinant yeast host cell can also express a wild-type Ras2 protein (which can be native to the recombinant yeast host cell or genetically engineered). Wild-type Ras2 proteins have been characterized in *Saccharomyces cerevisiae* (GenBank Accession Number CAA95974 or AMQB00000000.1), *Yarrowia lipolytica* (GenBank Accession Number AAK52675) and *Candida orthopsilosis* (GenBank Accession Number CCG25689). In an embodiment, the wild-type Ras2 protein has the amino acid sequence of SEQ ID NO: 1 or is encoded by a nucleic acid molecule having the sequence of SEQ ID NO: 4. In another embodiment, the mutated Ras2 protein has the amino acid sequence of SEQ ID NO: 2 or is encoded by the nucleic acid molecule having the sequence of SEQ ID NO: 3.

In another example, the recombinant yeast host cell can include an heterologous nucleic acid molecule comprising a second nucleic acid molecule (alone or in combination with other heterologous nucleic acid molecules) coding for an heterologous and mutated Ras1 protein as described herein. The mutated Ras1 protein can include an amino acid substitution at one or more location when compared to the wild-type Ras1 protein. In an embodiment, the recombinant yeast host cell can also express a wild-type Ras1 protein (which can be native to the recombinant yeast host cell or genetically engineered).

In yet another example, the recombinant yeast host cell can include an heterologous nucleic acid comprising a third nucleic acid molecule (alone or in combination with other heterologous nucleic acid molecules) coding for an heterologous and mutated Ira2 protein as described herein. The mutated Ira2 protein can be a fragment of the wild-type Ira2 protein. Wild-type Ira2 protein have been characterized in *Saccharomyces cerevisiae* (GenBank Accession Number CAA99093 or AMQB00000000.1), *Kluyveromyces marxianus* (GenBank Accession Number BA041432), *Scheffersomyces stipites* (GenBank Accession Number XP_001386919), *Candida orthopsilosis* (GenBank Accession Number CCG24772) and *Wickerhamomyces ciferrii* (GenBank Accession Number XP_011275426). In an embodiment, the mutated Ira2 protein has the amino acid sequence of SEQ ID NO: 8 or is encoded by a nucleic acid molecule having the sequence of SEQ ID NO: 6.

In still another example, the recombinant yeast host cell can include an heterologous nucleic acid comprising a fourth nucleic acid molecule (alone or in combination with other heterologous nucleic acid molecules) coding for an heterologous and mutated Ira1 protein as described herein. The mutated Ira1 protein can be a fragment of the wild-type Ira1 protein.

When a recombinant yeast host cell is made and used, the heterologous nucleic acid molecule(s) it includes can further comprise a promoter for controlling the expression of the nucleic acid molecule (coding a protein of the RAS/cAMP/PKA signaling pathway). "Promoter" refers to a DNA fragment capable of controlling the expression of a coding sequence or functional RNA (in the present disclosure, the first nucleic acid molecule). The term "expression," as used herein, refers to the transcription and stable accumulation of sense (mRNA) from the heterologous nucleic acid molecule described herein. Expression may also refer to translation of mRNA into a polypeptide. Promoters may be derived in their entirety from a native gene, or be composed of different elements derived from different promoters found in nature, or even comprise synthetic DNA segments. It is further recognized that since in most cases the exact boundaries of regulatory sequences have not been completely defined, DNA fragments of different lengths may have identical promoter activity. A promoter is generally bounded at its 3' terminus by the transcription initiation site and extends upstream (5' direction) to include the minimum number of bases or elements necessary to initiate transcription at levels detectable above background. Within the promoter will be found a transcription initiation site (conveniently defined for example, by mapping with nuclease S1), as well as protein binding domains (consensus sequences) responsible for the binding of the polymerase. In the context of the present disclosure, one or more promoter may be used to express the heterologous nucleic acid molecule.

In the context of the present disclosure, the promoter is intended to allow the expression of the nucleic acid molecule during fermentation (e.g., for example, anaerobic conditions) but not during yeast production/propagation (e.g., for example, glucose-limited and aerobic conditions). As used in the context of the present disclosure, the expression "propagation" refers to an expansion phase of a commercial process in which the yeasts are propagated under aerobic conditions to maximize the conversion of the substrate into biomass. As also used in the context of the present disclosure, the expression "fermentation" refers to the use of the propagated biomass to maximize the production produce one or more desired metabolite from a medium. In some embodiments, the promoter could allow the expression of the heterologous nucleic acid molecule in the stationary phase of the yeast (e.g., after propagation but before fermentation, for example, the promoter of the YGP1 gene). Fermentation-inducible promoters include, but are not limited to the promoter of the PDC1 gene, the promoter of the TDH1 gene, the promoter of the TDH3 gene, the promoter of the ENO2 gene, the promoter of the CDC19 gene, the promoter of the HXT3 gene and/or the promoter of the HOR7 gene. An exemplary fermentation-inducible promoter which is not strictly anaerobic is the promoter of the PDC1 gene. In yet another embodiment, the promoter is not an aerobic promoter (e.g., active in presence of oxygen, like the ICL1 promoter, the promoter of the TDH1 gene, the promoter of the TDH2 gene, the promoter of the TDH3 gene, the promoter of the ENO2 gene, the promoter of the CDC19 gene, the promoter of the HXT3 gene and the promoter of the HOR7 gene), a constitutive promoter (e.g., active in all conditions, like the promoter of the ADH1 gene or the promoter of the TEF2 gene), a stationary phase promoter (e.g., active only after cell growth stops like the promoter of the YGP1 gene) or an osmotic stress inducible promoters (e.g., active in response to an osmotic stress like the promoter of the STL1 gene).

In an embodiment, the promoter allows or favors the expression of the nucleic acid molecule in partial or total anaerobic conditions (e.g., anaerobic-regulated or hypoxia-regulated promoter). Therefore, the promoter used favors the expression of the nucleic acid molecule in an environment in which the oxygen level is reduced (e.g., anaerobic conditions or hypoxia) when compared to the oxygen level in ambient air (e.g., aerobic conditions in which oxygen is usually present at about 21% volume in ambient air). The promoter can allow for the expression of the nucleic acid molecule when the recombinant yeast host cell is placed in aerobic conditions, however, under the control of the promoter, the level of expression of the nucleic acid molecule is lower in recombinant yeast host cells placed in aerobic conditions when compared to the level of expression of the same recombinant yeast host cell placed in (partial or total) anaerobic conditions. As such, the promoter allows for the preferential expression of the nucleic acid molecule when the recombinant yeast host cell is placed in conditions of at least partial anaerobia or hypoxia. As used in the context of the present disclosure, the term "anaerobic conditions" refers to conditions in which the oxygen level in the air (by volume) is lower than 21% (for example lower than or equal to about 20, 19, 18, 17, 16, 15, 14, 13, 12, 11, 10, 9, 8, 7, 6, 5, 4, 3, 2, 1 or 0). Because the yeast cells are generally cultured in a liquid, the expression "anaerobic conditions" or "hypoxia" refer to the conditions of an environment in which the oxygen level is reduced (e.g., anaerobic conditions) when compared to the saturated dissolved oxygen level in media at equilibrium with ambient air (e.g., aerobic conditions, with typical oxygen levels of about 21% volume in ambient air). As such, the term "anaerobic conditions" refers to conditions in which the dissolved oxygen level is lower than 100% saturation (for example lower than or equal to about 90, 80, 70, 60, 50, 40, 30, 20, 10, 5, 4, 3, 2, 1, 0.5, 0.1, 0.05, 0.01 or 0% saturation).

The anaerobic-regulated promoters that can be included in the heterologous nucleic acid molecule of the present disclosure can include, but are not limited to the promoter of the DAN1 gene, the promoter of the PAU5 gene, the promoter of the GPD2 gene, the promoter of the PDC1 gene, the promoter of the TPI1 gene, the promoter of the ANB1 gene, the promoter of the ACS2 gene as well as the anaerobic-regulated promoter of the genes listed in Kwast et al., 2002, ter Lind et al., 1999 and Tai et al., 2002.

In still another embodiment, the promoter allows or favors the expression of the heterologous nucleic acid molecule in the absence of glucose (e.g., glucose-repressible promoter). Therefore, some of the promoter that can be used favor the expression of the heterologous nucleic acid molecule in an environment in which glucose is absent. The promoter can allow for the expression of the nucleic acid molecule when the recombinant yeast host cell is placed in the presence of some glucose, however, under the control of the glucose-repressible promoter, the level of expression of the nucleic acid molecule is lower in recombinant yeast host cells placed in the presence of glucose when compared to the level of expression of the nucleic acid molecule in a corresponding recombinant yeast host cell placed in the absence of glucose. As such, the promoter allows for the preferential expression of the heterologous nucleic acid molecule in the absence of glucose. Exemplary glucose-repressible promoters include, but are not limited to the HXT7 promoter and the HXK1 promoter.

In the heterologous nucleic acid molecule, the promoter (or combination of promoters) and the nucleic acid molecule coding for the heterologous protein are operatively linked to one another. In the context of the present disclosure, the expressions "operatively linked" or "operatively associated" refers to fact that the promoter is physically associated to the nucleotide acid molecule coding for the heterologous protein in a manner that allows, under certain conditions, for expression of the heterologous protein from the nucleic acid molecule. In an embodiment, the promoter can be located upstream (5') of the nucleic acid sequence coding for the heterologous protein. In still another embodiment, the promoter can be located downstream (3') of the nucleic acid sequence coding for the heterologous protein. In the context of the present disclosure, one or more than one promoter can be included in the heterologous nucleic acid molecule. When more than one promoter is operatively connected to the heterologous nucleic acid molecule, each of the promoters is operatively linked to the nucleic acid sequence coding for the heterologous protein. The promoters can be located, in view of the nucleic acid molecule coding for the heterologous protein, upstream, downstream as well as both upstream and downstream.

The promoter can be heterologous to the nucleic acid molecule encoding the protein of the RAS/cAMP/PKA signaling pathway. The promoter can be heterologous or derived from a strain being from the same genus or species as the recombinant yeast host cell. In an embodiment, the promoter is derived from the same genus or species of the yeast host cell and the heterologous protein is derived from different genus that the yeast host cell.

In the context of the present disclosure, the heterologous nucleic acid molecule can be integrated in the genome of the recombinant yeast host cell. The term "integrated" as used herein refers to genetic elements that are placed, through molecular biology techniques, into the genome of a host cell. For example, genetic elements can be placed into the chromosomes of the yeast host cell as opposed to in a vector such as a plasmid carried by the host cell. Methods for integrating genetic elements into the genome of a yeast host cell are well known in the art and include, for example, homologous recombination. The heterologous nucleic acid molecule can be present in one or more copies in the yeast host cell's genome.

Alternatively, the heterologous nucleic acid molecule can be independently replicating from the yeast's genome. In such embodiment, the nucleic acid molecule can be stable and self-replicating.

The heterologous nucleic acid molecule can be introduced in the yeast host cell using a vector. A "vector," e.g., a "plasmid", "cosmid" or "YAC" (yeast artificial chromosome) refers to an extra chromosomal element and is usually in the form of a circular double-stranded DNA molecule. Such vectors may be autonomously replicating sequences, genome integrating sequences, phage or nucleotide sequences, linear, circular, or supercoiled, of a single- or double-stranded DNA or RNA, derived from any source, in which a number of nucleotide sequences have been joined or recombined into a unique construction which is capable of introducing a promoter fragment and DNA sequence for a selected gene product along with appropriate 3' untranslated sequence into a cell.

The yeasts cell and the recombinant yeast host cells of the present disclosure can be selected or designed to be capable of utilizing xylose and/or arabinose. As used in the context of the present the expression "capable of utilizing xylose and/or arabinose" refers to the ability of the yeast cells or the recombinant yeast host cells to metabolize xylose and/or arabinose.

In embodiments in which the cells are capable of utilizing xylose. In such embodiment, the recombinant yeast host cell can be modified to express at least one of (or a combination of) a xylose reductase, a xylitol dehydrogenase, a xylose isomerase, xylulokinase, xylose reductase, xylose dehydrogenase, xylonate dehydratase, xylose transketolase and/or a xylose transaldolase protein. Exemplary xylose isomerases include, but are not limited to, those derived from *Parabacteroides distasonis*, *Cyllamyces aberensis*, *Abiotrophia defectiva*, *Chitinophaga pinensis*, *Prevotella ruminicola*, *Piromyces equi*, *Lachnoclostridium phytofermentans*, *Clostridium phytofermentans*, *Catonella morbi* and/or *Bacteroides thetaiotaomicron* as well as those described in WO/2016/024215 as well as in U.S. Pat. No. 8,986,948. In some embodiments, the heterologous xylulokinase (Xks1) can be encoded by the XKS1 gene In yet another embodiment, the cells have "xylanolytic activity", e.g., having the ability of the yeast cells and the recombinant yeast host cells to hydrolyze glycosidic linkages in oligopentoses and polypentoses. The term "xylanase" is the name given to a class of enzymes which degrade the linear polysaccharide beta-1,4-xylan into xylose, thus breaking down hemicellulose, one of the major components of plant cell walls. Xylanases include those enzymes that correspond to Enzyme Commission Number 3.2.1.8. In an embodiment, the recombinant yeast host cell can include one or more genetic modifications (encoding one or more heterologous proteins) to provide xylanolytic activity.

Exemplary recombinant yeast host cells genetically engineered to ferment xylose were disclosed in WO/2016/024215 and U.S. patent application Ser. No. 14/821,955 and can be further modified as described herein to increase their RAS/cAMP/PKA signaling pathway.

In embodiments in which the cells are capable of utilizing arabinose, the disclosure provides a yeast host cell expressing or a recombinant yeast host cell comprising a nucleic acid molecule encoding an arabinose isomerase (AI, such as, for example, the AraA protein from *Bacteroides thetaiotaomicron*), a heterologous polynucleotide encoding a ribulokinase (RK, such as, for example, the AraB protein from *Bacteroides thetaiotaomicron*), a heterologous polynucleotide encoding a ribulose 5-phosphate epimerase (RSPE, such as, for example, the AraD protein from *Bacteroides thetaiotaomicron*) and/or an arabinose transporter (AraT). Embodiments of recombinant yeast host cells capable of utilizing arabinose have been described in WO 2013/071112. The heterologous arabinose isomerase (AraA) can be, for example, derived from *Escherichia coli* (AraA), *Lactobacillus plantarum* (AraA), *Arthrobacter aurescens* (AraA), *Clavibacter michiganensis* (AraA), *Gramella forsetii* (AraA), *Bacillus licheniformis*, *Clostridium acetobutylicum*, *Bacillus subtilis* or *Mycobacterium smegmatis* or described in U.S. Pat. Nos. 9,206,444; 9,303,253; 8,993,301; US Patent Application 2010/0304454 or EP Patent 1 499 708. The heterologous ribulokinase (AraB) can be, for example, derived from *Bacteroides thetaiotamicron* (AraB), *Escherichia coli* (AraB), *Lactobacillus plantarum* (AraB), *Arthrobacter aurescens* (AraB), *Clavibacter michiganensis* (AraB) or *Gramella forsetii* (AraB) or described in U.S. Pat. Nos. 9,206,444; 9,303,253; US Patent Application 2010/0304454 or EP Patent 1 499 708. The heterologous ribulose-epimerase (AraD) can be derived from *Bacteroides thetaiotamicron* (AraD), *Escherichia coli* (AraD), *Lactobacillus plantarum* (AraD), *Arthrobacter aurescens* (AraD), *Clavibacter michiganensis* (AraD) or *Gramella forsetii* (Ara) Dor described in U.S. Pat. No. 9,206,444; 9,303,253; US Patent Application 2010/0304454 or EP Patent 1 499 708. The heterologous arabinose transporter can be derived from *Kluveromyces lactis*, *Kluveromyces thermotolerans*, *Zygosaccharomyces rouxii*, *Vanderwaltozyma polyspora*, *Debaryomyces hansei*, *Aspergillus niger*, *Penicillium chrysogenum*, *Pichia guilermondii*, *Aspergillus flavus*, *Candida lusitaniae*, *Candida albicans*, *Kluveromyces marxianus*, *Pichia stipites* or *Candida arabinofermentans*. To facilitate the transport of arabinose, the recombinant yeast host cell can express the GAL2 gene and/or GAL2 gene). Exemplary recombinant yeast host cells capable of transporting arabinose have been described in WO 2013/071112.

In some embodiments, the recombinant yeast host cells can also express one or more genes from the pentose phosphate pathway (e.g., TAL1 transaldolase, TKL1 Transketolase, RPE1 D-ribulose-5-phosphate 3-epimerase and/or RKI1 Ribose-5-phosphate ketol-isomerase) and/or iron sulfur cluster gene mutants (such as, for example, YFH1T$^{163P}$, ISU1$^{D71N}$, ISU1$^{D71G}$, ISU1$^{S98F}$, NFS1$^{L115W}$, NFS1$^{E458D}$, all described in WO 2016/024215). In some embodiments, the expression of the aldose reductase gene (such as, for example, the ypr1 gene encoding the YPR1 protein and/or the gre3 gene encoding the GRE3 protein) of the recombinant yeast host cells can be down-regulated or deleted.

In some embodiments, the heterologous nucleic acid molecules are codon-optimized with respect to the intended recipient yeast host cell. As used herein the term "codon-optimized coding region" means a nucleic acid coding region that has been adapted for expression in the cells of a given organism by replacing at least one, or more than one, codons with one or more codons that are more frequently used in the genes of that organism. In general, highly expressed genes in an organism are biased towards codons that are recognized by the most abundant tRNA species in that organism. One measure of this bias is the "codon adaptation index" or "CAI," which measures the extent to which the codons used to encode each amino acid in a particular gene are those which occur most frequently in a reference set of highly expressed genes from an organism. The CAI of codon optimized sequences described herein corresponds to between about 0.8 and 1.0, between about 0.8 and 0.9, or about 1.0.

A codon optimized sequence may be further modified for expression in a particular organism, depending on that recipient's biological constraints. For example, large runs of "As" or "Ts" (e.g., runs greater than 4, 5, 6, 7, 8, 9, or 10 consecutive bases) can be removed from the sequences if these are known to effect transcription negatively. Furthermore, specific restriction enzyme sites may be removed for molecular cloning purposes. Additionally, the nucleic acid molecules can be checked for direct repeats, inverted repeats and mirror repeats with lengths of ten bases or longer, which can be modified manually by replacing codons with "second best" codons, i.e., codons that occur at the second highest frequency within the particular organism for which the sequence is being optimized.

In the context of the present disclosure, the yeast cell or recombinant yeast host cell can be from the genus *Saccharomyces, Kluyveromyces, Arxula, Debaryomyces, Candida, Pichia, Phaffia, Schizosaccharomyces, Hansenula, Kloeckera, Schwanniomyces* or *Yarrowia*.

Suitable yeast species can include, for example, *S. cerevisiae, S. bulderi, S. barnetti, S. exiguus, S. uvarum, S. diastaticus, K. lactis, K. marxianus* or *K. fragilis*. In some embodiments, the yeast is selected from the group consisting of *Saccharomyces cerevisiae, Schizzosaccharomyces pombe, Candida albicans, Pichia pastoris, Pichia stipitis, Yarrowia lipolytica, Hansenula polymorpha, Phaffia rhodozyma, Candida utilis, Arxula adeninivorans, Debaryomyces hansenii, Debaryomyces polymorphus, Schizosaccharomyces pombe* and *Schwanniomyces occidentalis*. In one particular embodiment, the yeast is *Saccharomyces cerevisiae*. In some embodiment, the yeast cell can be an oleaginous yeast cell. For example, the oleaginous yeast host cell can be from the genera *Blakeslea, Candida, Cryptococcus, Cunninghamella, Lipomyces, Mortierella, Mucor, Phycomyces, Pythium, Rhodosporidum, Rhodotorula, Trichosporon* or *Yarrowia*. In some alternative embodiment, the host cell can be an oleaginous microalgae host cell (e.g., for example, from the genera *Thraustochytrium* or *Schizochytrium*).

As described herein, the recombinant yeast host cells are genetically engineered (transduced or transformed or transfected) with the heterologous nucleic acid molecule encoding the heterologous protein. The nucleic acid molecule can be introduced in the host cell on a vector, which may be, for example, a cloning vector or an expression vector comprising a sequence encoding a heterologous protein. The host cells can comprise one or more heterologous nucleic acid molecule(s) each being either present as integrated copies or independently-replicating copies.

The recombinant host cells or cell cultures, as described above, can be further analyzed for hydrolysis of cellulose, or starch, or pentose sugar utilization (e.g., by a sugar detection assay), for a particular type of saccharolytic enzyme activity (e.g., by measuring the individual endoglucanase, glucosidase, cellobiohydrolase, xylanase, glucanase, xylosidase, xylan esterase, arabinofuranosidase, galactosidase, cellobiose phosphorylase, cellodextrin phosphorylase, mannanase, mannosidase, xyloglucanase, endoxylanase, glucuronidase, acetylxylanesterase, arabinofuranohydrolase, swollenin, glucuronyl esterase, expansin, pectinase, feruoyl esterase, alpha-amylase, beta-amylase, glucoamylase, pullulanase, isopullulanase, alpha-glucosidase, beta-glucosidase, galactosidase, arabinase, arabinoxylanase, arabinosidase, arabinofuranosidase, arabinoxylanase, arabinosidase, and arabinofuranosidase, arabinose isomerase, ribulose-5-phosphate 4-epimerase, xylose isomerase, xylulokinase, xylose reductase, xylose dehydrogenase, xylitol dehydrogenase, xylonate dehydratase, xylose transketolase, and/or xylose transaldolase) or for total cellulase activity. Endoglucanase activity can be determined, for example, by measuring an increase of reducing ends in an endoglucanase specific CMC or hydroxyethylcellulose (HEC) substrate.

Cellobiohydrolase activity can be measured, for example, by using insoluble cellulosic substrates such as the amorphous substrate phosphoric acid swollen cellulose (PASO) or microcrystalline cellulose (Avicel™) and determining the extent of the substrate's hydrolysis. β-glucosidase activity can be measured by a variety of assays, e.g., using cellobiose. Assays for activity of other saccharolytic enzyme types are known in the art and are exemplified below.

A total saccharolytic enzyme activity, which can include the activity of endoglucanase, glucosidase, cellobiohydrolase, xylanase, glucanase, xylosidase, xylan esterase, arabinofuranosidase, galactosidase, cellobiose phosphorylase, cellodextrin phosphorylase, mannanase, mannosidase, xyloglucanase, endoxylanase, glucuronidase, acetylxylanesterase, arabinofuranohydrolase, swollenin, glucuronyl esterase, expansin, pectinase, feruoyl esterase protein, alpha-amylase, beta-amylase, glucoamylase, alpha-glucosidase, beta-glucosidase, galactosidase, arabinase, arabinoxylanase, arabinosidase, arabinofuranosidase, arabinoxylanase, arabinosidase, pullulanase, isopullulanase, arabinose isomerase, ribulose-5-phosphate 4-epimerase, xylose isomerase, xylulokinase, xylose reductase, xylose dehydrogenase, xylitol dehydrogenase, xylonate dehydratase, xylose transketolase, and xylose transaldolase can hydrolyze biomass feedstocks synergistically. For example, total cellulase activity can thus be measured using insoluble substrates including pure cellulosic substrates such as Whatman No. 1 filter paper, cotton linter, microcrystalline cellulose, bacterial cellulose, algal cellulose, and cellulose-containing substrates such as dyed cellulose, alpha-cellulose or pretreated lignocellulose. Specific activity of cellulases can also be detected by methods known to one of ordinary skill in the art, such as by the Avicel assay (described supra) that would be normalized by protein (cellulase) concentration measured for the sample. Total saccharolytic activity could be also measured using complex substrate containing starch, cellulose and hemicellulose such as corn mash by measuring released monomeric sugars.

In additional embodiments, the yeast host cells and the recombinant host cells or cell cultures can be assayed for their ability to produce ethanol. Ethanol production can be measured by techniques known to one or ordinary skill in the art, e.g., by a standard HPLC refractive index method.

Propagation of Yeast Cells

In another aspect, the present disclosure provides recombinant yeast host cells capable of being propagated prior to fermentation at levels similar to a non-genetically modified corresponding yeast host cells. In an embodiment, the present disclosure provides a method of propagating recombinant yeast host cells in a propagation medium prior to fermentation. The method is preferably conducted in glucose-limited and aerobic conditions. The propagation medium, which is usually in a liquid form, comprises nutrients allowing propagation. In some embodiments, the propagation medium is selected to achieve rapid growth. For example, the culture medium can comprise a carbon source (such as, for example, molasses, sucrose, glucose, dextrose syrup, ethanol and/or corn steep liquor), a nitrogen source (such as, for example, ammonia) and a phosphorous source (such as, for example, phosphoric acid).

The method can further include processing the propagated recombinant yeast host cells after propagation for storage. For example, the method can further including preparing a high cell-density preparation of the propagated recombinant yeast host cells. This can be achieved by concentrating the propagated recombinant yeast host cells (by centrifugation or filtration for example) in a liquid medium. The concentrated propagated recombinant yeast host cells can also be admixed in a storage medium (which can contain glycerol). The high cell-density preparation can also include lyophilizing the propagated recombinant yeast host cells. The lyophilized propagated recombinant yeast host cells can also be admixed in a storage medium (preferably a dry storage medium).

Methods of Fermenting Using the Yeast Cells

The present disclosure provides a method of fermenting a fermentation medium which comprises contacting the yeast cells or the recombinant yeast host cells described herein with the fermentation medium. In an embodiment, the fermentation medium comprises glucose and at least one additional fermentable carbon source (such as C5 carbon source, a monosaccharide (xylose or arabinose for example) or a disaccharide (maltose or cellobiose for example)). In still another embodiment, the fermentation medium comprises a lignocellulosic material, such as, for example, sugarcane bagasse, wood or corn fiber. In still another embodiment, the fermentation is conducted in conditions of low ethanol stress (e.g. the resulting fermentation does not exceed a concentration of ethanol higher than 130 g/L, 120 g/L, 110 g/L or 100 g/L).

The yeast cell of the present disclosure (which, in an embodiment, is not genetically modified) can be advantageously used for food production, for example bread making. In such embodiment, the yeast host cell is placed in a medium comprising glucose and maltose. In such embodiment, the fermentation medium can comprise wheat.

The recombinant yeast host cell of the present disclosure can be used to ferment numerous biomass feedstocks. In some embodiments, substrates (or fermentation medium) for can be divided into two categories, soluble and insoluble, based on their solubility in water. Soluble substrates include alpha-dextrins, cellodextrins or derivatives, carboxymethyl cellulose (CMC), or hydroxyethyl cellulose (HEC). Insoluble substrates include insoluble starch (raw or gelatinized), crystalline cellulose, microcrystalline cellulose (Avicel™), amorphous cellulose, such as phosphoric acid swollen cellulose (PASO), dyed or fluorescent cellulose and lignocellulosic biomass. These substrates are generally highly ordered cellulosic material and thus only sparingly soluble. It will be appreciated that suitable lignocellulosic material may be any feedstock that contains soluble and/or insoluble cellulose and hemicellulose, where the insoluble cellulose and hemicellulose may be in a crystalline or non-crystalline form. In various embodiments, the lignocellulosic biomass comprises, for example, wood, corn, corn stover, sawdust, bark, leaves, agricultural and forestry residues, grasses such as switchgrass, ruminant digestion products, municipal wastes, paper mill effluent, recycled paper-based products (such as, for example, newspaper, cardboard) or combinations thereof. Such method can allow for the generation of one or more fermentation products such as, for example, ethanol, butanol, acetate, amino acids and vitamins In some embodiments, the methods described herein can be used to produce ethanol at a particular rate. For example, in some embodiments, ethanol is produced at a rate of at least about 0.1 mg per hour per liter, at least about 0.25 mg per hour per liter, at least about 0.5 mg per hour per liter, at least about 0.75 mg per hour per liter, at least about 1.0 mg per hour per liter, at least about 2.0 mg per hour per liter, at least about 5.0 mg per hour per liter, at least about 10 mg per hour per liter, at least about 15 mg per hour per liter, at least about 20.0 mg per hour per liter, at least about 25 mg per hour per liter, at least about 30 mg per hour per liter, at least about 50 mg per hour per liter, at least about 100 mg per hour per liter, at least about 200 mg per hour per liter, or at least about 500 mg per hour per liter.

Ethanol production can be measured using any method known in the art. For example, the quantity of ethanol in fermentation samples can be assessed using HPLC analysis. Many ethanol assay kits are commercially available that use, for example, alcohol oxidase enzyme based assays.

The present invention will be more readily understood by referring to the following examples which are given to illustrate the invention rather than to limit its scope.

EXAMPLE I—CHARACTERIZATION OF RAS2 MUTATIONS

A description of the *Saccharomyces cerevisiae* strains used in this Example is provided in Table 1.

TABLE 1

Description of the strains characterized in Example I

| Designation | Genotype |
| --- | --- |
| M2581 | *S. cerevisiae* strain (not genetically modified) expressing a wild-type native Ras2 protein |
| M2582 | Genetically-modified *S. cerevisiae* strain expressing a mutant Ras2 protein (A66T) |
| M7750 | Genetically-modified *S. cerevisiae* strain expressing a wild-type native Ras2 protein<br>Inactivated genes: Δgpd2, Δfdh1, Δfdh2, Δfcy1<br>Overexpressed genes: *Saccharomycopsis fibuligera* glu0111 (GeneBank Accession CAC83969.1), gene encoding the Pfla polypeptide, gene encoding the Pflb polypeptide, gene encoding the Adhe polypeptide |
| M7752 | Genetically-modified *S. cerevisiae* strain expressing a mutant Ras2 protein (A66T)<br>Inactivated genes: Δgpd2, Δfdh1, Δfdh2, Δfcy1<br>Overexpressed genes: *Saccharomycopsis fibuligera* glu0111 (GeneBank Accession CAC83969.1), gene encoding the Pfla polypeptide, gene encoding the Pflb polypeptide, gene encoding the Adhe polypeptide |

Fermentations were conducted at high cell density, under conditions designed to mimic bread making conditions. Specifically, fermentations were conducted with a 2% dry yeast dose equivalent in media containing 10% maltose, 2% glucose, 4% sodium chloride, 0.1% sodium citrate, 0.1% yeast extract, pH 5.5. Glucose, maltose, ethanol and glycerol concentrations were measured using HPLC. The levels of cAMP were measured with an ELISA assay.

Figure 2:
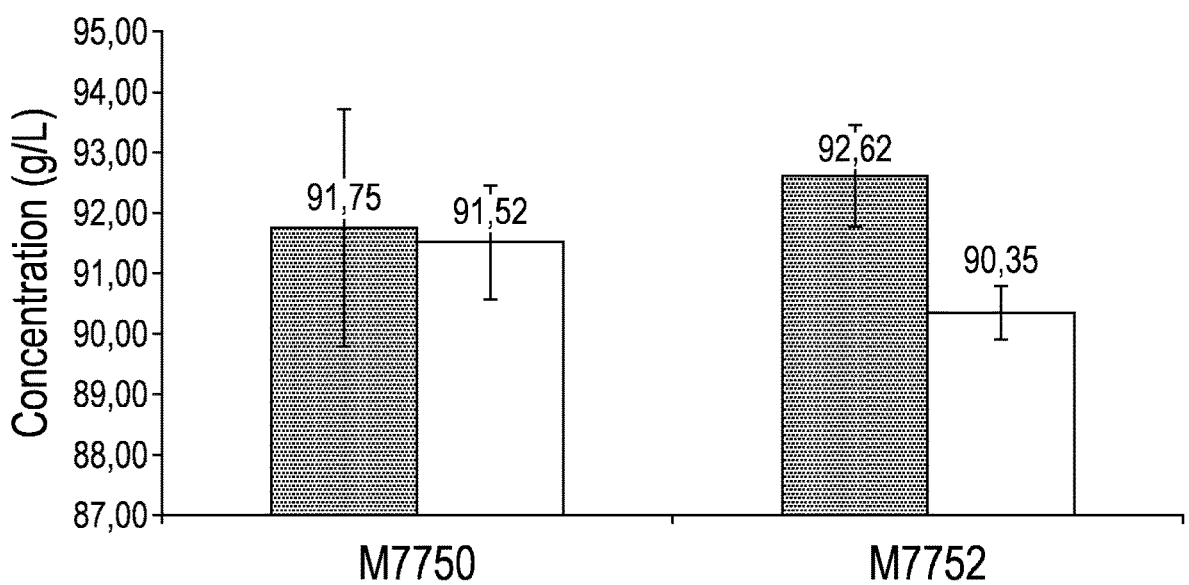
FIG. 2 illustrates maltose consumption during fermentation of a glucose/maltose medium in function of yeast strain used. Results are shown as the concentration of residual maltose (in g/L) in media fermented for 1.5 hours (grey bars) or 4 hours (white bars) for the various *Saccharomyces cerevisiae* strains used (M7750 or M7752).
Figure 3:
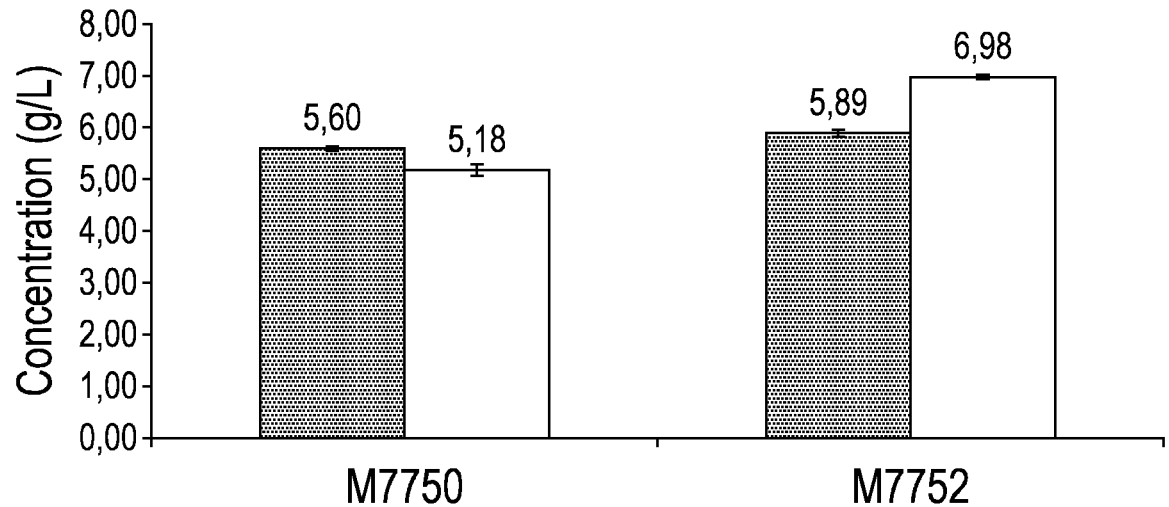
FIG. 3 illustrates ethanol production during fermentation of a glucose/maltose medium in function of yeast strain used. Results are shown as the concentration of ethanol produced (in g/L) in media fermented for 1.5 hours (gray bars) or 4 hours (white bars) for the various *Saccharomyces cerevisiae* strains used (M7750 or M7752).
Figure 4:
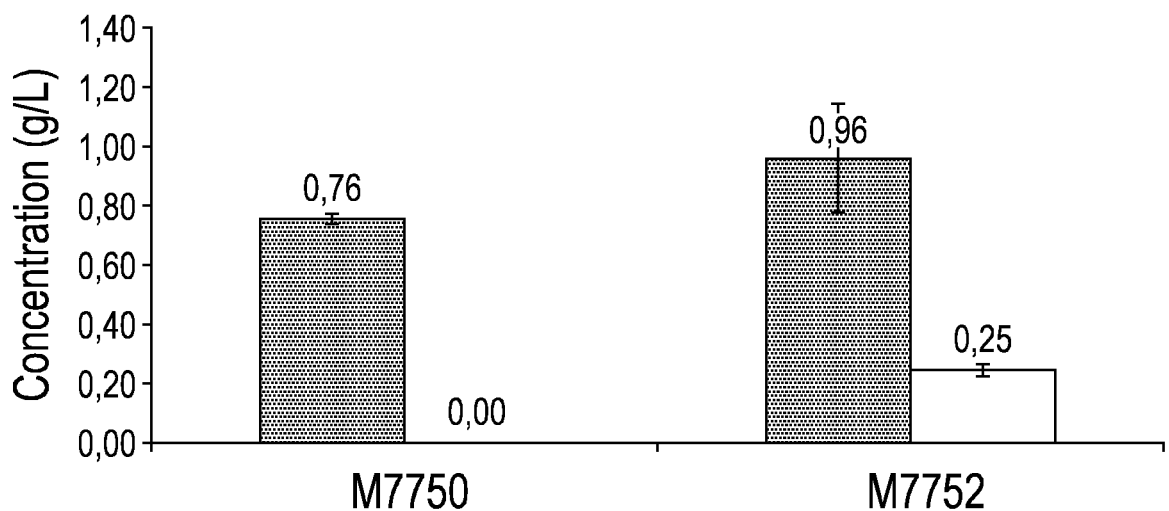
FIG. 4 illustrates glycerol production during fermentation of a glucose/maltose medium in function of yeast strain used. Results are shown as the concentration of glycerol produced (in g/L) in media fermented for 1.5 hours (gray bars) or 4 hours (white bars) for the various *Saccharomyces cerevisiae* strains used (M7750 or M7752).

It was found that, in liquid media containing a mix of glucose and maltose at similar concentrations as in "lean" (no added sugar) dough, strains bearing the $Ras2^{A66T}$ mutation consumed glucose and maltose more quickly (FIGS. 1 and 2) and produced more ethanol (and therefore carbon dioxide), indicating higher fermentative capacity compared to their wild type counterparts (FIG. 3). In addition, the strains bearing the $Ras2^{A66T}$ mutation have improved glycerol production, an important feature of dough fermentation (FIG. 4).

Figure 5:
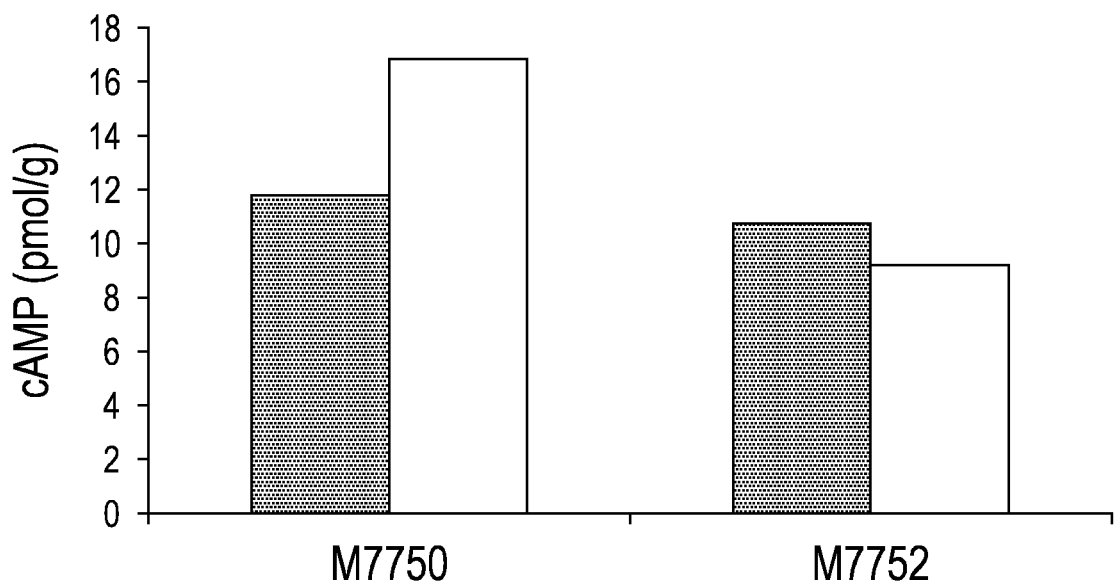
FIG. 5 illustrates the cAMP levels during culture in glucose-only medium in function of the yeast strain used. Results are shown as cAMP levels (pM/g) after 8 hours of fermentation in yeast extract peptone media containing glucose as a carbon source, with (white bars) or without (gray bars) a 100 mM glucose spike prior to cell collection for the various *Saccharomyces cerevisiae* strains used (M7750 or M7752).
Figure 6:
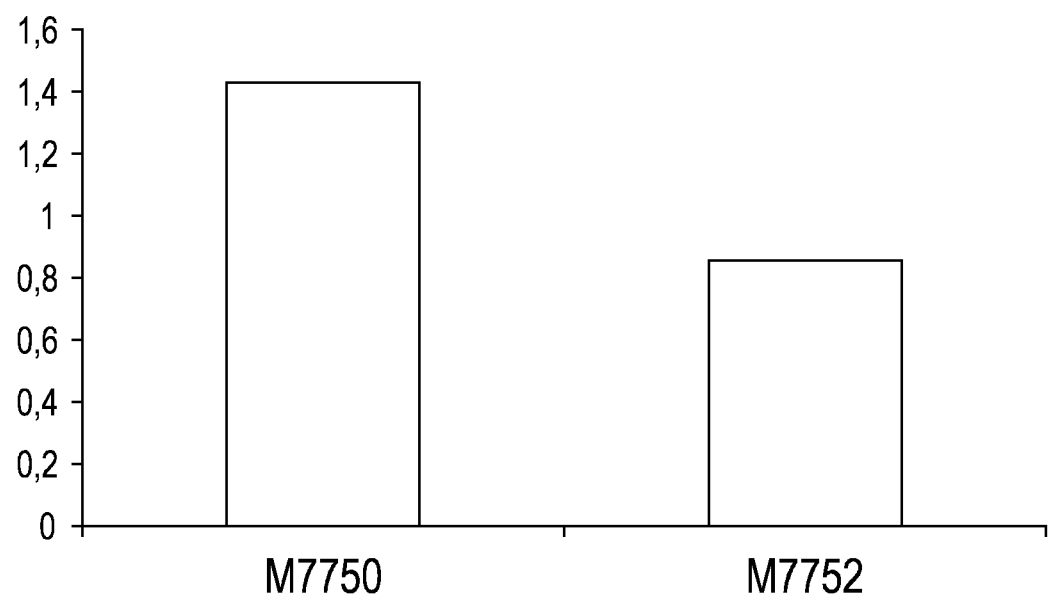
FIG. 6 illustrates the ratios of the glucose spike-to-basal cAMP levels presented in FIG. 5 for the various *Saccharomyces cerevisiae* strains used (M7750 or M7752).

It was also found that strains bearing the $Ras2^{A66T}$ mutation had abnormal cAMP responses to a glucose spike, showing that cAMP signaling is dysregulated. These effects are similar to the known response of a $Ras2^{val19}$ hyperactive mutant to a glucose spike (Mbonyi et al., 1988) (FIGS. 5 and 6).

EXAMPLE II—CHARACTERIZATION OF RAS2 MUTATIONS On XYLOSE FERMENTATION

Multiple *S. cerevisiae* strains were genetically engineered allow xylose fermentation by expressing a heterologous xylose isomerase, upregulation of the pentose phosphate pathway (RKI1, RPE1, TKL1, TKI1) and XKS1, and deleting aldose reductase activity (e.g. GRE3). The effects of introducing an heterologous mutated Ras2 protein (bearing the A66T mutation) in such strains were characterized.

TABLE 2

Description of the S. cerevisiae strains of Example II

| Designation | Genotype |
|---|---|
| M11321 | The GRE3 locus of strain M2390 was replaced with expression cassettes for the pentose phosphate pathway genes RPE1, RKI1, TKL1, and TAL1 as well as the native S. cerevisiae xyulokinase XKS1. A heterologous xylose isomerase gene from C. morbi (WP_023355929) was introduced at multiple neutral integrations sites. In addition the YPR1 locus was deleted and the YFH1 ORF was engineered to contain a T163P point mutation. The resulting strain was adapted on C5 washate to create M11321. |
| M12557 | The GRE3 locus of strain M2390 was replaced with expression cassettes for the pentose phosphate pathway genes RPE1, RKI1, TKL1, and TAL1 as well as the native S. cerevisiae xyulokinase XKS1. A heterologous xylose isomerase gene from C. morbi (WP_023355929) was introduced at multiple neutral integrations sites. In addition the YPR1 locus was deleted and the YFH1 ORF was engineered to contain a T163P point mutation. |
| M2390 | Not genetically modified, wild type S. cerevisiae This strain cannot ferment xylose |
| M8349 | The GRE3 locus of strain M2390 was replaced with expression cassettes for the pentose phosphate pathway genes RPE1, RKI1, TKL1, and TAL1 as well as the native S. cerevisiae xyulokinase XKS1. A heterologous xylose isomerase gene from B. thetaiotaomicron (WP_011107447) was introduced at a neutral integration site. |
| M12076 | Same modifications as M8349 ΔRAS2::RAS2$^{A66T}$ |
| M12196 | The GRE3 locus was replaced with expression cassettes for the pentose phosphate pathway genes RPE1, RKI1, TKL1, and TAL1, as well as the native S. cerevisiae xyulokinase XKS1 and the heterologous xylose isomerase gene from C. morbi (WP_023355929). In addition the YPR1 locus was deleted and replaced with additional C. morbi xylose isomerase (WP_023355929). |
| M12543 | Same modifications as M12196 An heterologous Ras2 protein bearing the A66T mutation and under the control of a Ras2 promoter was introduced at a neutral integration site. |
| M12621 | Same modifications as M12557 An heterologous Ras2 protein bearing the A66T mutation and under the control of a RAS2 promoter (Ras2p) was introduced at a neutral integration site. |
| M12624 | Same modifications as M12557 An heterologous Ras2 protein bearing the A66T mutation and under the control of a DAN1 promoter (Dan1p) was introduced at a neutral integration site. |
| M12625 | Same modifications as M12557 An heterologous Ras2 protein bearing the A66T mutation and under the control of a ANB1 promoter (Anb1p) was introduced at a neutral integration site. |
| M12627 | Same modifications as M12557 An heterologous Ras2 protein bearing the A66T mutation and under the control of a HXK1 promoter (Hxk1p) was introduced at a neutral integration site. |

M8349 and M12076 strains were propagated overnight at 35° C. in YPD$_{40}$ (containing 40 g/L dextrose). Serum bottles containing 30 mL of YPD$_{10}$X$_{70}$ media (containing 10 g/L dextrose and 70 g/L xylose) were inoculated with 30 μL of the overnight cultures, sealed and grown at 32° C. with shaking at 150 rpm. The flow rate of CO$_2$ off gas was monitored as proxy for ethanol production and a final time point HPLC sample (for glucose, glycerol and ethanol determination) was taken following 90 hours of growth. A second set of serum bottles containing 50 mL of YP medium containing 300 g/L of maltodextrin were inoculated with 50 μL of overnight YPD$_{40}$ culture and dosed with 0.48 AGU/g of Spirizyme® Excel (Novozymes). The cultures were grown at 32° C. for 24 hours before dropping the temperature to 30° C. for the remainder of the fermentation. An endpoint HPLC sample (for glucose, glycerol and ethanol determination) was collected at 66 hours for H-column analysis.

Figure 7:
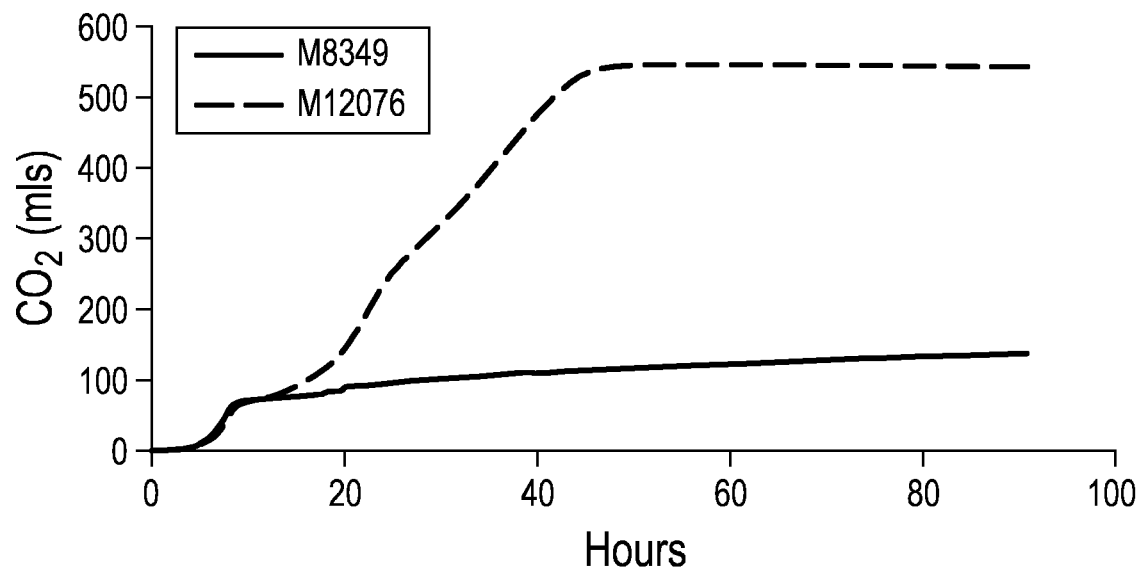
FIG. 7 compares $CO_2$ production (measured as mls) in function of the number of hours in fermentation for *S. cerevisiae* strain M8349 (regular line) or M12076 (dashed line) grown anaerobically.
Figure 8:
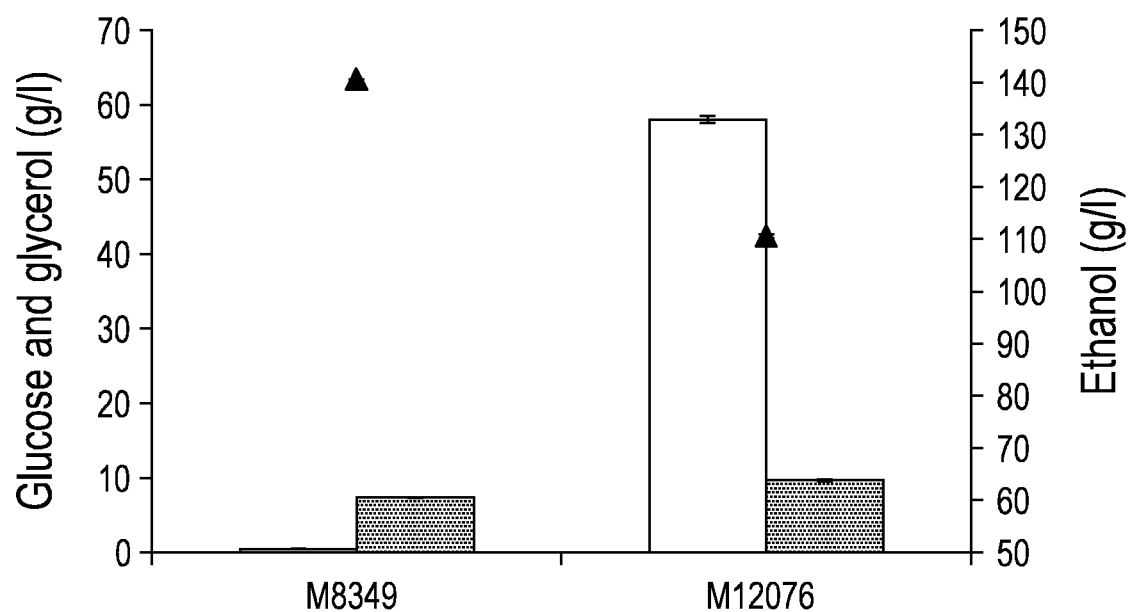
FIG. 8 compares residual glucose (in g/L, white bars), glycerol production (in g/L, grey bars) and ethanol production (in g/L, ▲) in media in function of *S. cerevisiae* strain used (M8349 or M12076) grown anaerobically.

The anaerobic growth of M8349 and M12076 strains in YPD$_{10}$X$_{70}$ medium was compared. As shown on FIGS. 7 and 8, the expression of the mutated Ras2 protein (A66T) in the M12076 strain, when compared to the parental strain M8349 lacking such mutated Ras2 protein, increased CO$_2$ production, sugar consumption, glycerol production and ethanol production.

Figure 9A:
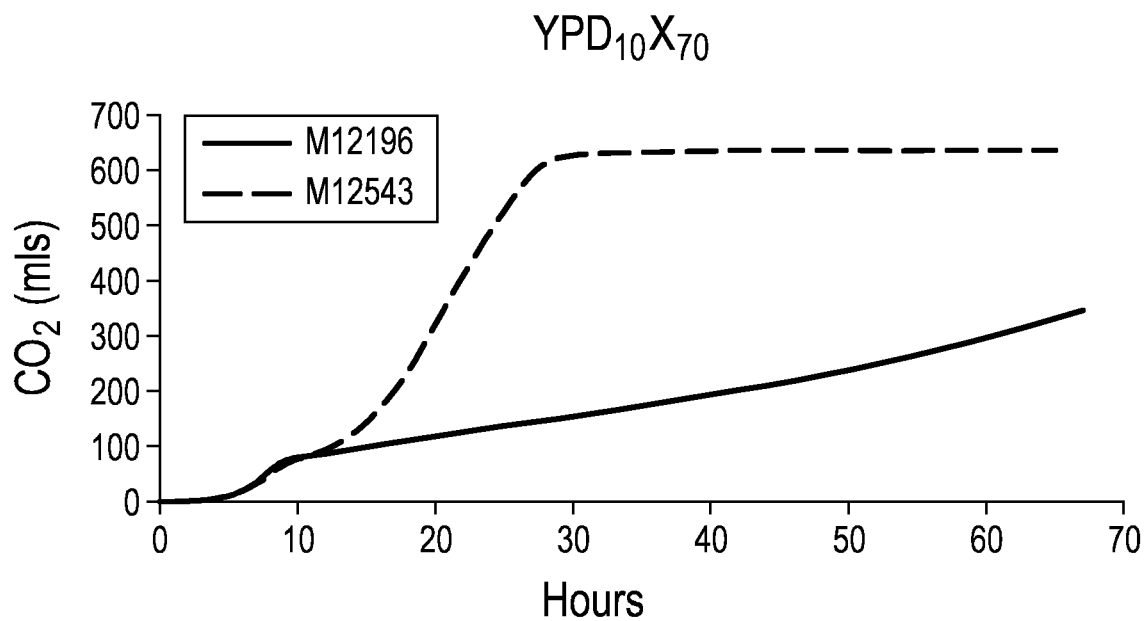
FIGS. 9A and B compare $CO_2$ production (in mls) in function of the number of hours of fermentation in *S. cerevisiae* strains M12196 (regular line) and M12543 (dashed line). Fermentation was conducted in a $YPD_{10}X_{70}$ medium (A) or a SP3 media (B).
Figure 9B:
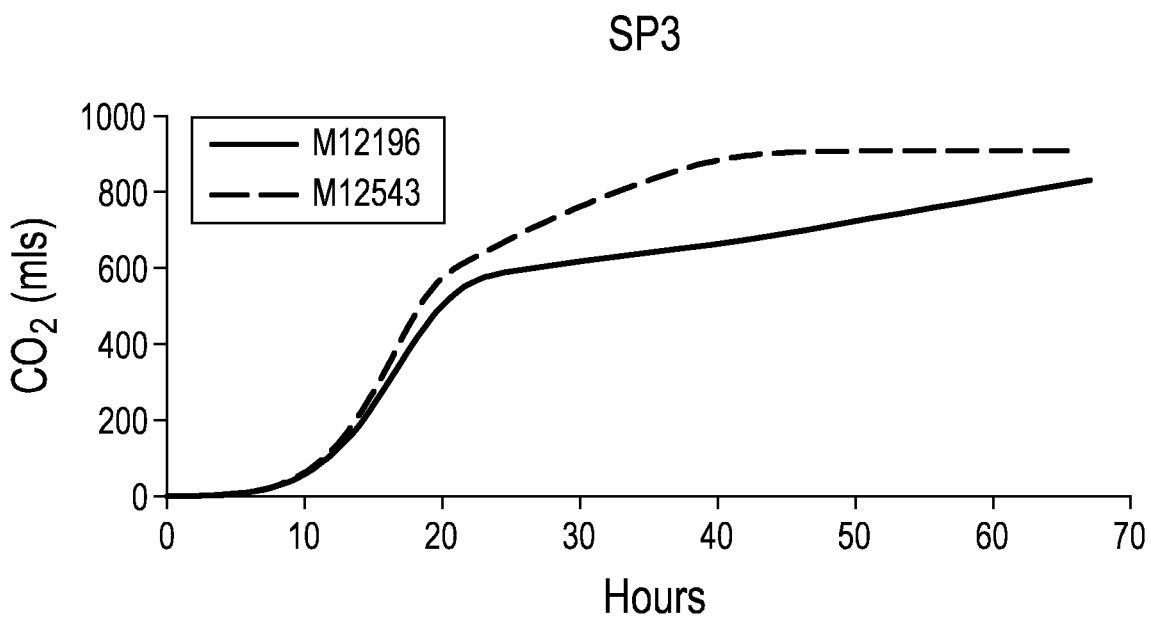

Overnight cultures of M12196 and M12543 were propagated in YPD$_{40}$ media at 35° C. Aliquots of 30 μL of each culture were used as inoculum into 30 mL of both YPD$_{10}$X$_{70}$ media as well as a YNB-based synthetic media "SP3" (6.700 g/L of YNB with amino acids, 5.000 g/L of tri-sodium citrate, 60.000 g/L of glucose, 45.000 g/L of xylose, 5.000 g/L of galactose, 110.000 g/L of fermentable sugars, 49.5 g/L of theoretical ethanol (0.45 g/g), 0.006 g/L of FeSO$_4$, 8.000 g/L of potassium acetate, 1.000 g/L of lactic acid, 0.500 g/L of HMF, 0.500 g/L of furfural alcohol, 0.200 g/L of sorbic acid, pH 5.5). The serum bottles were sealed and incubated at 32° C. with shaking at 150 rpm. The CO$_2$ off gas was monitored as a proxy for ethanol formation. As shown on FIGS. 9A and 9B, the expression of the mutated Ras2 protein (A66T) in M12543, when compared to the corresponding parental strain M12196 lacking such mutated Ras2 protein, increased CO$_2$ production in both YPD$_{10}$X$_{70}$ and SP3 media.

M11321, M12557, M12621, M12624, M12625 and M12627 were propagated overnight in YPD$_{40}$ media at 35° C. Serum bottles with 30 mL of SP3 media were inoculated with 60 μl of each overnight culture, sealed and incubated at 32° C. with shaking at 150 rpm. M12557, M12621, and M12624 were also used as inoculum in "SP4" medium (6.700 g/L of YNB with amino acids, 5.000 g/L of tri-sodium citrate dehydrate, 30.000 g/L of glucose, 75.000 g/L of xylose, 5.000 g/L of galactose, 110.000 g/L of fermentable sugars, 49.5 g/L of theoretical ethanol (0.45 g/g), 0.006 g/L of FeSO$_4$.7H$_2$O, 9.000 g/L of potassium acetate, 1.000 g/L of lactic acid, 0.500 g/L of vanillin, 0.500 g/L of furfuraldehyde, 0.200 g/L of sorbic acid, pH 5.5). SP4 samples were incubated at 33° C. with shaking at 150 rpm. CO$_2$ off gas was measured for SP3 bottles as a proxy for ethanol production and an endpoint HPLC (for glucose, glycerol and ethanol determination) was taken for both SP3 and SP4 bottles. In addition, in order to assess the feasibility of production, M12557, M12621, M12624, M12625, and M12627 were tested for their growth on molasses. Two independent molasses conditions were used: 80% molasses with either 6 g/L CSL and 4 g/L DAP or 10 g/L urea and 2 g/L MgSO$_4$. An aliquot of 50 mL of molasses was inoculated to a starting OD$_{600}$ of 0.05 from YPD$_{40}$ overnight cultures of each strain and incubated in an aerobic shake flask at 30° C.

with 200 rpm shaking. Following 24 hours of growth the dry cell weight of each culture was measured.

Figure 10A:
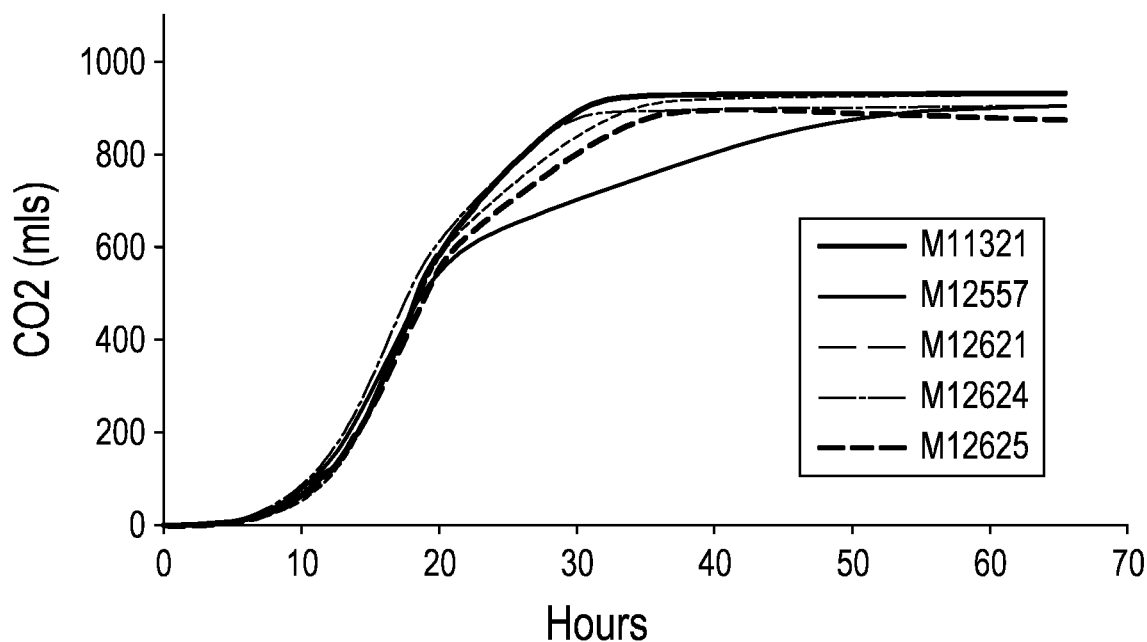
FIGS. 10A and B compare (A) $CO_2$ production (in mL), (B) residual xylose (in g/L, grey bars) and ethanol production (in g/L, ▲) in SP3 media fermented by various *S. cerevisiae* strains (M11321, M12557, M12621 (e.g., M12557 expressing a mutated $RAS2^{A66T}$ protein under the control of a the RAS2 promoter), M12624 (e.g., M12557 expressing a mutated $RAS2^{A66T}$ protein under the control of the DAN1 promoter) or M12625 (e.g., M12557 expressing a mutated $RAS2^{A66T}$ protein under the control of the ANB1 promoter)).
Figure 10B:
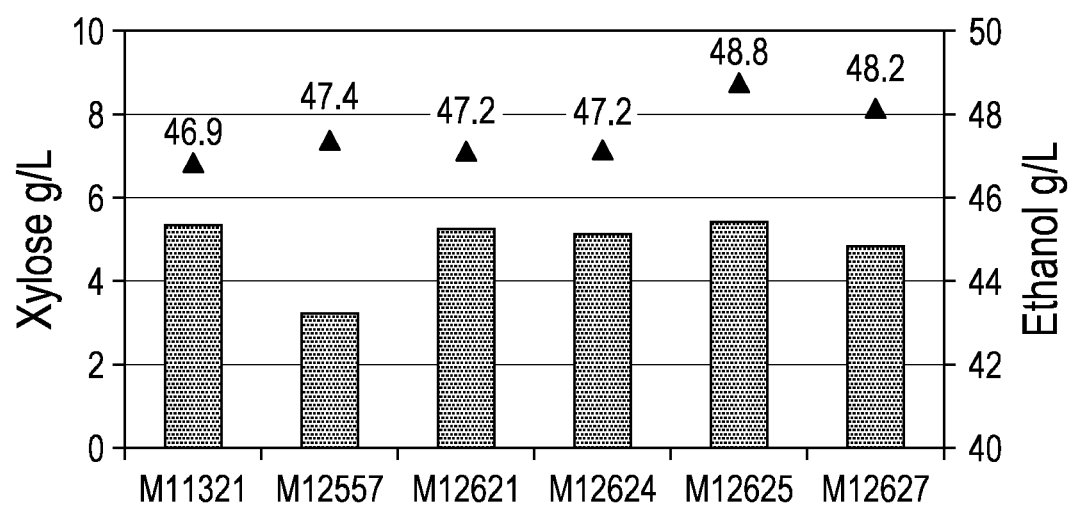

In the experimental conditions tested, strains M12621, M12624 and M12625 expressing the mutated RAS2$^{A66T}$ protein produced $CO_2$ at a faster rate than their corresponding parental strain M12557 and produced the same or more ethanol (FIGS. 10A and 10B). These results indicate that the expression of the mutated RAS2$^{A66T}$ protein does increase the rate of ethanol fermentation on xylose.

Figure 11:
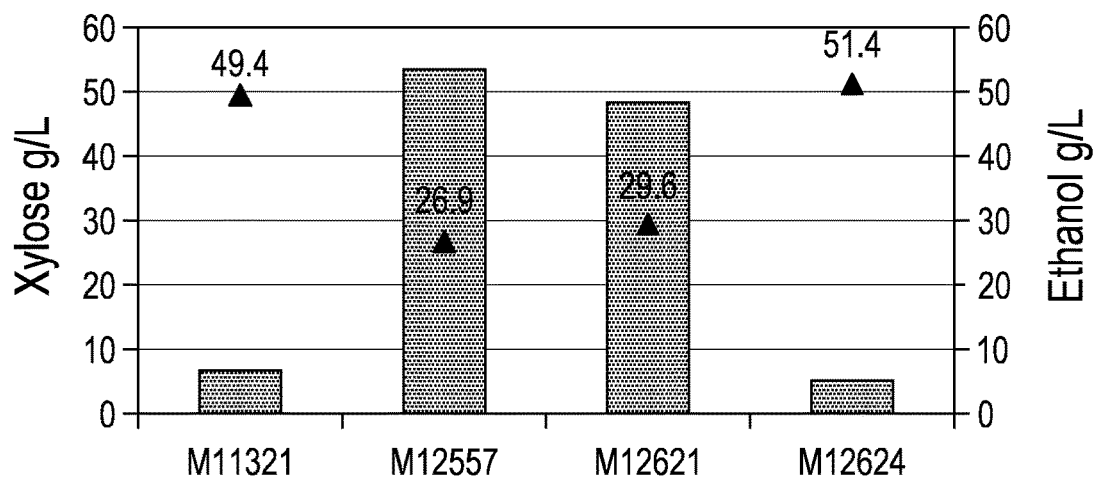
FIG. 11 illustrates residual xylose (in g/L, grey bars) and ethanol production (in g/L, ▲) in SP4 media fermented by various *S. cerevisiae* strains (M11321, M12557, M12621 and M12624).

When grown in SP4 medium, strain M12624 (expressing the RAS2$^{A66T}$ protein under the control of the DAN1 promoter) exhibited a higher xylose consumption and ethanol production than strain M12621 (expressing the RAS2$^{A66T}$ protein under the control of the RAS2 promoter) or parental strain M12557 (FIG. 11).

Figure 12:
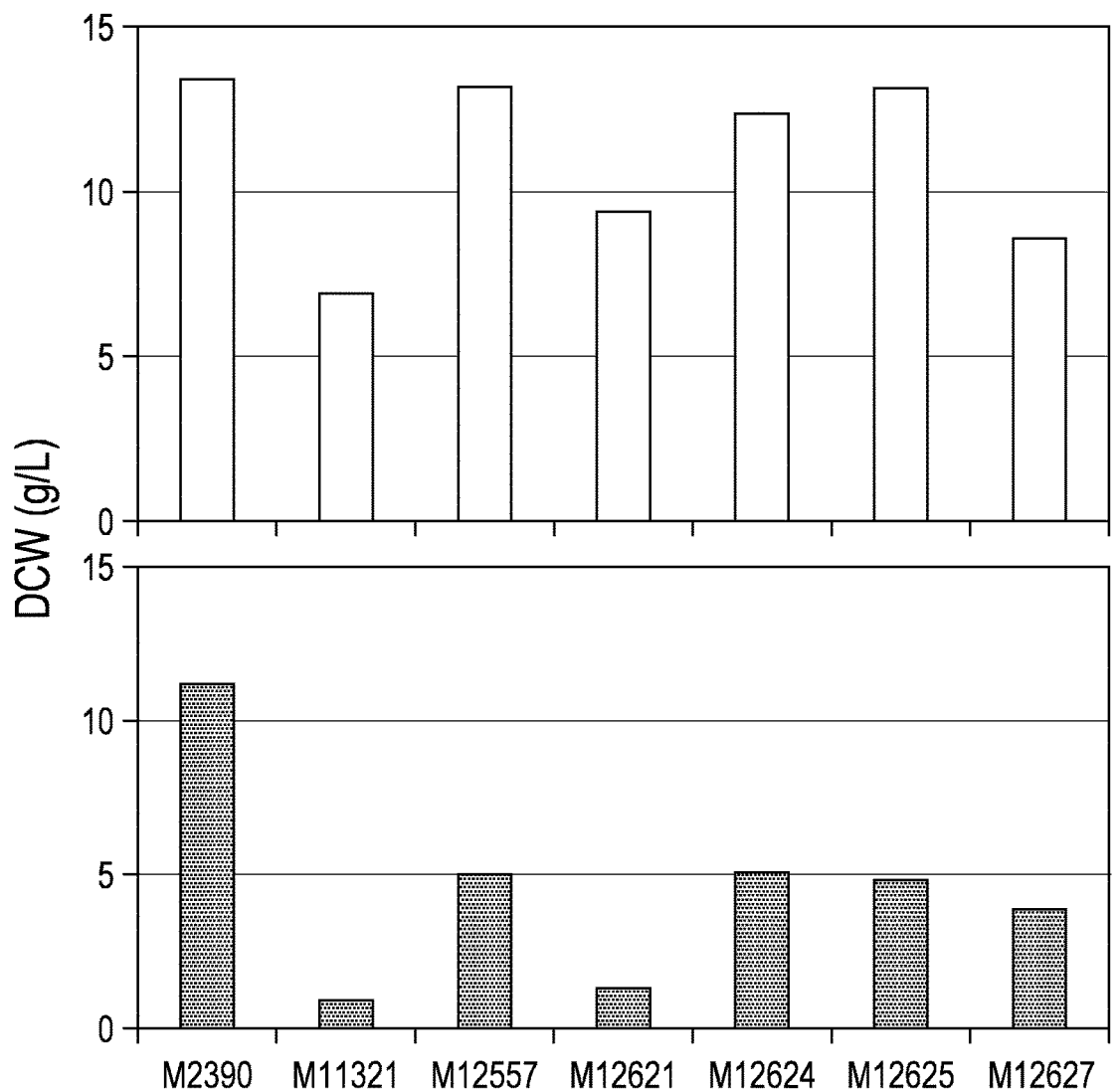
FIG. 12 illustrates dry cell weight (in g/L) production during aerobic propagation on two different molasses media: CSL/DAP (top panel, white bars) or $Urea/MgSO_4$ (bottom panel, grey bars) for various *S. cerevisiae* strains (M2390, M11321, M12557, M12621, M12624, M12625 or M12627).

When grown in molasses medium, strains M12624, M12625 and M12627 (expressing the RAS2$^{A66T}$ protein under the control of the DAN1, ANB1, or HXK1 promoters) exhibited higher production yields than strain M12621 (expressing the RAS2$^{A66T}$ protein under the control of the RAS2 promoter) (FIG. 12). Therefore, the choice of promoter used for the expression of the RAS2$^{A66T}$ protein can enable both good propagation and xylose fermentation.

EXAMPLE III—CHARACTERIZATION OF RAS2 MUTATIONS ON ARABINOSE FERMENTATION

The arabinose technology in which heterologous *Bacteroides thetaiotaomicron* AraA, AraB, AraD are expressed, and GAL80 was deleted, was integrated into two xylose utilizing strains M12359 and M13414. The two parent strains were identical except for the presence of the Ras2A66T allele at a neutral integration site of M13414 under control of the DAN1 promoter and native RAS2 terminator. Both strains still contained the native wild type RAS2 locus.

TABLE 3

Description of the *S. cerevisiae* strains of Example III

| Designation | Genotype |
|---|---|
| M12359 | The GRE3 locus of strain M2390 was replaced with expression cassettes for the pentose phosphate pathway genes RPE1, RKI1, TKL1, and TAL1 as well as the native *S. cerevisiae* xyulokinase XKS1 and a heterologous xylose isomerase gene from *Catonella morbi*. In addition the YPR1 locus was deleted and replaced with additional *C. morbi* xylose isomerase (WP_023355929) and native XKS1. Additional additional *C. morbi* xylose isomerase (WP_023355929) was introduced at two additioanl neutral integration sites. |
| M13414 | Same modifications as M12359 An heterologous Ras2 protein bearing the A66T mutation and under the control of a Dan1 promoter and the native Ras2 terminator was introduced at a neutral integration site. |
| M13570 | Same as M12359 *Bacteriodes thetaiotaomicron* arabinose isomerase araA, ribulokinase araB, and L-ribulose-5-phosphate 4-epimerase araD genes integrated at a neutral integration sites. The native GAL80 deleted. |

TABLE 3-continued

Description of the *S. cerevisiae* strains of Example III

| Designation | Genotype |
|---|---|
| M13578 | Same as M13414 *Bacteriodes thetaiotaomicron* arabinose isomerase araA, ribulokinase araB, and L-ribulose-5-phosphate 4-epimerase araD genes integrated at a neutral integration sites. The native GAL80 deleted. |

Strains M12359, M13414, M13570, and M13578 were grown overnight at 35° C. in 5 ml of YP media with 40 g/l glucose. 300 μl of each overnight culture was inoculated into a 60 ml serum bottle containing 30 ml of YP media comprising 5 g/l glucose and 35 g/l arabinose with no pH adjustment (approximately pH 6.5). The serum bottles were incubated at 32° C. with 170 rpm shaking. Pressure was monitored throughout the fermentation process and used as an estimate of $CO_2$ and ethanol production.

Following 70 hours of fermentation end point metabolite concentrations were measured on an H-column via HPLC. In brief, 1 ml was sampled from each serum bottle and cells were pelleted by centrifugation. 400 ul of supernatant was mixed with 10 μl of 10% $H_2SO_4$ and centrifuged through a 0.2 μm filter. The resulting sample was stored at 4° C. until analyzed by HPLC.

Figure 13:
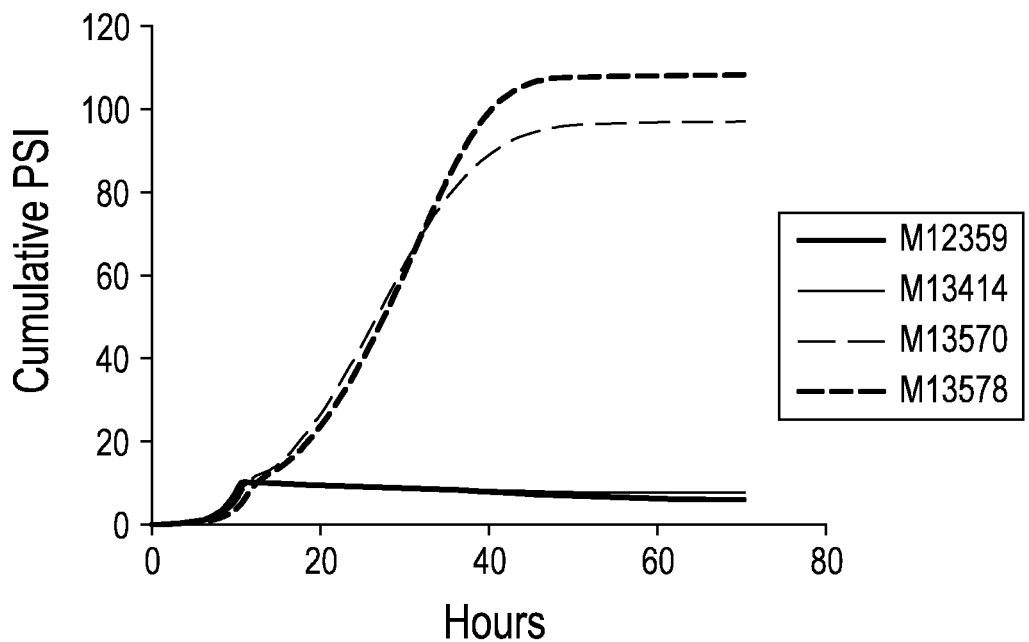
FIG. 13 illustrates the fermentation kinetics in $YPD_5A_{35}$ media for various *S. cerevisiae* strains (M12359, M13414, M13570 or M13578). Results are provided as cumulative pounds per square inch gauge (as a proxy for the production of $CO_2$) in function of hours of fermentation.
Figure 14:
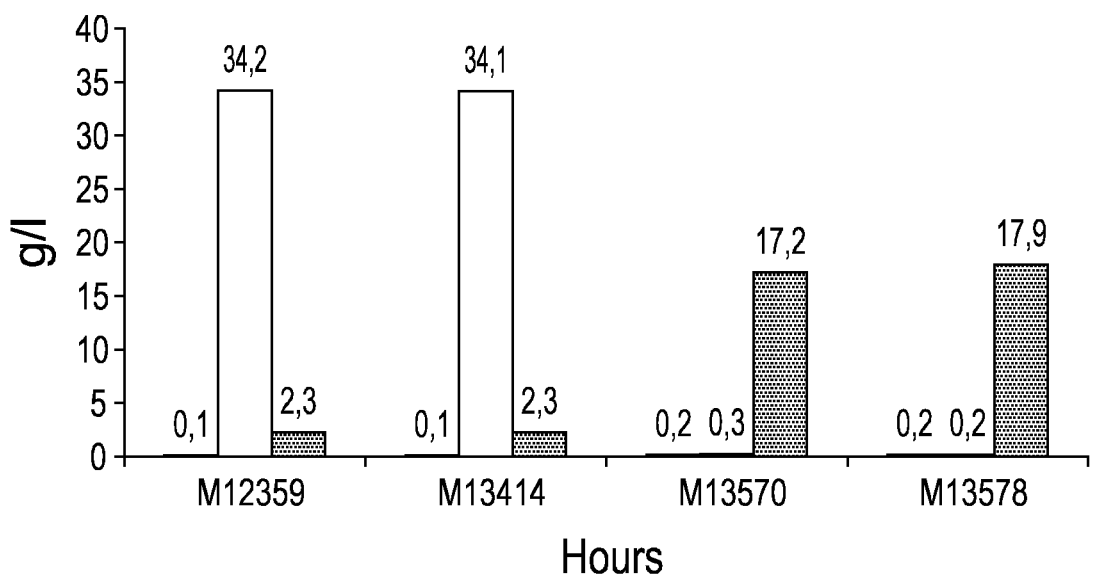
FIG. 14 provides the high-performance liquid chromatography (HPLC) analysis of end point metabolites following 70 hours of fermentation for various *S. cerevisiae* strains (M12359, M13414, M13570 or M13578). Results are provided as g/L of residual glucose (black bars), arabinose (white bars) or ethanol (hatched bars) in function of the *S. cerevisiae* strains used.

While arabinose fermentation rate appeared identical between the two strains (data not shown), M13578 which expresses the Ras2 mutant allele, appeared to generate a greater amount of $CO_2$ (FIG. 13). This result correlated with higher final ethanol titers in the HPLC analysis (FIG. 14). The Ras2 allele increased the yield of ethanol from arabinose from 0.44 g ethanol/g arabinose in M13570 to 0.46 g ethanol/g arabinose in M13578 resulting in a 4.5% yield increase for arabinose derived ethanol (FIG. 14).

While the invention has been described in connection with specific embodiments thereof, it will be understood that the scope of the claims should not be limited by the preferred embodiments set forth in the examples, but should be given the broadest interpretation consistent with the description as a whole.

REFERENCES

Kwast K E, Lai L C, Menda N, James D T 3rd, Aref S, Burke P V. Genomic analyses of anaerobically induced genes in *Saccharomyces cerevisiae*: functional roles of Rox1 and other factors in mediating the anoxic response. J Bacteriol. 2002 January; 184(1):250-65.

Mbonyi, K., Beullens, M., Detremerie, K., Geerts, L., and Thevelein, J. M. (1988). Requirement of one functional RAS gene and inability of an oncogenic ras variant to mediate the glucose-induced cyclic AMP signal in the yeast *Saccharomyces cerevisiae*. Mol. Cell. Biol. 8, 3051-3057.

Tai S L, Boer V M, Daran-Lapujade P, Walsh M C, de Winde J H, Daran J M, Pronk J T. Two-dimensional transcriptome analysis in chemostat cultures. Combinatorial effects of oxygen availability and macronutrient limitation in *Saccharomyces cerevisiae*. J Biol Chem. 2005 Jan. 7; 280(1):437-47.

Temeles, G. L., Gibbs, J. B., D'Alonzo, J. S., Sigal, I. S., and Scolnick, E. M. (1985). Yeast and mammalian ras proteins have conserved biochemical properties. Nature 313, 700-703.

ter Linde J J, Liang H, Davis R W, Steensma H Y, van Dijken J P, Pronk J T. Genome-wide transcriptional analysis of aerobic and anaerobic chemostat cultures of *Saccharomyces cerevisiae*. J Bacteriol. 1999 December; 181(24): 7409-13.

What is claimed is:

1. A method of fermenting a fermentation medium to obtain ethanol, said method comprising:

contacting a recombinant yeast host cell with the fermentation medium under conditions to allow generation of ethanol; and obtaining ethanol from the fermentation medium;

wherein:

the recombinant yeast host cell expresses a first heterologous nucleic acid molecule comprising a promoter operatively linked to a second nucleic acid molecule coding for a mutated Ras2 protein (a)

having increased activity when compared to the wild-type Ras2 protein and (b) comprising an amino acid sequence having at least 90% identity to SEQ ID NO: 1, wherein the amino acid residue at position 66 is substituted with a histidine, an isoleucine, an arginine, a leucine, an asparagine, a lysine, an aspartic acid, a methionine, a cysteine, a phenylalanine, a glutamic acid, a threonine, a glutamine, a tryptophan, a glycine, a valine, a proline, a serine, or a tyrosine residue;

the promoter is capable of increasing expression of the second nucleic acid molecule during fermentation when compared to the expression of the second nucleic acid molecule during propagation;

the fermentation medium comprises xylose and/or arabinose; and the recombinant yeast host cell is capable of utilizing (i) xylose by expressing a third heterologous nucleic acid molecule coding for (a) a xylose reductase and a xylitol dehydrogenase or (b) a xylose isomerase, and/or (ii) arabinose by expressing a fourth heterologous nucleic acid molecule coding for an arabinose isomerase, a ribulokinase and a ribulose 5-phosphate epimerase.

2. The method of claim 1, wherein the mutated Ras2 protein has the amino acid sequence of SEQ ID NO: 2 or the second nucleic acid molecule comprises the sequence of SEQ ID NO: 3.

3. The method of claim 1, wherein the promoter:

(i) is capable of increasing the expression of the second nucleic acid molecule when the recombinant yeast host cell is in at least partial anaerobic conditions when compared to a level of the expression of the second nucleic acid molecule that is obtained when the recombinant yeast host cell is placed in aerobic conditions, or (ii) is a glucose-repressible promoter.

4. The method of claim 1, wherein the recombinant yeast host cell comprises at least one copy of a RAS2 gene coding for a wild-type Ras2 protein.

5. The method of claim 1, wherein the recombinant yeast host cell is a *Saccharomyces cerevisiae* cell.

6. The method of claim 1, wherein the recombinant yeast host cell comprises the third heterologous nucleic acid molecule encoding the heterologous xylose isomerase.

7. The method of claim 1, wherein the third heterologous nucleic acid molecule further encodes a xylulokinase, a xylose reductase, a xylose dehydrogenase, a xylonate dehydratase, a xylose transketolase and/or a xylose transaldolase.

8. The method of claim 1, wherein the fourth heterologous nucleic acid molecule further encodes an arabinose transporter.

9. The method of claim 1, wherein the xylose isomerase is from *Catonella morbi*.

10. The method of claim 1, wherein the arabinose isomerase ribulokinase is from *Bacteroides thetaiotaomicron*.

11. The method of claim 1, wherein the ribulokinase is from *Bacteroides thetaiotaomicron*.

12. The method of claim 1, wherein the ribulose 5-phosphate epimerase is from *Bacteroides thetaiotaomicron*.

13. The method of claim 1, wherein the second nucleic acid molecule is a heterologous nucleic acid molecule.

14. The method of claim 1, wherein the promoter is not a RAS2 promoter from a RAS2 gene.

15. The method of claim 1, wherein the wild-type Ras2 protein has the amino acid sequence of SEQ ID NO: 1.

16. The method of claim 1, wherein the amino acid residue at position 66 of the mutated Ras2 protein is substituted with a threonine residue.

* * * * *